US011499197B2

(12) United States Patent
Moreaux et al.

(10) Patent No.: US 11,499,197 B2
(45) Date of Patent: Nov. 15, 2022

(54) PROGNOSIS METHOD OF MULTIPLE MYELOMA

(71) Applicants: CENTRE NATIONAL DE LA RECHERCHE SCIENTIFIQUE, Paris (FR); CENTRE HOSPITALIER UNIVERSITAIRE DE MONTPELLIER, Montpellier (FR); UNIVERSITÉ DE MONTPELLIER, Montpellier (FR)

(72) Inventors: Jerome Moreaux, Montpellier (FR); Hugues De Boussac, Prades-le-Lez (FR); Alboukadel Kassambara, Montpellier (FR)

(73) Assignees: CENTRE NATIONAL DE LA RECHERCHE SCIENTIFIQUE, Paris (FR); CENTRE HOSPITALIER UNIVERSITAIRE DE MONTPELLIER, Montpellier (FR); UNIVERSITÉ DE MONTPELLIER, Montpellier (FR)

( * ) Notice: Subject to any disclaimer, the term of this patent is extended or adjusted under 35 U.S.C. 154(b) by 30 days.

(21) Appl. No.: 16/759,909

(22) PCT Filed: Oct. 30, 2018

(86) PCT No.: PCT/EP2018/079749
§ 371 (c)(1),
(2) Date: Apr. 28, 2020

(87) PCT Pub. No.: WO2019/086478
PCT Pub. Date: May 9, 2019

(65) Prior Publication Data

US 2020/0325542 A1 Oct. 15, 2020

(30) Foreign Application Priority Data

Oct. 31, 2017 (EP) .................................... 17306503

(51) Int. Cl.

| | |
|---|---|
| ***C12Q 1/6886*** | (2018.01) |
| ***A61P 35/00*** | (2006.01) |
| ***A61K 31/198*** | (2006.01) |
| ***A61K 31/4375*** | (2006.01) |
| ***A61K 31/4535*** | (2006.01) |
| ***A61K 31/454*** | (2006.01) |
| ***A61K 31/4545*** | (2006.01) |
| ***A61K 31/4985*** | (2006.01) |
| ***A61K 31/506*** | (2006.01) |
| ***A61K 31/519*** | (2006.01) |
| ***A61K 31/69*** | (2006.01) |

(52) U.S. Cl.
CPC .......... *C12Q 1/6886* (2013.01); *A61K 31/198* (2013.01); *A61K 31/4375* (2013.01); *A61K 31/454* (2013.01); *A61K 31/4535* (2013.01); *A61K 31/4545* (2013.01); *A61K 31/4985* (2013.01); *A61K 31/506* (2013.01); *A61K 31/519* (2013.01); *A61K 31/69* (2013.01); *A61P 35/00* (2018.01); *C12Q 2600/118* (2013.01); *C12Q 2600/158* (2013.01)

(58) Field of Classification Search
CPC .................................................... C12Q 1/6886
USPC ............................................................ 514/64
See application file for complete search history.

(56) References Cited

FOREIGN PATENT DOCUMENTS

| | | | |
|---|---|---|---|
| EP | 2 537 942 | A1 | 12/2012 |
| WO | WO 2011/068546 | A2 | 6/2011 |
| WO | WO2011/068839 | A1 * | 6/2011 |
| WO | WO 2013/155048 | A1 | 10/2013 |
| WO | WO 2015/017803 | A1 | 2/2015 |

OTHER PUBLICATIONS

Fleuren, Emmy D. G. et al., "The kinome 'at large' in cancer", Nature Reviews Cancer (Feb. 2016), vol. 16, pp. 83-98.
Kovacs, Michael J. et al., "A phase II study of ZD6474 (ZactimaTM), a selective inhibitor of VEGFR and EGFR tyrosine kinase in patients with relapsed multiple myeloma—NCIC CTG IND.145," Invest New Drugs (2006) vol. 24, pp. 529-535.
Kuner, Ruprecht et al., "The maternal embryonic leucine zipper kinase (MELK) is upregulated in high-grade prostate cancer", J Mol Med (2013), Vo. 91, pp. 237-248.
Kyle, Robert A. et al., "Multiple Myeloma", N Engl J Med (2004), vol. 351, pp. 1860-1873.
Rollig, Christoph et al., "Multiple myeloma", Lancet 2015; 385: 2197-208, Published Online Dec. 23, 2014 at URL: http://dx.doi.org/10.1016/S0140-6736(14)60493-1.
Sawyers, Charles L., "Rational therapeutic intervention in cancer: kinases as drug targets", Current Opinion in Genetics & Development (2002), vol. 12, pp. 111-115.
Xie, Yuan et al., "Mps1/TTK: a novel target and biomarker for cancer", Journal of Drug Targeting, DOI: 10.1080/1061186X.2016.1258568.
International Search Report dated Jan. 3, 2019 issued in PCT/EP2018/079749.

(Continued)

*Primary Examiner* — Taofiq A Solola
(74) *Attorney, Agent, or Firm* — Scully, Scott, Murphy & Presser, P.C.

(57) ABSTRACT

The invention relates to a method for in vitro predicting the outcome of an individual having a multiple myeloma, comprising the steps of: a. measuring the expression level of genes coding for kinases, b. calculating a score value for each genes; and c. classifying the individual as having a good or a bad outcome.

13 Claims, 20 Drawing Sheets

Specification includes a Sequence Listing.

(56) References Cited

OTHER PUBLICATIONS

Hugues De Boussac et al., "Kinome Expression Profiling in Multiple Myeloma Identifies New Therapeutic Targets", Scientific Reports (Dec. 9, 2017), p. 26695, retrieved from the Internet: URL:https://ash.confex.com/ash/2017/webprogram/Paper102300.html [retrieved on Apr. 3, 2018].
Maugeri-Sacca M. et al., "Checkpoint kinase 1 inhibitors for potentiating systemic anticancer therapy", Cancer Treatment Reviews (Dec. 3, 2012), vol. 39, No. 5, pp. 525-533.
Nguyen Tri et al., "Synergism between bosutinib (SKI-606) and the Chk1 inhibitor (PF-00477736) in highly imatinib-resistant BCR/ABL+leukemia cells", Leukemia Research, New York, NY, US, vol. 39, No. 1, (Nov. 11, 2014), pp. 65-71.
Abramson, Hanley N., "Kinase inhibitors as potential agents in the treatment of multiple myeloma", Oncotarget (2016), vol. 7, No. 49, pp. 81926-81968.
Anderson, Kenneth C. et al., "Pathogenesis of Myeloma", Annu. Rev. Pathol. Mech. Dis. (2011), vol. 6, pp. 249-274.
Anderson, Kenneth C., "Bench-to-bedside translation of targeted therapies in multiple myeloma", J Clin Oncol. (Feb. 1, 2012), vol. 30, No. 4, pp. 445-452.
Barlogie, Bart et al., "Total therapy 2 without thalidomide in comparison with total therapy 1: role of intensified induction and posttransplantation consolidation therapies", BLOOD (Apr. 1, 2006), vol. 107, No. 7, pp. 2633-2638.
Bharti, Alok C. et al., "Curcumin (diferuloylmethane) down-regulates the constitutive activation of nuclear factor-κB and IκBκalpha kinase in human multiple myeloma cells, leading to suppression of proliferation and induction of apoptosis", BLOOD (Feb. 1, 2003), vol. 101, No. 3, pp. 1053-1062.
Bonte, Dorine et al., "Cdc7-Dbf4 Kinase Overexpression in Multiple Cancers and Tumor Cell Lines Is Correlated with p53 Inactivation1,2", Neoplasia (2008), vol. 10, No. 9, pp. 920-931.
Bullock, Nicholas et al., "The many faces of SRPK1", J Pathol (2017), vol. 241, pp. 437-440.
Chesi, Marta et al., "Frequent translocation t(4;14)(p16.3;q32.3) in multiple myeloma is associated with increased expression and activating mutations of fibroblast growth factor receptor 3", Nat Genet. (Jul. 1997), vol. 16, No. 3, pp. 260-264.
Chung, Suyoun et al., "Development of an orally-administrative MELK-targeting inhibitor that suppresses the growth of various types of human cancer", Oncotarget (Dec. 2012), vol. 3, No. 12, pp. 1629-1640.
Garcia-Sanz, R. et al., "Proliferative Activity of Plasma Cells is the Most Relevant Prognostic Factor in Elderly Multiple Myeloma Patients", Int. J. Cancer (2004), vol. 112, pp. 884-889.
Gray, Daniel et al., "Maternal Embryonic Leucine Zipper Kinase/Murine Protein Serine-Threonine Kinase 38 Is a Promising Therapeutic Target for Multiple Cancers", Cancer Res 2005 (Nov. 1, 2005), vol. 65, No. 21, pp. 9751-9761.
Hose, Dirk et al., "Proliferation is a central independent prognostic factor and target for personalized and risk-adapted treatment in multiple myeloma", haematologica (2011), vol. 96, No. 1, pp. 87-95.
Hothorn, Torsten et al., "On the exact distribution of maximally selected rank statistics", Computational Statistics & Data Analysis (2003), vol. 43 121-137.
Hsu, Jung-Hsin et al., "The AKT kinase is activated in multiple myeloma tumor cells", BLOOD (Nov. 1, 2001), vol. 98, No. 9, pp. 2853-2855.
Hyun, Teresa et al., "Loss of PTEN expression leading to high Akt activation in human multiple myelomas", BLOOD (Nov. 15, 2000), vol. 96, No. 10, pp. 3560-3568.
Ji, Wenbin "OTSSP167 Abrogates Mitotic Checkpoint through Inhibiting Multiple Mitotic Kinases", PLOS ONE DOI:10.1371/journal.pone.0153518 (Apr. 15, 2016), pp. 1-15.
Jourdan, Michel et al., "An in vitro model of differentiation of memory B cells into plasmablasts and plasma cells including detailed phenotypic and molecular characterization", BLOOD (Dec. 10, 2009), vol. 114, No. 25, pp. 5173-5181.
Jourdan, Michel et al., "IL-6 supports the generation of human long-lived plasma cells in combination with either APRIL or stromal cell-soluble factors", Leukemia (2014), vol. 28, pp. 1647-1656.
Kassambara, Alboukadel et al., "GenomicScape: An Easy-to-Use Web Tool for Gene Expression Data Analysis Application to Investigate the Molecular Events in the Differentiation of B Cells into Plasma Cells", PLOS Computational Biology DOI:10.1371/journal.pcbi.1004077 (Jan. 29, 2015), pp. 1-10.
Landau, Heather J. et al., "The Checkpoint Kinase Inhibitor AZD7762 Potentiates Chemotherapy-Induced Apoptosis of p53-Mutated Multiple Myeloma Cells", Mol Cancer Ther (Aug. 2012), vol. 11, No. 8, pp. 1781-1789.
Lin, Ann et al., "CRISPR/Cas9 mutagenesis invalidates a putative cancer dependency targeted in on-going clinical trials", Cancer Biology Genes and Chromosomes, eLife 2017;6:e24179. DOI: 10.7554/eLife.24179, pp. 1-17.
Liu, Xiaoqi, "Targeting Polo-Like Kinases: A Promising Therapeutic Approach for Cancer Treatment", Translational Oncology (2015), vol. 8, No. 3, pp. 185-194.
Ma, Zhikun et al., "The Chk1 inhibitor AZD7762 sensitises p53 mutant breast cancer cells to radiation in vitro and in vivo", Molecular Medicine Reports (2012), vol. 6, pp. 897-903.
Maes, Anke et al., "The therapeutic potential of cell cycle targeting in multiple myeloma", Oncotarget (2017), vol. 8, No. 52, pp. 90501-90520.
Meng, Fanying et al., "Enhancement of hypoxia-activated prodrug TH-302 anti-tumor activity by Chk1 inhibition", BMC Cancer (2015), vol. 15, No. 422, pp. 1-17.
Mitsiades, Constantine S., "Inhibition of the insulin-like growth factor receptor-1 tyrosine kinase activity as a therapeutic strategy for multiple myeloma, other hematologic malignancies, and solid tumors", Cancer Cell (Mar. 2004), vol. 5, pp. 221-230.
Moreaux, Jerome et al., "A high-risk signature for patients with multiple myeloma established from the molecular classification of human myeloma cell lines", haematologica (2011), vol. 96, No. 4, pp. 574-582.
Moreaux, Jerome et al., "Development of Gene Expression-Based Score to Predict Sensitivity of Multiple Myeloma Cells to DNA Methylation Inhibitors", Mol Cancer Ther (Dec. 2012), vol. 11, No. 12, pp. 2685-2692.
Nair, Bijay et al., "Superior results of Total Therapy 3 (2003-33) in gene expression profiling-defined low-risk multiple myeloma confirmed in subsequent trial 2006-66 with VRD maintenance", BLOOD (May 27, 2010), vol. 115, No. 21, pp. 4168-4173.
Ohashi, Takuma et al., "Overexpression of PBK/TOPK relates to tumour malignant potential and poor outcome of gastric carcinoma", British Journal of Cancer (2017), vol. 116, 218-226.
Otto, Tobias et al., "Cell cycle proteins as promising targets in cancer therapy", Nat Rev Cancer. (Jan. 27, 2017), vol. 17, No. 2, pp. 93-115.
Pedranzini, Laura et al., "Pyridone 6, A Pan-Janus-Activated Kinase Inhibitor, Induces Growth Inhibition of Multiple Myeloma Cells", Cancer Res 2006 (Oct. 1, 2006), vol. 66, No. 19, pp. 9714-9722.
Pei, Xin-Yan et al., "Cytokinetically quiescent (G0/G1) human multiple myeloma cells are susceptible to simultaneous nhibition of Chk1 and MEK1/2", Blood (Nov. 10, 2011), vol. 118, No. 19, pp. 5189-5200.
Pene, Frederic et al., "Role of the phosphatidylinositol 3-kinase/Akt and mTOR/P70S6-kinase pathways in the proliferation and apoptosis in multiple myeloma", Oncogene (2002), vol. 21, pp. 6587-6597.
Podar, Klaus et al., "Targeting PKC in multiple myeloma: in vitro and in vivo effects of the novel, orally available small-molecule inhibitor enzastaurin (LY317615.HCl)", BLOOD (Feb. 15, 2007), vol. 109, No. 4, pp. 1669-1677.
Sabatier, Renaud et al.,"Kinome expression profiling and prognosis of basal breast cancers", Molecular Cancer (2011), vol. 10, No. 86, pp. 1-11.
Santra, Madhumita et al., "Asubset of multiple myeloma harboring the t(4;14)(p16;q32) translocation lacks FGFR3 expression but

(56) References Cited

OTHER PUBLICATIONS maintains an IGH/MMSET fusion transcript", BLOOD (Mar. 15, 2003), vol. 101, No. 6, pp. 2374-2376.
Shaughnessy, John, "Amplification and overexpression of CKS1B at chromosome band 1q21 is associated with reduced levels of p27 Kip1 and an aggressive clinical course in multiple myeloma", Hematology (2005), vol. 10, Supplement 1, pp. 117-126.
Shi, Lei et al., "Over-expression of CKS1B activates both MEK/ ERK and JAK/ STAT3 signaling pathways and promotes myeloma cell drugresistance", OncoTarget (May 2010), pp. 22-33.
Siegel, Rebecca, "Cancer Statistics, 2012", CA: A Cancer Journal for Clinicians (2012), vol. 62, pp. 10-29.
Sprynski, Anne Catherine et al., "The role of IGF-1 as a major growth factor for myeloma cell lines and the prognostic relevance of the expression of its receptor", BLOOD (May 7, 2009), vol. 113, No. 19, pp. 4614-4626.
Stefka, "Anti-myeloma activity of MELK inhibitor OTS167: effects on drug-resistant myeloma cells and putative myeloma stem cell replenishment of malignant plasma cells", Blood Cancer Journal (Aug. 19, 2016) 6, e460; doi:10.1038/bcj.2016.71, pp. 1-5.
Tiedemann, Rodger E. et al.,"Kinome-wide RNAi studies in human multiple myeloma identify vulnerable kinase targets, including a lymphoid-restricted kinase, GRK6", BLOOD (Feb. 25, 2010), vol. 115, No. 8, pp. 1594-1604.
Zhan, Fenghuang et al., "The molecular classification of multiple myeloma", BLOOD (Sep. 15, 2006), vol. 108, No. 6, pp. 2020-2028.
Chou, Ting-Chao et al., "Quantitative Analysis of Dose-Effect Relationships: The Combined Effects of Multiple Drugs of Enzyme Inhibitors", Advances in Enzyme Regulation 22(C) (Feb. 1984), pp. 27-55.
Evans, Robert et al., "Aurora A kinase RNAi and small molecule inhibition of Aurora kinases with VE-465 induce apoptotic death in multiple myeloma cells", Leukemia & Lymphoma (Mar. 2008) vol. 49, No. 3, pp. 559-569.
De Boussac, H., et al., "Kinome expression profiling to target new therapeutic avenues in multiple myeloma", Haematologica 2020, Received: Oct. 5, 2018, Accepted: Jul. 5, 2019, Pre-published: Jul. 9, 2019, pp. 784-795, vol. 105(3).

* cited by examiner

A : Melphalan+AZD7762 IC20; B: Melphalan+OTSSP167 IC20; C: Melphalan+CB IC20; D: Melphalan+HITOPK032 IC20; E: Melphalan+XL413 IC20; F: Melphalan+AZ3146 IC20; G: Melphalan+SRPIN340 IC20.

A : Melphalan+AZD7762 IC20; B: Melphalan+OTSSP167 IC20; C: Melphalan+CB IC20; D: Melphalan+HITOPK032 IC20; E: Melphalan+XL413 IC20; F: Melphalan+AZ3146 IC20; G: Melphalan+SRPIN340 IC20.

*, , *= IC50Mneg is significantly different from IC50MRes

SEQUENCE LISTING

```
<160> NUMBER OF SEQ ID NOS: 36

<210> SEQ ID NO 1
<211> LENGTH: 1212
<212> TYPE: DNA
<213> ORGANISM: Homo sapiens

<400> SEQUENCE: 1

atggaccgat ctaaagaaaa ctgcatttca ggacctgtta aggctacagc tccagttgga      60

ggtccaaaac gtgttctcgt gactcagcaa tttccttgtc agaatccatt acctgtaaat     120

agtggccagg ctcagcgggt cttgtgtcct tcaaattctt cccagcgcat tcctttgcaa     180

gcacaaaagc ttgtctccag tcacaagccg gttcagaatc agaagcagaa gcaattgcag     240

gcaaccagtg tacctcatcc tgtctccagg ccactgaata acacccaaaa gagcaagcag     300

cccctgccat cggcacctga aaataatcct gaggaggaac tggcatcaaa acagaaaaat     360

gaagaatcaa aaaagaggca gtgggctttg gaagactttg aaattggtcg ccctctgggt     420

aaaggaaagt ttggtaatgt ttatttggca agagaaaagc aaagcaagtt tattctggct     480

cttaaagtgt tatttaaagc tcagctggag aaagccggag tggagcatca gctcagaaga     540

gaagtagaaa tacagtccca ccttcggcat cctaatattc ttagactgta tggttatttc     600

catgatgcta ccagagtcta cctaattctg gaatatgcac cacttggaac agtttataga     660

gaacttcaga aactttcaaa gtttgatgag cagagaactg ctacttatat aacagaattg     720
```

-continued

```
gcaaatgccc tgtcttactg tcattcgaag agagttattc atagagacat taagccagag    780

aacttacttc ttggatcagc tggagagctt aaaattgcag attttgggtg gtcagtacat    840

gctccatctt ccaggaggac cactctctgt ggcaccctgg actacctgcc ccctgaaatg    900

attgaaggtc ggatgcatga tgagaaggtg gatctctgga gccttggagt tctttgctat    960

gaatttttag ttgggaagcc tccttttgag gcaaacacat accaagagac ctacaaaaga   1020

atatcacggg ttgaattcac attccctgac tttgtaacag agggagccag ggacctcatt   1080

tcaagactgt tgaagcataa tcccagccag aggccaatgc tcagagaagt acttgaacac   1140

ccctggatca cagcaaattc atcaaaacca tcaaattgcc aaaacaaaga atcagctagc   1200

aaacagtctt ag                                                       1212
```

<210> SEQ ID NO 2
<211> LENGTH: 3258
<212> TYPE: DNA
<213> ORGANISM: Homo sapiens

<400> SEQUENCE: 2

```
atggacaccc cggaaaatgt ccttcagatg cttgaagccc acatgcagag ctacaagggc     60

aatgaccctc ttggtgaatg ggaaagatac atacagtggg tagaagagaa ttttcctgag    120

aataaagaat acttgataac tttactagaa catttaatga aggaattttt agataagaag    180

aaataccaca atgacccaag attcatcagt tattgtttaa aatttgctga gtacaacagt    240

gacctccatc aatttttga gtttctgtac aaccatggga ttggaaccct gtcatcccct    300

ctgtacattg cctgggcggg gcatctggaa gcccaaggag agctgcagca tgccagtgct    360

gtccttcaga gaggaattca aaaccaggct gaacccagag agttcctgca acaacaatac    420

aggttatttc agacacgcct cactgaaacc catttgccag ctcaagctag aacctcagaa    480

cctctgcata atgttcaggt tttaaatcaa atgataacat caaaatcaaa tccaggaaat    540

aacatggcct gcatttctaa gaatcagggt tcagagcttt ctggagtgat atcttcagct    600

tgtgataaag agtcaaatat ggaacgaaga gtgatcacga tttctaaatc agaatattct    660

gtgcactcat ctttggcatc caaagttgat gttgagcagg ttgttatgta ttgcaaggag    720

aagcttattc gtggggaatc agaattttcc tttgaagaat tgagagccca gaaatacaat    780

caacggagaa agcatgagca atgggtaaat gaagacagac attatatgaa aaggaaagaa    840

gcaaatgctt ttgaagaaca gctattaaaa cagaaaatgg atgaacttca taagaagttg    900

catcaggtgg tggagacatc ccatgaggat ctgcccgctt cccaggaaag gtccgaggtt    960

aatccagcac gtatggggcc aagtgtaggc tcccagcagg aactgagagc gccatgtctt   1020

ccagtaacct atcagcagac accagtgaac atggaaaaga acccaagaga ggcacctcct   1080

gttgttcctc ctttggcaaa tgctatttct gcagctttgg tgtccccagc caccagccag   1140

agcattgctc ctcctgttcc tttgaaagcc cagacagtaa cagactccat gtttgcagtg   1200

gccagcaaag atgctggatg tgtgaataag agtactcatg aattcaagcc acagagtgga   1260

gcagagatca aagaagggtg tgaaacacat aaggttgcca acacaagttc ttttcacaca   1320

actccaaaca catcactggg aatggttcag gcaacgccat ccaaagtgca gccatcaccc   1380

accgtgcaca caaaagaagc attaggtttc atcatgaata tgtttcaggc tcctacactt   1440

cctgatattt ctgatgacaa agatgaatgg caatctctag atcaaaatga agatgcattt   1500

gaagcccagt ttcaaaaaaa tgtaaggtca tctggggctt ggggagtcaa taagatcatc   1560

tcttctttgt catctgcttt tcatgtgttt gaagatggaa acaaagaaaa ttatggatta   1620
```

-continued ccacagccta aaaataaacc cacaggagcc aggacctttg gagaacgctc tgtcagcaga 1680
cttccttcaa aaccaaagga ggaagtgcct catgctgaag agtttttgga tgactcaact 1740
gtatggggta ttcgctgcaa caaaaccctg gcacccagtc ctaagagccc aggagacttc 1800
acatctgctg cacaacttgc gtctacacca ttccacaagc ttccagtgga gtcagtgcac 1860
attttagaag ataaagaaaa tgtggtagca aaacagtgta cccaggcgac tttggattct 1920
tgtgaggaaa acatggtggt gccttcaagg gatggaaaat tcagtccaat tcaagagaaa 1980
agcccaaaac aggccttgtc gtctcacatg tattcagcat ccttacttcg tctgagccag 2040
cctgctgcag gtggggtact tacctgtgag gcagagttgg gcgttgaggc ttgcagactc 2100
acagacactg acgctgccat tgcagaagat ccaccagatg ctattgctgg gctccaagca 2160
gaatggatgc agatgagttc acttgggact gttgatgctc caaacttcat tgttgggaac 2220
ccatgggatg ataagctgat tttcaaactt ttatctgggc tttctaaacc agtgagttcc 2280
tatccaaata cttttgaatg gcaatgtaaa cttccagcca tcaagcccaa gactgaattt 2340
caattgggtt ctaagctggt ctatgtccat caccttcttg gagaaggagc ctttgcccag 2400
gtgtacgaag ctacccaggg agatctgaat gatgctaaaa ataaacagaa atttgtttta 2460
aaggtccaaa agcctgccaa cccctgggaa ttctacattg ggacccagtt gatggaaaga 2520
ctaaagccat ctatgcagca catgtttatg aagttctatt ctgcccactt attccagaat 2580
ggcagtgtat tagtaggaga gctctacagc tatggaacat tattaaatgc cattaacctc 2640
tataaaaata cccctgaaaa agtgatgcct caaggtcttg tcatctcttt tgctatgaga 2700
atgctttaca tgattgagca agtgcatgac tgtgaaatca ttcatggaga cattaaacca 2760
gacaatttca tacttggaaa cggatttttg gaacaggatg atgaagatga tttatctgct 2820
ggcttggcac tgattgacct gggtcagagt atagatatga aactttttcc aaaaggaact 2880
atattcacag caaagtgtga aacatctggt tttcagtgtg ttgagatgct cagcaacaaa 2940
ccatggaact accagatcga ttactttggg gttgctgcaa cagtatattg catgctcttt 3000
ggcacttaca tgaaagtgaa aaatgaagga ggagagtgta agcctgaagg tctttttaga 3060
aggcttcctc atttggatat gtggaatgaa tttttttcatg ttatgttgaa tattccagat 3120
tgtcatcatc ttccatcttt ggatttgtta aggcaaaagc tgaagaaagt atttcaacaa 3180
cactatacta acaagattag ggccctacgt aataggctaa ttgtactgct cttagaatgt 3240
aagcgttcac gaaaataa 3258

<210> SEQ ID NO 3
<211> LENGTH: 3153
<212> TYPE: DNA
<213> ORGANISM: Homo sapiens

<400> SEQUENCE: 3
atggcggcgg tgaagaagga agggggtgct ctgagtgaag ccatgtccct ggagggagat 60
gaatgggaac tgagtaaaga aaatgtacaa cctttaaggc aagggcggat catgtccacg 120
cttcagggag cactggcaca agaatctgcc tgtaacaata ctcttcagca gcagaaacgg 180
gcatttgaat atgaaattcg attttacact ggaaatgacc ctctggatgt ttgggatagg 240
tatatcagct ggacagagca gaactatcct caaggtggga aggagagtaa tatgtcaacg 300
ttattagaaa gagctgtaga agcactacaa ggagaaaaac gatattatag tgatcctcga 360
tttctcaatc tctggcttaa attagggcgt ttatgcaatg agcctttgga tatgtacagt 420

-continued

```
tacttgcaca accaagggat tggtgtttca cttgctcagt tctatatctc atgggcagaa    480
gaatatgaag ctagagaaaa ctttaggaaa gcagatgcga tatttcagga agggattcaa    540
cagaaggctg aaccactaga aagactacag tcccagcacc gacaattcca agctcgagtg    600
tctcggcaaa ctctgttggc acttgagaaa gaagaagagg aggaagtttt tgagtcttct    660
gtaccacaac gaagcacact agctgaacta aagagcaaag ggaaaaagac agcaagagct    720
ccaatcatcc gtgtaggagg tgctctcaag gctccaagcc agaacagagg actccaaaat    780
ccatttcctc aacagatgca aaataatagt agaattactg tttttgatga aaatgctgat    840
gaggcttcta cagcagagtt gtctaagcct acagtccagc catggatagc accccccatg    900
cccagggcca aagagaatga gctgcaagca ggcccttgga acacaggcag gtccttggaa    960
cacaggcctc gtggcaatac agcttcactg atagctgtac ccgctgtgct tcccagtttc   1020
actccatatg tggaagagac tgcacgacag ccagttatga caccatgtaa aattgaacct   1080
agtataaacc acatcctaag caccagaaag cctggaaagg aagaaggaga tcctctacaa   1140
agggttcaga gccatcagca agcgtctgag gagaagaaag agaagatgat gtattgtaag   1200
gagaagattt atgcaggagt aggggaattc tcctttgaag aaattcgggc tgaagttttc   1260
cggaagaaat taaaagagca aagggaagcc gagctattga ccagtgcaga gaagagagca   1320
gaaatgcaga aacagattga agagatggag aagaagctaa aagaaatcca aactactcag   1380
caagaaagaa caggtgatca gcaagaagag acgatgccta caaaggagac aactaaactg   1440
caaattgctt ccgagtctca gaaaatacca ggaatgactc tatccagttc tgtttgtcaa   1500
gtaaactgtt gtgccagaga aacttcactt gcggagaaca tttggcagga acaacctcat   1560
tctaaaggtc ccagtgtacc tttctccatt tttgatgagt ttcttctttc agaaaagaag   1620
aataaaagtc ctcctgcaga tcccccacga gttttagctc aacgaagacc ccttgcagtt   1680
ctcaaaacct cagaaagcat cacctcaaat gaagatgtgt ctccagatgt ttgtgatgaa   1740
tttacaggaa ttgaaccctt gagcgaggat gccattatca caggcttcag aaatgtaaca   1800
atttgtccta acccagaaga cacttgtgac tttgccagag cagctcgttt tgtatccact   1860
ccttttcatg agataatgtc cttgaaggat ctcccttctg atcctgagag actgttaccg   1920
gaagaagatc tagatgtaaa gacctctgag gaccagcaga cagcttgtgg cactatctac   1980
agtcagactc tcagcatcaa gaagctgagc ccaattattg aagacagtcg tgaagccaca   2040
cactcctctg gcttctctgg ttcttctgcc tcggttgcaa gcacctcctc catcaaatgt   2100
cttcaaattc ctgagaaact agaacttact aatgagactt cagaaaaccc tactcagtca   2160
ccatggtgtt cacagtatcg cagacagcta ctgaagtccc taccagagtt aagtgcctct   2220
gcagagttgt gtatagaaga cagaccaatg cctaagttgg aaattgagaa ggaaattgaa   2280
ttaggtaatg aggattactg cattaaacga gaatacctaa tatgtgaaga ttacaagtta   2340
ttctgggtgg cgccaagaaa ctctgcagaa ttaacagtaa taaaggtatc ttctcaacct   2400
gtcccatggg acttttatat caacctcaag ttaaaggaac gtttaaatga agattttgat   2460
catttttgca gctgttatca atatcaagat ggctgtattg tttggcacca atatataaac   2520
tgcttcaccc ttcaggatct tctccaacac agtgaatata ttacccatga aataacagtg   2580
ttgattattt ataacctttt gacaatagtg gagatgctac acaaagcaga aatagtccat   2640
ggtgacttga gtccaaggtg tctgattctc agaaacagaa tccacgatcc ctatgattgt   2700
aacaagaaca atcaagcttt gaagatagtg gacttttcct acagtgttga ccttagggtg   2760
cagctggatg tttttaccct cagcggcttt cggactgtac agatcctgga aggacaaaag   2820
```

```
atcctggcta actgttcttc tccctaccag gtagacctgt ttggtatagc agatttagca   2880

catttactat tgttcaagga acacctacag gtcttctggg atgggtcctt ctggaaactt   2940

agccaaaata tttctgagct aaaagatggt gaattgtgga ataaattctt tgtgcggatt   3000

ctgaatgcca atgatgaggc cacagtgtct gttcttgggg agcttgcagc agaaatgaat   3060

ggggtttttg acactacatt ccaaagtcac ctgaacaaag ccttatggaa ggtagggaag   3120

ttaactagtc ctggggcttt gctctttcag tga                                3153
```

<210> SEQ ID NO 4
<211> LENGTH: 1725
<212> TYPE: DNA
<213> ORGANISM: Homo sapiens

<400> SEQUENCE: 4

```
atggaggcgt ctttggggat tcagatggat gagccaatgg ctttttctcc ccagcgtgac     60

cggtttcagg ctgaaggctc tttaaaaaaa aacgagcaga attttaaact tgcaggtgtt    120

aaaaaagata ttgagaagct ttatgaagct gtaccacagc ttagtaatgt gtttaagatt    180

gaggacaaaa ttggagaagg cactttcagc tctgtttatt tggccacagc acagttacaa    240

gtaggacctg aagagaaaat tgctctaaaa cacttgattc caacaagtca tcctataaga    300

attgcagctg aacttcagtg cctaacagtg gctgggggc aagataatgt catgggagtt    360

aaatactgct ttaggaagaa tgatcatgta gttattgcta tgccatatct ggagcatgag    420

tcgtttttgg acattctgaa ttctctttcc tttcaagaag tacgggaata tatgcttaat    480

ctgttcaaag ctttgaaacg cattcatcag tttggtattg ttcaccgtga tgttaagccc    540

agcaattttt tatataatag gcgcctgaaa aagtatgcct tggtagactt tggtttggcc    600

caaggaaccc atgatacgaa aatagagctt cttaaatttg tccagtctga agctcagcag    660

gaaaggtgtt cacaaaacaa atcccacata atcacaggaa acaagattcc actgagtggc    720

ccagtaccta aggagctgga tcagcagtcc accacaaaag cttctgttaa aagaccctac    780

acaaatgcac aaattcagat taaacaagga aaagacggaa aggagggatc tgtaggcctt    840

tctgtccagc gctctgtttt tggagaaaga aatttcaata tacacagctc catttcacat    900

gagagccctg cagtgaaact catgaagcag tcaaagactg tggatgtact gtctagaaag    960

ttagcaacaa aaaagaaggc tatttctaca aaagttatga atagtgctgt gatgaggaaa   1020

actgccagtt cttgcccagc tagcctgacc tgtgactgct atgcaacaga taaagtttgt   1080

agtatttgcc tttcaaggcg tcagcaggtt gcccctaggg caggtacacc aggattcaga   1140

gcaccagagg tcttgacaaa gtgccccaat caaactacag caattgacat gtggtctgca   1200

ggtgtcatat ttctttcttt gcttagtgga cgatatccat tttataaagc aagtgatgat   1260

ttaactgctt tggcccaaat tatgacaatt aggggatcca gagaaactat ccaagctgct   1320

aaaacttttg ggaaatcaat attatgtagc aaagaagttc cagcacaaga cttgagaaaa   1380

ctctgtgaga gactcagggg tatggattct agcactccca agttaacaag tgatatacaa   1440

gggcatgctt ctcatcaacc agctatttca gagaagactg accataaagc ttcttgcctc   1500

gttcaaacac ctccaggaca atactcaggg aattcattta aaaaggggga tagtaatagc   1560

tgtgagcatt gttttgatga gtataatacc aatttagaag gctggaatga ggtacctgat   1620

gaagcttatg acctgcttga taaacttcta gatctaaatc cagcttcaag aataacagca   1680

gaagaagctt tgttgcatcc attttttaaa gatatgagct tgtga                   1725
```

<210> SEQ ID NO 5
<211> LENGTH: 507
<212> TYPE: DNA
<213> ORGANISM: Homo sapiens

<400> SEQUENCE: 5
atggccgagc cttgggggaa cgagttggcg tccgcagctg ccagggggga cctagagcaa 60
cttactagtt tgttgcaaaa taatgtaaac gtcaatgcac aaaatggatt tggaaggact 120
gcgctgcagg ttatgaaact tggaaatccc gagattgcca ggagactgct acttagaggt 180
gctaatcccg atttgaaaga ccgaactggt ttcgctgtca ttcatgatgc ggccagagca 240
ggtttcctgg acactttaca gactttgctg gagtttcaag ctgatgttaa catcgaggat 300
aatgaaggga acctgccctt gcacttggct gccaaagaag gccacctccg ggtggtggag 360
ttcctggtga agcacacggc cagcaatgtg gggcatcgga accataaggg ggacaccgcc 420
tgtgatttgg ccaggctcta tgggaggaat gaggttgtta gcctgatgca ggcaaacggg 480
gctgggggag ccacaaatct tcaataa 507

<210> SEQ ID NO 6
<211> LENGTH: 519
<212> TYPE: DNA
<213> ORGANISM: Homo sapiens

<400> SEQUENCE: 6
atgaagccgc ccagttcaat acaaacaagt tgtaaattta aagatgttag aagaaatgtc 60
caaaaagata cagaagaact aaagagctgt ggtatacaag acatatttgt tttctgcacc 120
agaggggaac tgtcaaaata tagagtccca aaccttctgg atctctacca gcaatgtgga 180
attatcaccc atcatcatcc aatcgcagat ggagggactc ctgacatagc cagctgctgt 240
gaaataatgg aagagcttac aacctgcctt aaaaattacc gaaaaacctt aatacactgc 300
tatggaggac ttgggagatc ttgtcttgta gctgcttgtc tcctactata cctgtctgac 360
acaatatcac cagagcaagc catagacagc ctgcgagacc taagaggatc cggggcaata 420
cagaccatca agcaatacaa ttatcttcat gagtttcggg acaaattagc tgcacatcta 480
tcatcaagag attcacaatc aagatctgta tcaagataa 519

<210> SEQ ID NO 7
<211> LENGTH: 1329
<212> TYPE: DNA
<213> ORGANISM: Homo sapiens

<400> SEQUENCE: 7
atggcagtgc cctttgtgga agactgggac ttggtgcaaa ccctgggaga aggtgcctat 60
ggagaagttc aacttgctgt gaatagagta actgaagaag cagtcgcagt gaagattgta 120
gatatgaagc gtgccgtaga ctgtccagaa aatattaaga aagagatctg tatcaataaa 180
atgctaaatc atgaaaatgt agtaaaattc tatggtcaca ggagagaagg caatatccaa 240
tatttatttc tggagtactg tagtggagga gagcttttttg acagaataga gccagacata 300
ggcatgcctg aaccagatgc tcagagattc ttccatcaac tcatggcagg ggtggtttat 360
ctgcatggta ttggaataac tcacagggat attaaaccag aaaatcttct gttggatgaa 420
agggataacc tcaaaatctc agactttggc ttggcaacag tatttcggta taataatcgt 480
gagcgtttgt tgaacaagat gtgtggtact ttaccatatg ttgctccaga acttctgaag 540
agaagagaat ttcatgcaga accagttgat gtttggtcct gtggaatagt acttactgca 600
atgctcgctg gagaattgcc atgggaccaa cccagtgaca gctgtcagga gtattctgac 660
tggaaagaaa aaaaaacata cctcaaccct tggaaaaaaa tcgattctgc tcctctagct 720
ctgctgcata aaatcttagt tgagaatcca tcagcaagaa ttaccattcc agacatcaaa 780
aaagatagat ggtacaacaa acccctcaag aaaggggcaa aaaggccccg agtcacttca 840
ggtggtgtgt cagagtctcc cagtggattt tctaagcaca ttcaatccaa tttggacttc 900
tctccagtaa acagtgcttc tagtgaagaa aatgtgaagt actccagttc tcagccagaa 960
ccccgcacag gtctttcctt atgggatacc agcccctcat acattgataa attggtacaa 1020
gggatcagct tttcccagcc cacatgtcct gatcatatgc ttttgaatag tcagttactt 1080
ggcaccccag gatcctcaca gaacccctgg cagcggttgg tcaaaagaat gacacgattc 1140
tttaccaaat tggatgcaga caaatcttat caatgcctga aagagacttg tgagaagttg 1200
ggctatcaat ggaagaaaag ttgtatgaat cagggtgatg gattggagtt caagagacac 1260
ttcctgaaga ttaaagggaa gctgattgat attgtgagca gccagaagat ttggcttcct 1320
gccacatga 1329

<210> SEQ ID NO 8
<211> LENGTH: 240
<212> TYPE: DNA
<213> ORGANISM: Homo sapiens

<400> SEQUENCE: 8
atgtcgcaca aacaaattta ctattcggac aaatacgacg acgaggagtt tgagtatcga 60
catgtcatgc tgcccaagga catagccaag ctggtcccta aaacccatct gatgtctgaa 120
tctgaatgga ggaatcttgg cgttcagcag agtcagggat gggtccatta tatgatccat 180
gaaccagaac ctcacatctt gctgttccgg cgcccactac ccaagaaacc aaagaaatga 240

<210> SEQ ID NO 9
<211> LENGTH: 240
<212> TYPE: DNA
<213> ORGANISM: Homo sapiens

<400> SEQUENCE: 9
atggcccaca agcagatcta ctactcggac aagtacttcg acgaacacta cgagtaccgg 60
catgttatgt tacccagaga actttccaaa caagtaccta aaactcatct gatgtctgaa 120
gaggagtgga ggagacttgg tgtccaacag agtctaggct gggttcatta catgattcat 180
gagccagaac cacatattct tctctttaga cgacctcttc caaaagatca acaaaaatga 240

<210> SEQ ID NO 10
<211> LENGTH: 2025
<212> TYPE: DNA
<213> ORGANISM: Homo sapiens

<400> SEQUENCE: 10
atgaactccg gagccatgag gatccacagt aaaggacatt tccagggtgg aatccaagtc 60
aaaaatgaaa aaaacagacc atctctgaaa tctctgaaaa ctgataacag gccagaaaaa 120
tccaaatgta agccactttg gggaaaagta ttttaccttg acttaccttc tgtcaccata 180
tctgaaaaac ttcaaaagga cattaaggat ctgggagggc gagttgaaga atttctcagc 240
aaagatatca gttatcttat ttcaaataag aaggaagcta aatttgcaca aaccttgggt 300
cgaatttctc ctgtaccaag tccagaatct gcatatactg cagaaaccac ttcacctcat 360

-continued

```
cccagccatg atggaagttc atttaagtca ccagacacag tgtgtttaag cagaggaaaa    420

ttattagttg aaaaagctat caaggaccat gattttattc cttcaaatag tatattatca    480

aatgccttgt catggggagt aaaaattctt catattgatg acattagata ctacattgaa    540

caaaagaaaa aagagttgta tttactcaag aaatcaagta cttcagtaag agatgggggc    600

aaaagagttg gtagtggtgc acaaaaaaca agaacaggaa gactcaaaaa gccttttgta    660

aaggtggaag atatgagcca actttatagg ccattttatc ttcagctgac caatatgcct    720

tttataaatt attctattca gaagccctgc agtccatttg atgtagacaa gccatctagt    780

atgcaaaagc aaactcaggt taaactaaga atccaaacag atggcgataa gtatggtgga    840

acctcaattc aactccagtt gaaagagaag aagaaaaaag gatattgtga atgttgcttg    900

cagaaatatg aagatctaga aactcacctt ctaagtgagc aacacagaaa ctttgcacag    960

agtaaccagt atcaagttgt tgatgatatt gtatctaagt tagtttttga ctttgtggaa   1020

tatgaaaagg acacacctaa aaagaaaaga ataaaataca gtgttggatc cctttctcct   1080

gtttctgcaa gtgtcctgaa aaagactgaa caaaaggaaa aagtggaatt gcaacatatt   1140

tctcagaaag attgccagga agatgataca acagtgaagg agcagaattt cctgtataaa   1200

gagacccagg aaactgaaaa aaagctcctg tttatttcag agcccatccc ccacccttca   1260

aatgaattga gagggcttaa tgagaaaatg agtaataaat gttccatgtt aagtacagct   1320

gaagatgaca taagacagaa ttttacacag ctacctctac ataaaaaaca acaggaatgc   1380

attcttgaca tttccgaaca cacattaagt gaaaatgact tagaagaact aagggtagat   1440

cactataaat gtaacataca ggcatctgta catgtttctg atttcagtac agataatagt   1500

ggatctcaac caaaacagaa gtcagatact gtgcttttc cagcaaagga tctcaaggaa   1560

aaggaccttc attcaatatt tactcatgat tctggtctga taacaataaa cagttcacaa   1620

gagcacctaa ctgttcaggc aaaggctcca ttccatactc ctcctgagga acccaatgaa   1680

tgtgacttca agaatatgga tagtttacct tctggtaaaa tacatcgaaa agtgaaaata   1740

atattaggac gaaatagaaa agaaaatctg gaaccaaatg ctgaatttga taaaagaact   1800

gaatttatta cacaagaaga aaacagaatt tgtagttcac cggtacagtc tttactagac   1860

ttgtttcaga ctagtgaaga gaaatcagaa tttttgggtt tcacaagcta cacagaaaag   1920

agtggtatat gcaatgtttt agatatttgg gaagaggaaa attcagataa tctgttaaca   1980

gcgtttttct cgtccccttc aacttctaca tttactggct tttag                   2025
```

```
<210> SEQ ID NO 11
<211> LENGTH: 1449
<212> TYPE: DNA
<213> ORGANISM: Homo sapiens

<400> SEQUENCE: 11

atgcctccgt ctcctttaga cgacagggta gtagtggcac tatctaggcc cgtccgacct     60

caggatctca acctttgttt agactctagt taccttggct ctgccaaccc aggcagtaac    120

agccaccctc ctgtcatcgc caccaccgtt gtgtccctca aggctgcgaa tctgacgtat    180

atgccctcat ccagcggctc tgcccgctcg ctgaattgtg gatgcagcag tgccagctgc    240

tgcactgtgg caacctacga caaggacaat caggcccaaa cccaagccat tgccgctggc    300

accaccacca ctgccatcgg aacctctacc acctgccctg ctaaccagat ggtcaacaat    360

aatgagaata caggctctct aagtccatca agtggggtgg gcagccctgt gtcagggacc    420

cccaagcagc tagccagcat caaaataatc taccccaatg acttggcaaa gaagatgacc    480
```

```
aaatgcagca agagtcacct gccgagtcag ggccctgtca tcattgactg caggcccttc    540

atggagtaca acaagagtca catccaagga gctgtccaca ttaactgtgc cgataagatc    600

agccggcgga gactgcagca gggcaagatc actgtcctag acttgatttc ctgtagggaa    660

ggcaaggact ctttcaagag gatcttttcc aaagaaatta tagtttatga tgagaatacc    720

aatgaaccaa gccgagtgat gccctcccag ccacttcaca tagtcctcga gtccctgaag    780

agagaaggca aagaacctct ggtgttgaaa ggtggactta gtagttttaa gcagaaccat    840

gaaaacctct gtgacaactc cctccagctc caagagtgcc gggaggtggg gggcggcgca    900

tccgcggcct cgagcttgct acctcagccc atccccacca cccctgacat cgagaacgct    960

gagctcaccc ccatcttgcc cttcctgttc cttggcaatg agcaggatgc tcaggacctg   1020

gacaccatgc agcggctgaa catcggctac gtcatcaacg tcaccactca tcttcccctc   1080

taccactatg agaaaggcct gttcaactac aagcggctgc cagccactga cagcaacaag   1140

cagaacctgc ggcagtactt tgaagaggct tttgagttca ttgaggaagc tcaccagtgt   1200

gggaaggggc ttctcatcca ctgccaggct ggggtgtccc gctccgccac catcgtcatc   1260

gcttacttga tgaagcacac tcggatgacc atgactgatg cttataaatt tgtcaaaggc   1320

aaacgaccaa ttatctcccc aaaccttaac ttcatggggc agttgctaga gttcgaggaa   1380

gacctaaaca acggtgtgac accgagaatc cttacaccaa agctgatggg cgtggagacg   1440

gttgtgtga                                                           1449
```

<210> SEQ ID NO 12
<211> LENGTH: 2754
<212> TYPE: DNA
<213> ORGANISM: Homo sapiens

<400> SEQUENCE: 12

```
atgattgcct cgcatctgct tgcctacttc ttcacggagc tcaaccatga ccaagtgcag     60

aaggttgacc agtatctcta ccacatgcgc ctctctgatg agaccctctt ggagatctct    120

aagcggttcc gcaaggagat ggagaaaggg cttggagcca ccactcaccc tactgcagca    180

gtgaagatgc tgcccacctt tgtgaggtcc actccagatg ggacagaaca cggagagttc    240

ctggctctgg atcttggagg gaccaacttc cgtgtgcttt gggtgaaagt aacggacaat    300

gggctccaga aggtggagat ggagaatcag atctatgcca tccctgagga catcatgcga    360

ggcagtggca cccagctgtt tgaccacatt gccgaatgcc tggctaactt catggataag    420

ctacaaatca aagacaagaa gctcccactg ggttttacct tctcgttccc ctgccaccag    480

actaaactag acgagagttt cctggtctca tggaccaagg gattcaagtc cagtggagtg    540

gaaggcagag acgttgtggc tctgatccgg aaggccatcc agaggagagg ggactttgat    600

atcgacattg tggctgtggt gaatgacaca gttgggacca tgatgacctg tggttatgat    660

gaccacaact gtgagattgg tctcattgtg ggcacgggca gcaacgcctg ctacatggaa    720

gagatgcgcc acatcgacat ggtggaaggc gatgaggggc ggatgtgtat caatatggag    780

tggggggcct tcggggacga tggctcgctc aacgacattc gcactgagtt tgaccaggag    840

attgacatgg gctcactgaa cccgggaaag caactgtttg agaagatgat cagtgggatg    900

tacatggggg agctggtgag gcttatcctg gtgaagatgg ccaaggagga gctgctcttt    960

gggggggaagc tcagcccaga gcttctcaac accggtcgct ttgagaccaa agacatctca   1020

gacattgaag gggagaagga tggcatccgg aaggcccgtg aggtcctgat gcggttgggc   1080
```

-continued

```
ctggacccga ctcaggagga ctgcgtggcc actcaccgga tctgccagat cgtgtccaca   1140

cgctccgcca gcctgtgcgc agccaccctg gccgccgtgc tgcagcgcat caaggagaac   1200

aaaggcgagg agcggctgcg ctctactatt ggggtcgacg gttccgtcta caagaaacac   1260

ccccattttg ccaagcgtct acataagacc gtgcggcggc tggtgcccgg ctgcgatgtc   1320

cgcttcctcc gctccgagga tggcagtggc aaaggtgcag ccatggtgac agcagtggct   1380

taccggctgg ccgatcaaca ccgtgcccgc cagaagacat tagagcatct gcagctgagc   1440

catgaccagc tgctggaggt caagaggagg atgaaggtag aaatggagcg aggtctgagc   1500

aaggagactc atgccagtgc cccgtcaag atgctgccca cctacgtgtg tgctaccccg   1560

gacggcacag agaaagggga cttcttggcc ttggaccttg gaggaacaaa tttccgggtc   1620

ctgctggtcc gtgttcggaa tgggaagtgg ggtggagtgg agatgcacaa caagatctac   1680

gccatcccgc aggaggtcat gcacggcacc ggggacgagc tctttgacca cattgtccag   1740

tgcatcgcgg acttcctcga gtacatgggc atgaagggcg tgtccctgcc tctgggtttt   1800

accttctcct tcccctgcca gcagaacagc ctggacgaga gcatcctcct caagtggaca   1860

aaaggcttca aggcatctgg ctgcgagggc gaggacgtgg tgaccctgct gaaggaagcg   1920

atccaccggc gagaggagtt tgacctggat gtggttgctg tggtgaacga cacagtcgga   1980

actatgatga cctgtggctt tgaagaccct cactgtgaag ttggcctcat tgttggcacg   2040

ggcagcaatg cctgctacat ggaggagatg cgcaacgtgg aactggtgga aggagaagag   2100

gggcggatgt gtgtgaacat ggaatggggg gccttcgggg acaatggatg cctagatgac   2160

ttccgcacag aatttgatgt ggctgtggat gagctttcac tcaaccccgg caagcagagg   2220

ttcgagaaaa tgatcagtgg aatgtacctg ggtgagattg tccgtaacat tctcatcgat   2280

ttcaccaagc gtggactact cttccgaggc cgcatctcag agcggctcaa gacaaggggc   2340

atctttgaaa ccaagttctt gtctcagatt gagagtgact gcctggccct gctgcaagtc   2400

cgagccatcc tgcaacactt agggcttgag agcacctgtg acgacagcat cattgttaag   2460

gaggtgtgca ctgtggtggc ccggcgggca gcccagctct gtggcgcagg catggccgct   2520

gtggtggaca ggatacgaga aaaccgtggg ctggacgctc tcaaagtgac agtgggtgtg   2580

gatgggaccc tctacaagct acatcctcac tttgccaaag tcatgcatga gacagtgaag   2640

gacctggctc cgaaatgtga tgtgtctttc ctgcagtcag aggatggcag cgggaagggg   2700

gcggcgctca tcactgctgt ggcctgccgc atccgtgagg ctggacagcg atag         2754
```

<210> SEQ ID NO 13
<211> LENGTH: 1446
<212> TYPE: DNA
<213> ORGANISM: Homo sapiens

<400> SEQUENCE: 13

```
atggaggatc cctccgagcc cgaccggttg gcgtccgcgg acggcgggag cccggaggag     60

gaggaggatg gggagcggga gccgctgcta ccgcggatcg cctgggccca cccgcggaga    120

ggcgccccag gcagcgccgt gaggctgctg gacgctgccg gggaggaggg cgaggccggc    180

gacgaggagc tgcccctccc gcccggggac gtgggggtct cccggagttc gtccgccgag    240

ctggaccgga gccgccccgc ggtttcagta actattggta cttcagagat gaatgcattc    300

ttggatgacc cagaatttgc cgatattatg ctgagagcag agcaagcaat agaagttgga    360

atttttccag aaagaatctc tcaaggttca agtggaagtt actttgtgaa ggatcctaag    420

aggaaaatta ttggtgtgtt taaacccaaa tcagaagagc cttatggtca actcaatcca    480
```

```
aaatggacca aatatgtcca taaggtctgc tgcccttgct gctttggccg aggctgcctg    540

attcctaatc aggggtacct ttccgaagcg ggtgcctatc ttgtggacaa caagcttcat    600

ctgagcattg tacctaaaac aaaggtggtt tggcttgtca gtgagacatt taactataat    660

gcgattgacc gtgcaaaatc aagaggcaaa aagtatgctt tagaaaaagt gccaaaagtg    720

ggtagaaagt ttcataggat aggactccct cctaagattg gttcctttca gttatttgtt    780

gaaggttaca aggaggctga atattggctt aggaaatttg aagctgaccc tttgcctgag    840

aatattagaa aacaatttca gtcacaattt gaaagattag ttattttgga ttacatcatc    900

agaaatacag acaggggcaa tgataattgg ttagtcagat acgaaaagca gaaatgtgaa    960

aaggaaattg accataagga atcaaaatgg attgatgatg aagaattcct tattaaaata   1020

gctgcaattg ataatggtct agcatttcct tttaaacatc ctgatgaatg gagagcatat   1080

ccatttcact gggcttggct tcctcaagca aaagttccct tttctgaaga aataagaaat   1140

ttgattctac catatatttc tgacatgaac tttgtgcaag atttatgtga agatctctat   1200

gaacttttta agactgacaa aggatttgac aaagccactt ttgaaagtca gatgtctgtg   1260

atgaggggtc agatcttaaa ccttactcag gcattgagag acgggaagag tcctttccag   1320

ctagtacaga taccttgtgt gattgtggaa cgcagtcaag gtggaagtca gggtcggatt   1380

gtccacctga gcaattcctt tacccagact gtcaattgca ggaagccatt tttttcctcc   1440

tggtag                                                              1446
```

<210> SEQ ID NO 14
<211> LENGTH: 1005
<212> TYPE: DNA
<213> ORGANISM: Homo sapiens

<400> SEQUENCE: 14

```
atgtctcagt cgaaaggcaa gaagcgaaac cctggcctta aaattccaaa agaagcattt     60

gaacaacctc agaccagttc cacaccacct cgagatttag actccaaggc ttgcatttct    120

attggaaatc agaactttga ggtgaaggca gatgacctgg agcctataat ggaactggga    180

cgaggtgcgt acggggtggt ggagaagatg cggcacgtgc ccagcgggca gatcatggca    240

gtgaagcgga tccgagccac agtaaatagc caggaacaga aacggctact gatggatttg    300

gatatttcca tgaggacggt ggactgtcca ttcactgtca ccttttatgg cgcactgttt    360

cgggagggtg atgtgtggat ctgcatggag ctcatggata catcactaga taaattctac    420

aaacaagtta ttgataaagg ccagacaatt ccagaggaca tcttagggaa aatagcagtt    480

tctattgtaa aagcattaga acatttacat agtaagctgt ctgtcattca cagagacgtc    540

aagccttcta atgtactcat caatgctctc ggtcaagtga agatgtgcga ttttggaatc    600

agtggctact tggtggactc tgttgctaaa acaattgatg caggttgcaa accatacatg    660

gcccctgaaa gaataaaccc agagctcaac cagaagggat acagtgtgaa gtctgacatt    720

tggagtctgg gcatcacgat gattgagttg gccatccttc gatttcccta tgattcatgg    780

ggaactccat ttcagcagct caaacaggtg gtagaggagc catcgccaca actcccagca    840

gacaagttct ctgcagagtt tgttgacttt acctcacagt gcttaaagaa gaattccaaa    900

gaacggccta catacccaga gctaatgcaa catccatttt tcaccctaca tgaatccaaa    960

ggaacagatg tggcatcttt tgtaaaactg attcttggag actaa                   1005
```

<210> SEQ ID NO 15

<211> LENGTH: 1833
<212> TYPE: DNA
<213> ORGANISM: Homo sapiens

<400> SEQUENCE: 15
atgaaagatt atgatgaact tctcaaatat tatgaattac atgaaactat tgggacaggt 60
ggctttgcaa aggtcaaact tgcctgccat atccttactg gagagatggt agctataaaa 120
atcatggata aaaacacact agggagtgat ttgccccgga tcaaaacgga gattgaggcc 180
ttgaagaacc tgagacatca gcatatatgt caactctacc atgtgctaga gacagccaac 240
aaaatattca tggttcttga gtactgccct ggaggagagc tgtttgacta tataatttcc 300
caggatcgcc tgtcagaaga ggagacccgg gttgtcttcc gtcagatagt atctgctgtt 360
gcttatgtgc acagccaggg ctatgctcac agggacctca agccagaaaa tttgctgttt 420
gatgaatatc ataaattaaa gctgattgac tttggtctct gtgcaaaacc caagggtaac 480
aaggattacc atctacagac atgctgtggg agtctggctt atgcagcacc tgagttaata 540
caaggcaaat catatcttgg atcagaggca gatgtttgga gcatgggcat actgttatat 600
gttcttatgt gtggatttct accatttgat gatgataatg taatggcttt atacaagaag 660
attatgagag gaaaatatga tgttcccaag tggctctctc ccagtagcat tctgcttctt 720
caacaaatgc tgcaggtgga cccaaagaaa cggatttcta tgaaaaatct attgaaccat 780
ccctggatca tgcaagatta caactatcct gttgagtggc aaagcaagaa tccttttatt 840
cacctcgatg atgattgcgt aacagaactt tctgtacatc acagaaacaa caggcaaaca 900
atggaggatt taatttcact gtggcagtat gatcacctca cggctaccta tcttctgctt 960
ctagccaaga aggctcgggg aaaaccagtt cgtttaaggc tttcttcttt ctcctgtgga 1020
caagccagtg ctaccccatt cacagacatc aagtttacca agtactggac agaatcaaat 1080
ggggtggaat ctaaatcatt aactccagcc ttatgcagaa cacctgcaaa taaattaaag 1140
aacaaagaaa atgtatatac tcctaagtct gctgtaaaga atgaagagta ctttatgttt 1200
cctgagccaa agactccagt taataagaac cagcataaga gagaaatact cactacgcca 1260
aatcgttaca ctacaccctc aaaagctaga aaccagtgcc tgaaagaaac tccaattaaa 1320
ataccagtaa attcaacagg aacagacaag ttaatgacag gtgtcattag ccctgagagg 1380
cggtgccgct cagtggaatt ggatctcaac caagcacata tggaggagac tccaaaaaga 1440
aagggagcca aagtgtttgg gagccttgaa agggggttgg ataaggttat cactgtgctc 1500
accaggagca aaaggaaggg ttctgccaga gacgggccca gaagactaaa gcttcactat 1560
aacgtgacta caactagatt agtgaatcca gatcaactgt tgaatgaaat aatgtctatt 1620
cttccaaaga agcatgttga ctttgtacaa aagggttata cactgaagtg tcaaacacag 1680
tcagattttg ggaaagtgac aatgcaattt gaattagaag tgtgccagct tcaaaaaccc 1740
gatgtggtgg gtatcaggag gcagcggctt aagggcgatg cctgggttta caaaagatta 1800
gtggaagaca tcctatctag ctgcaaggta taa 1833

<210> SEQ ID NO 16
<211> LENGTH: 1338
<212> TYPE: DNA
<213> ORGANISM: Homo sapiens

<400> SEQUENCE: 16
atgccttccc gggctgagga ctatgaagtg ttgtacacca ttggcacagg ctcctacggc 60
cgctgccaga agatccggag gaagagtgat ggcaagatat tagtttggaa agaacttgac 120

```
tatggctcca tgacagaagc tgagaaacag atgcttgttt ctgaagtgaa tttgcttcgt    180
gaactgaaac atccaaacat cgttcgttac tatgatcgga ttattgaccg gaccaataca    240
acactgtaca ttgtaatgga atattgtgaa ggaggggatc tggctagtgt aattacaaag    300
ggaaccaagg aaaggcaata cttagatgaa gagtttgttc ttcgagtgat gactcagttg    360
actctggccc tgaaggaatg ccacagacga agtgatggtg gtcataccgt attgcatcgg    420
gatctgaaac cagccaatgt tttcctggat ggcaagcaaa acgtcaagct tggagacttt    480
gggctagcta gaatattaaa ccatgacacg agttttgcaa aaacatttgt tggcacacct    540
tattacatgt ctcctgaaca aatgaatcgc atgtcctaca atgagaaatc agatatctgg    600
tcattgggct gcttgctgta tgagttatgt gcattaatgc ctccatttac agcttttagc    660
cagaaagaac tcgctgggaa aatcagagaa ggcaaattca ggcgaattcc ataccgttac    720
tctgatgaat tgaatgaaat tattacgagg atgttaaact taaaggatta ccatcgacct    780
tctgttgaag aaattcttga gaacccttta atagcagatt tggttgcaga cgagcaaaga    840
agaaatcttg agagaagagg gcgacaatta ggagagccag aaaaatcgca ggattccagc    900
cctgtattga gtgagctgaa actgaaggaa attcagttac aggagcgaga gcgagctctc    960
aaagcaagag aagaaagatt ggagcagaaa gaacaggagc tttgtgttcg tgagagacta   1020
gcagaggaca aactggctag agcagaaaat ctgttgaaga actacagctt gctaaaggaa   1080
cggaagttcc tgtctctggc aagtaatcca gaacttctta atcttccatc ctcagtaatt   1140
aagaagaaag ttcatttcag tggggaaagt aaagagaaca tcatgaggag tgagaattct   1200
gagagtcagc tcacatctaa gtccaagtgc aaggacctga agaaaaggct tcacgctgcc   1260
cagctgcggg ctcaagccct gtcagatatt gagaaaaatt accaactgaa aagcagacag   1320
atcctgggca tgcgctag                                                 1338

<210> SEQ ID NO 17
<211> LENGTH: 2478
<212> TYPE: DNA
<213> ORGANISM: Homo sapiens

<400> SEQUENCE: 17

atggatgtct ctctttgccc agccaagtgt agtttctggc ggattttctt gctgggaagc     60
gtctggctgg actatgtggg ctccgtgctg gcttgccctg caaattgtgt ctgcagcaag    120
actgagatca attgccggcg gccggacgat gggaacctct tccccctcct ggaagggcag    180
gattcaggga acagcaatgg gaacgccagt atcaacatca cggacatctc aaggaatatc    240
acttccatac acatagagaa ctggcgcagt cttcacacgc tcaacgccgt ggacatggag    300
ctctacaccg gacttcaaaa gctgaccatc aagaactcag gacttcggag cattcagccc    360
agagcctttg ccaagaaccc ccatttgcgt tatataaacc tgtcaagtaa ccggctcacc    420
acactctcgt ggcagctctt ccagacgctg agtcttcggg aattgcagtt ggagcagaac    480
tttttcaact gcagctgtga catccgctgg atgcagctct ggcaggagca gggggaggcc    540
aagctcaaca gccagaacct ctactgcatc aacgctgatg gctcccagct tcctctcttc    600
cgcatgaaca tcagtcagtg tgaccttcct gagatcagcg tgagccacgt caacctgacc    660
gtacgagagg gtgacaacgc tgttatcact tgcaatggct ctggatcacc ccttcctgat    720
gtggactgga tagtcactgg gctgcagtcc atcaacactc accagaccaa tctgaactgg    780
accaatgttc atgccatcaa cttgacgctg gtgaatgtga cgagtgagga caatggcttc    840
```

-continued accctgacgt gcattgcaga gaacgtggtg ggcatgagca atgccagtgt tgccctcact 900
gtctactatc ccccacgtgt ggtgagcctg gaggagcctg agctgcgcct ggagcactgc 960
atcgagtttg tggtgcgtgg caaccccccca ccaacgctgc actggctgca caatgggcag 1020
cctctgcggg agtccaagat catccatgtg gaatactacc aagagggaga gatttccgag 1080
ggctgcctgc tcttcaacaa gcccacccac tacaacaatg gcaactatac cctcattgcc 1140
aaaaacccac tgggcacagc caaccagacc atcaatggcc acttcctcaa ggagcccttt 1200
ccagagagca cggataactt tatcttgttt gacgaagtga gtcccacacc tcctatcact 1260
gtgacccaca aaccagaaga agacactttt ggggtatcca tagcagttgg acttgctgct 1320
tttgcctgtg tcctgttggt ggttctcttc gtcatgatca acaaatatgg tcgacggtcc 1380
aaatttggaa tgaagggtcc cgtggctgtc atcagtggtg aggaggactc agccagccca 1440
ctgcaccaca tcaaccacgg catcaccacg ccctcgtcac tggatgccgg gcccgacact 1500
gtggtcattg gcatgactcg catccctgtc attgagaacc cccagtactt ccgtcaggga 1560
cacaactgcc acaagccgga cacgtatgtg cagcacatta agaggagaga catcgtgctg 1620
aagcgagaac tgggtgaggg agcctttgga aaggtcttcc tggccgagtg ctacaacctc 1680
agcccgacca aggacaagat gcttgtggct gtgaaggccc tgaaggatcc caccctggct 1740
gcccggaagg atttccagag ggaggccgag ctgctcacca acctgcagca tgagcacatt 1800
gtcaagttct atggagtgtg cggcgatggg gacccccctca tcatggtctt tgaatacatg 1860
aagcatggag acctgaataa gttcctcagg gcccatgggc cagatgcaat gatccttgtg 1920
gatggacagc cacgccaggc caagggtgag ctggggctct cccaaatgct ccacattgcc 1980
agtcagatcg cctcgggtat ggtgtacctg gcctcccagc actttgtgca ccgagacctg 2040
gccaccagga actgcctggt tggagcgaat ctgctagtga agattgggga cttcggcatg 2100
tccagagatg tctacagcac ggattattac agggtgggag gacacaccat gctccccatt 2160
cgctggatgc ctcctgaaag catcatgtac cggaagttca ctacagagag tgatgtatgg 2220
agcttcgggg tgatcctctg ggagatcttc acctatggaa agcagccatg gttccaactc 2280
tcaaacacgg aggtcattga gtgcattacc caaggtcgtg ttttggagcg gccccgagtc 2340
tgccccaaag aggtgtacga tgtcatgctg gggtgctggc agagggaacc acagcagcgg 2400
ttgaacatca aggagatcta caaaatcctc catgctttgg ggaaggccac cccaatctac 2460
ctggacattc ttggctag 2478

<210> SEQ ID NO 18
<211> LENGTH: 1575
<212> TYPE: DNA
<213> ORGANISM: Homo sapiens

<400> SEQUENCE: 18
atgtctgata acggagaact ggaagataag cctccagcac ctcctgtgcg aatgagcagc 60
accatcttta gcactggagg caaagaccct ttgtcagcca atcacagttt gaaacctttg 120
ccctctgttc cagaagagaa aaagcccagg cataaaatca tctccatatt ctcaggcaca 180
gagaaaggaa gtaaaaagaa agaaaaggaa cggccagaaa tttctcctcc atctgatttt 240
gagcacacca tccatgttgg ctttgatgct gttactggag aattcactgg catgccagaa 300
cagtgggctc gattactaca gacctccaat atcaccaaac tagagcaaaa gaagaatcct 360
caggctgtgc tggatgtcct aaagttctac gactccaaca cagtgaagca gaaatatctg 420
agctttactc ctcctgagaa agatggcttt ccttctggaa caccagcact gaatgccaag 480

```
ggaacagaag cacccgcagt agtgacagag gaggaggatg atgatgaaga gactgctcct    540

cccgttattg ccccgcgacc ggatcatacg aaatcaattt acacacggtc tgtaattgac    600

cctgttcctg caccagttgg tgattcacat gttgatggtg ctgccaagtc tttagacaaa    660

cagaaaaaga agactaagat gacagatgaa gagattatgg agaaattaag aactatcgtg    720

agcataggtg accctaagaa aaaatataca agatatgaaa aaattggaca aggggcttct    780

ggtacagttt tcactgctac tgacgttgca ctgggacagg aggttgctat caaacaaatt    840

aatttacaga aacagccaaa gaaggaactg atcattaacg agattctggt gatgaaagaa    900

ttgaaaaatc ccaacatcgt taactttttg gacagttacc tggtaggaga tgaattgttt    960

gtggtcatgg aataccttgc tggggggtca ctcactgatg tggtaacaga aacgtgcatg   1020

gatgaagcac agattgctgc tgtatgcaga gagtgtttac aggcattgga gtttttacat   1080

gctaatcaag tgatccacag agacatcaaa agtgacaatg tacttttggg aatggaagga   1140

tctgttaagc tcactgactt tggtttctgt gcccagatca cccctgagca gagcaaacgc   1200

agtaccatgg tcggaacgcc atactggatg gcaccagagg tggttacacg gaaagcttat   1260

ggccctaaag tcgacatatg gtctctgggt atcatggcta ttgagatggt agaaggagag   1320

cctccatacc tcaatgaaaa tcccttgagg gccttgtacc taatagcaac taatggaacc   1380

ccagaacttc agaatccaga gaaactttcc ccaatatttc gggatttctt aaatcgatgt   1440

ttggaaatgg atgtggaaaa aaggggttca gccaaagaat tattacagca tcctttcctg   1500

aaactggcca aaccgttatc tagcttgaca ccactgatca tggcagctaa agaagcaatg   1560

aagagtaacc gttaa                                                    1575
```

<210> SEQ ID NO 19
<211> LENGTH: 969
<212> TYPE: DNA
<213> ORGANISM: Homo sapiens

<400> SEQUENCE: 19

```
atggaaggga tcagtaattt caagacacca agcaaattat cagaaaaaaa gaaatctgta     60

ttatgttcaa ctccaactat aaatatcccg gcctctccgt ttatgcagaa gcttggcttt    120

ggtactgggg taaatgtgta cctaatgaaa agatctccaa gaggtttgtc tcattctcct    180

tgggctgtaa aaaagattaa tcctatatgt aatgatcatt atcgaagtgt gtatcaaaag    240

agactaatgg atgaagctaa gattttgaaa agccttcatc atccaaacat tgttggttat    300

cgtgctttta ctgaagccaa tgatggcagt ctgtgtcttg ctatggaata tggaggtgaa    360

aagtctctaa atgacttaat agaagaacga tataaagcca gccaagatcc ttttccagca    420

gccataattt taaaagttgc tttgaatatg gcaagagggt taaagtatct gcaccaagaa    480

aagaaactgc ttcatggaga cataaagtct tcaaatgttg taattaaagg cgattttgaa    540

acaattaaaa tctgtgatgt aggagtctct ctaccactgg atgaaaatat gactgtgact    600

gaccctgagg cttgttacat tggcacagag ccatggaaac ccaaagaagc tgtggaggag    660

aatggtgtta ttactgacaa ggcagacata tttgcctttg gccttacttt gtgggaaatg    720

atgactttat cgattccaca cattaatctt tcaaatgatg atgatgatga agataaaact    780

tttgatgaaa gtgattttga tgatgaagca tactatgcag cgttgggaac taggccacct    840

attaatatgg aagaactgga tgaatcatac cagaaagtaa ttgaactctt ctctgtatgc    900

actaatgaag accctaaaga tcgtccttct gctgcacaca ttgttgaagc tctggaaaca    960
```

-continued

```
gatgtctag                                                           969


<210> SEQ ID NO 20
<211> LENGTH: 2331
<212> TYPE: DNA
<213> ORGANISM: Homo sapiens

<400> SEQUENCE: 20

atgtgcgggt atgaacgctg ccgtccgtgc cgtggtgcgc atgggtatct acgtgggggc     60

caaggtgtac ttcatctacg agggctacca gggcatggtg gacggaggct caaacatcgc    120

agaggccgac tgggagagtg tctccagcat cctgcaagtg gtgctgtaag ggtgactgg    180

agggagaagc ctggctgctg gtcacaccgc ttcccttgtc ctggccggca tgctctggtg    240

ggcgggacga tcattggcag tgcgcggtgc caggccttcc gcacgcggga aggccgcctg    300

aaggctgctt gcaacctgct gcagcgcggc atcaccaacc tgtgtgtgat cggcggggac    360

gggagcctca ccggggccaa cctcttccgg aaggagtgga gtgggctgct ggaggagctg    420

gccaggaacg gccagatcga taaggaggcc gtgcagaagt acgcctacct caacgtggtg    480

ggcatggtgg gctccatcga caatgatttc tgcggcaccg acatgaccat cggcacggac    540

tccgccctgc acaggatcat cgaggtcgtc gacgccatca tgaccacggc ccagagccac    600

cagaggacct tcgttctgga ggtgatggga cgacactgtg ggtacctggc cctggtgagt    660

gccttggcct gcggtgcgga ctgggtgttc cttccagaat ctccaccaga ggaaggctgg    720

gaggagcaga tgtgtgtcaa actctcggag aaccgtgccc ggaaaaaaag gctgaatatt    780

attattgtgg ctgaaggagc aattgatacc caaaataaac ccatcacctc tgagaaaatc    840

aaagagcttg tcgtcacgca gctgggctat gacacacgtg tgaccatcct cgggcacgtg    900

cagagaggag ggacccctte ggcattcgac aggatcttgg ccagccgcat gggagtggag    960

gcagtcatcg ccttgctaga ggccaccccg gacaccccag cttgcgtcgt gtcactgaac   1020

gggaaccacg ccgtgcgcct gccgctgatg gagtgcgtgc agatgactca ggatgtgcag   1080

aaggcgatgg acgagaggag atttcaagat gcggttcgac tccgagggag gagctttgcg   1140

ggcaacctga acacctacaa gcgacttgcc atcaagctgc cggatgatca gatcccaaag   1200

accaattgca acgtagctgt catcaacgtg ggggcacccg cggctgggat gaacgcagcc   1260

gtacgctcag ctgtgcgcgt gggcattgcc gacggccaca ggatgctcgc catctatgat   1320

ggctttgacg gcttcgccaa gggccagatc aaagaaatcg gctggacaga tgtcgggggc   1380

tggaccggcc aaggaggctc cattcttggg acaaaacgcg ttctcccggg gaagtacttg   1440

gaagagatcg ccacacagat gcgcacgcac agcatcaacg cgctgctgat catcggtgga   1500

ttcgaggcct acctgggact cctggagctg tcagccgccc gggagaagca cgaggagttc   1560

tgtgtcccca tggtcatggt tcccgctact gtgtccaaca atgtgccggg ttccgatttc   1620

agcatcgggg cagacaccgc cctgaacact atcaccgaca cctgcgaccg catcaagcag   1680

tccgccagcg gaaccaagcg gcgcgtgttc atcatcgaga ccatgggcgg ctactgtggc   1740

tacctggcca acatgggggg gctcgcggcc ggagctgatg ccgcatacat tttcgaagag   1800

cccttcgaca tcagggatct gcagtccaac gtggagcacc tgacggagaa aatgaagacc   1860

accatccaga gaggccttgt gctcagaaat gagagctgca gtgaaaacta caccaccgac   1920

ttcatttacc agctgtattc agaagagggc aaaggcgtgt ttgactgcag gaagaacgtg   1980

ctgggtcaca tgcagcaggg tggggcaccc tctccatttg atagaaactt tggaaccaaa   2040

atctctgcca gagctatgga gtggatcact gcaaaactca aggaggcccg gggcagagga   2100
```

```
aaaaaattta ccaccgatga ttccatttgt gtgctgggaa taagcaaaag aaacgttatt   2160

tttcaacctg tggcagagct gaagaagcaa acggattttg agcacaggat tcccaaagaa   2220

cagtggtggc tcaagctacg gcccctcatg aaaatcctgg ccaagtacaa ggccagctat   2280

gacgtgtcgg actcaggcca gctggaacat gtgcagccct ggagtgtctg a            2331
```

<210> SEQ ID NO 21
<211> LENGTH: 2913
<212> TYPE: DNA
<213> ORGANISM: Homo sapiens

<400> SEQUENCE: 21

```
atggcgacct gcatcgggga gaagatcgag gattttaaag ttggaaatct gcttggtaaa     60

ggatcatttg ctggtgtcta cagagctgag tccattcaca ctggtttgga agttgcaatc    120

aaaatgatag ataagaaagc catgtacaaa gcaggaatgg tacagagagt ccaaaatgag    180

gtgaaaatac attgccaatt gaaacatcct tctatcttgg agctttataa ctattttgaa    240

gatagcaatt atgtgtatct ggtattagaa atgtgccata atggagaaat gaacaggtat    300

ctaaagaata gagtgaaacc cttctcagaa aatgaagctc gacacttcat gcaccagatc    360

atcacaggga tgttgtatct tcattctcat ggtatactac accgggacct cacactttct    420

aacctcctac tgactcgtaa tatgaacatc aagattgctg attttgggct ggcaactcaa    480

ctgaaaatgc cacatgaaaa gcactataca ttatgtggaa ctcctaacta catttcacca    540

gaaattgcca ctcgaagtgc acatggcctt gaatctgatg tttggtccct gggctgtatg    600

ttttatacat tacttatcgg gagaccaccc ttcgacactg acacagtcaa gaacacatta    660

aataaagtag tattggcaga ttatgaaatg ccatcttttt tgtcaataga ggccaaggac    720

cttattcacc agttacttcg tagaaatcca gcagatcgtt taagtctgtc ttcagtattg    780

gaccatcctt ttatgtcccg aaattcttca acaaaaagta aagatttagg aactgtggaa    840

gactcaattg atagtgggca tgccacaatt tctactgcaa ttacagcttc ttccagtacc    900

agtataagtg gtagtttatt tgacaaaaga agacttttga ttggtcagcc actcccaaat    960

aaaatgactg tatttccaaa gaataaaagt tcaactgatt tttcttcttc aggagatgga   1020

aacagttttt atactcagtg ggaaatcaa gaaaccagta atagtggaag ggaagagta     1080

attcaagatg cagaagaaag gccacattct cgataccttc gtagagctta ttcctctgat   1140

agatctggca cttctaatag tcagtctcaa gcaaaaacat atacaatgga acgatgtcac   1200

tcagcagaaa tgctttcagt gtccaaaaga tcaggaggag gtgaaaatga agagaggtac   1260

tcacccacag acaacaatgc caacattttt aacttcttta aagaaaagac atccagtagt   1320

tctggatctt ttgaaagacc tgataacaat caagcactct ccaatcatct ttgtccagga   1380

aaaactcctt ttccatttgc agacccgaca cctcagactg aaaccgtaca acagtggttt   1440

gggaatctgc aaataaatgc tcatttaaga aaaactactg aatatgacag catcagccca   1500

aaccgggact tccagggcca tccagatttg cagaaggaca catcaaaaaa tgcctggact   1560

gatacaaaag tcaaaaagaa ctctgatgct tctgataatg cacattctgt aaaacagcaa   1620

aataccatga aatatatgac tgcacttcac agtaaacctg agataatcca acaagaatgt   1680

gtttttggct cagatcctct ttctgaacag agcaagacta ggggtatgga gccaccatgg   1740

ggttatcaga atcgtacatt aagaagcatt acatctccgt tggttgctca caggttaaaa   1800

ccaatcagac agaaaaccaa aaaggctgtg gtgagcatac ttgattcaga ggaggtgtgt   1860
```

-continued

```
gtggagcttg taaaggagta tgcatctcaa gaatatgtga aagaagttct tcagatatct   1920

agtgatggaa atacgatcac tatttattat ccaaatggtg gtagaggttt tcctcttgct   1980

gatagaccac cctcacctac tgacaacatc agtaggtaca gctttgacaa tttaccagaa   2040

aaatactggc gaaaatatca atatgcttcc aggtttgtac agcttgtaag atctaaatct   2100

cccaaaatca cttattttac aagatatgct aaatgcattt tgatggagaa ttctcctggt   2160

gctgattttg aggtttggtt ttatgatggg gtaaaaatac acaaaacaga agatttcatt   2220

caggtgattg aaaagacagg gaagtcttac actttaaaaa gtgaaagtga agttaatagc   2280

ttgaaagagg agataaaaat gtatatggac catgctaatg agggtcatcg tatttgttta   2340

gcactggaat ccataatttc agaagaggaa aggaaaacta ggagtgctcc ctttttccca   2400

ataatcatag gaagaaaacc tggtagtact agttcaccta aggccttatc acctcctcct   2460

tctgtggatt caaattaccc aacgagagag agagcatctt tcaacagaat ggtcatgcat   2520

agtgctgctt ctccaacaca ggcaccaatc cttaatccct ctatggttac aaatgaagga   2580

cttggtctta caactacagc ttctggaaca gacatctctt ctaatagtct aaaagattgt   2640

cttcctaaat cagcacaact tttgaaatct gtttttgtga aaaatgttgg ttgggctaca   2700

cagttaacta gtggagctgt gtgggttcag tttaatgatg ggtcccagtt ggttgtgcag   2760

gcaggagtgt cttctatcag ttatacctca ccaaatggtc aaacaactag gtatggagaa   2820

aatgaaaaat taccagacta catcaaacag aaattacagt gtctgtcttc catccttttg   2880

atgttttcta atccgactcc taattttcat tga                                2913
```

<210> SEQ ID NO 22
<211> LENGTH: 4338
<212> TYPE: DNA
<213> ORGANISM: Homo sapiens

<400> SEQUENCE: 22

```
atgcggaggt tactggaacc gtgttggtgg attttgttcc tgaaaatcac cagttccgtg     60

ctccattatg tcgtgtgctt ccccgcgttg acagaaggct acgttggggc cctgcacgag    120

aatagacacg gcagcgcagt gcagatccgc aggcgcaagg cttcaggcga cccgtactgg    180

gcctactctg gtgcctatgg tcctgagcac tgggtcacgt ctagtgtcag ctgtgggggc    240

cgtcaccagt ctcctattga cattttagac cagtatgcgc gtgttgggga agaataccag    300

gaactgcaac tcgatggctt cgacaatgag tcttctaaca aaacctggat gaaaaacaca    360

gggaaaacag tcgccatcct tctgaaagac gactattttg tcagtggagc tggtctacct    420

ggcagattca aagctgagaa ggtggaattt cactggggcc acagcaatgg ctcagcgggc    480

tctgaacaca gcatcaatgg caggaggttt cctgttgaga tgcagatttt cttttacaat    540

ccagatgact ttgacagctt tcaaaccgca atttctgaga acagaataat cggagccatg    600

gccatatttt ttcaagtcag tccgagggac aattctgcac tggatcctat tatccacggg    660

ttgaagggtg tcgtacatca tgagaaggag acctttctgg atcctttcgt cctccgggac    720

ctcctgcctg catccctggg cagctattat cggtacacag gttccttgac cacaccaccg    780

tgtagcgaaa tagtggagtg gatagtcttc cggagacccg tccccatctc ttaccatcag    840

cttgaggctt tttattccat cttcaccacg gagcagcaag accatgtcaa gtcggtggag    900

tatctgagaa ataactttcg accacagcag cgtctgcatg acagggtggt gtccaagtcc    960

gccgtccgtg actcctggaa ccacgacatg acagacttct tagaaaaccc actggggaca   1020

gaagcctcta aagtttgcag ctctccaccc atccacatga aggtgcagcc tctgaaccag   1080
```

acggcactgc aggtgtcctg gagccagccg gagactatct accacccacc catcatgaac 1140
tacatgatct cctacagctg gaccaagaat gaggacgaga aggagaagac gtttacaaag 1200
gacagcgaca aagacttgaa agccaccatt agccatgtct cacccgatag cctttacctg 1260
ttccgagtcc aggccgtgtg tcggaacgac atgcgcagcg actttagcca gacgatgctg 1320
tttcaagcta ataccactcg aatattccaa gggaccagaa tagtgaaaac aggagtgccc 1380
acagcgtctc ctgcctcttc agccgacatg gcccccatca gctcggggtc ttctacctgg 1440
acgtcctctg gcatcccatt ctcatttgtt tccatggcaa ctgggatggg cccctcctcc 1500
agtggcagcc aggccacagt ggcctcggtg gtcaccagca cgctgctcgc cggcctgggg 1560
ttcggcggtg gtggcatctc ctctttcccc agcactgtgt ggcccacgcg cctcccgacg 1620
gccgcctcag ccagcaagca ggcggctagg ccagtcctag ccaccacaga ggccttggct 1680
tctccagggc ccgatggtga ttcgtcacca accaaggacg gcgagggcac cgaggaagga 1740
gagaaggatg agaaaagcga gagtgaggat ggggagcggg agcacgagga ggatggagag 1800
aaggactccg aaaagaagga gaagagtggg gtgacccacg ctgccgagga gcggaatcag 1860
acggagccca gccccacacc ctcgtctcct aacaggactg ccgagggagg gcatcagact 1920
atacctgggc atgagcagga tcacactgcc gtccccacag accagacggg cggaaggagg 1980
gatgccggcc caggcctgga ccccgacatg gtcacctcca cccaagtgcc ccccaccgcc 2040
acagaggagc agtatgcagg gagtgatccc aagaggcccg aaatgccatc taaaaagcct 2100
atgtcccgcg gggaccgatt ttctgaagac agcagattta tcactgttaa tccagcggaa 2160
aaaaacacct ctggaatgat aagccgccct gctccaggga ggatggagtg gatcatccct 2220
ctgattgtgg tatcagcctt gaccttcgtg tgcctcatcc ttctcattgc tgtgctcgtt 2280
tactggagag ggtgtaacaa aataaagtcc aagggctttc ccagacgttt ccgtgaagtg 2340
ccttcttctg gggagagagg agagaagggg agcagaaaat gttttcagac tgctcatttc 2400
tatgtggaag acagcagttc acctcgagtg gtccctaatg aaagtatccc tattattcct 2460
attccggatg acatggaagc cattcctgtc aaacagtttg tcaaacacat cggtgagctc 2520
tattctaata accagcatgg gttctctgag gattttgagg aagtccagcg ctgtactgct 2580
gatatgaaca tcactgcaga gcattccaat catccagaaa acaagcacaa aaacagatac 2640
atcaacattt tagcatatga tcacagtagg gtgaagttaa gacctttacc aggaaaagac 2700
tctaagcaca gcgactacat taatgcaaac tatgttgatg gttacaacaa agcaaaagcc 2760
tacattgcca cccaaggacc tttgaagtct acatttgaag atttctggag gatgatttgg 2820
gaacaaaaca ctggaatcat tgtgatgatt acgaaccttg tggaaaaagg aagacgaaaa 2880
tgtgatcagt attggccaac agagaacagt gaggaatatg gaaacattat tgtcacgctg 2940
aagagcacaa aaatacatgc ctgctacact gttcgtcgtt tttcaatcag aaatacaaaa 3000
gtgaaaaagg gtcagaaggg aaatcccaag ggtcgtcaga atgaaagggt agtgatccag 3060
tatcactata cacagtggcc tgacatggga gttcccgagt atgcccttcc agtactgact 3120
ttcgtgagga gatcctcagc agctcggatg ccagaaacgg gccctgtgtt ggtgcactgc 3180
agtgctggtg tgggcagaac aggcacctat attgtaatag acagcatgct gcaacagata 3240
aaagacaaaa gcacagttaa cgtcctggga ttcctgaagc atatcaggac acagcgtaac 3300
tacctcgtcc agactgagga gcagtacatt ttcatccatg atgccttgtt ggaagccatt 3360
cttggaaagg agactgaagt atcttcaaat cagctgcaca gctatgttaa cagcatcctt 3420

-continued

```
ataccaggag taggaggaaa gacacgactg gaaaagcaat tcaagctggt cacacagtgt   3480

aatgcaaaat atgtggaatg tttcagtgct cagaaagagt gtaacaaaga aaagaacaga   3540

aactcttcag ttgtgccatc tgagcgtgct cgagtgggtc ttgcaccatt gcctggaatg   3600

aaaggaacag attacattaa tgcttcttat atcatgggct attataggag caatgaattt   3660

attataactc agcatcctct gccacatact acgaaagatt tctggcgaat gatttgggat   3720

cataacgcac agatcattgt catgctgcca gacaaccaga gcttggcaga agatgagttt   3780

gtgtactggc caagtcgaga agaatccatg aactgtgagg cctttaccgt cacccttatc   3840

agcaaagaca gactgtgcct ctctaatgaa gaacaaatta tcatccatga ctttatcctt   3900

gaagctacac aggatgacta tgtcttagaa gttcggcact ttcagtgtcc caaatggcct   3960

aacccagatg cccccataag tagtaccttt gaacttatca acgtcatcaa ggaagaggcc   4020

ttaacaaggg atggtcccac cattgttcat gatgagtatg gagcagtttc agcaggaatg   4080

ttatgtgccc ttaccaccct gtcccagcaa ctggagaatg aaaatgctgt ggatgttttc   4140

caggttgcaa aaatgatcaa tcttatgagg cctggagtat tcacagacat tgaacaatac   4200

cagttcatct ataaagcaat gcttagcttg gtcagcacta aagaaaatgg aaatggtccc   4260

atgacagtag acaaaaatgg tgctgttctt attgcagatg aatcagaccc tgctgagagc   4320

atggagtccc tagtgtga                                                 4338
```

<210> SEQ ID NO 23
<211> LENGTH: 939
<212> TYPE: DNA
<213> ORGANISM: Homo sapiens

<400> SEQUENCE: 23

```
atgtcagcct tctctgaggc ggcgctggag aagaagctgt cggagttgag caactcgcag     60

cagagcgtgc agaccttgtc cctgtggctc attcaccacc gtaaacactc gcgtcccatc    120

gtcaccgtgt gggagcggga gctgcggaaa gccaaaccaa acaggaagct tacttttctc    180

tacctagcca atgatgtcat acagaacagc aagaggaagg ggccagagtt tacaaaagat    240

tttgcaccag ttatagtgga ggcttttaag catgtttcaa gtgaaactga tgaaagttgt    300

aagaagcacc ttggaagagt gttatctatt tgggaagaaa ggtctgttta tgaaaatgat    360

gtattagaac aacttaaaca agctctgtat ggtgataaga agcctaggaa gcgaacttat    420

gaacagataa aggtggatga aaatgaaaac tgttcctctc tgggatctcc aagtgaacca    480

ccacagactc tagatctcgt tagagcatta caagatctgg aaaatgcagc ctcaggtgat    540

gcagcagttc atcagaggat agcttcttta cctgttgaag tccaagaagt atctctatta    600

gataaaataa cagataaaga atctggagaa aggctttcca aaatggtaga ggatgcgtgt    660

atgttgctgg cagattacaa tggcagattg gcggcagaaa tagatgatag aaagcaactc    720

actcgaatgt tagcagattt tcttcgttgt caaaaggaag cccttgcaga gaaagagcat    780

aaattggaag agtacaagcg caagctagcc agagtttccc tggtgcgcaa agaactcagg    840

tcccggatcc agagcctgcc agacttatct cgattgccca atgtcactgg cagccacatg    900

cacctgccct ttgcgggaga catctacagt gaagattga                           939
```

<210> SEQ ID NO 24
<211> LENGTH: 1968
<212> TYPE: DNA
<213> ORGANISM: Homo sapiens

<400> SEQUENCE: 24

-continued

```
atggagcgga aagtgcttgc gctccaggcc cgaaagaaaa ggaccaaggc caagaaggac     60
aaagcccaaa ggaaatctga aactcagcac cgaggctctg ctccccactc tgagagtgat    120
ctaccagagc aggaagagga gattctggga tctgatgatg atgagcaaga agatcctaat    180
gattattgta aaggaggtta tcatcttgtg aaaattggag atctattcaa tgggagatac    240
catgtgatcc gaaagttagg ctggggacac ttttcaacag tatggttatc atgggatatt    300
caggggaaga aatttgtggc aatgaaagta gttaaaagtg ctgaacatta cactgaaaca    360
gcactagatg aaatccggtt gctgaagtca gttcgcaatt cagaccctaa tgatccaaat    420
agagaaatgg ttgttcaact actagatgac tttaaaatat caggagttaa tggaacacat    480
atctgcatgg tatttgaagt tttggggcat catctgctca agtggatcat caaatccaat    540
tatcaggggc ttccactgcc ttgtgtcaaa aaaattattc agcaagtgtt acagggtctt    600
gattatttac ataccaagtg ccgtatcatc cacactgaca ttaaaccaga gaacatctta    660
ttgtcagtga atgagcagta cattcggagg ctggctgcag aagcaacaga atggcagcga    720
tctggagctc ctccgccttc cggatctgca gtcagtactg ctccccagcc taaaccagct    780
gacaaaatgt caaagaataa gaagaagaaa ttgaagaaga agcagaagcg ccaggcagaa    840
ttactagaga agcgaatgca ggaaattgag gaaatggaga aagagtcggg ccctgggcaa    900
aaaagaccaa acaagcaaga agaatcagag agtcctgttg aaagaccctt gaaagagaac    960
ccacctaata aaatgaccca agaaaaactt gaagagtcaa gtaccattgg ccaggatcaa   1020
acgcttatgg aacgtgatac agagggtggt gcagcagaaa ttaattgcaa tggagtgatt   1080
gaagtcatta attatactca gaacagtaat aatgaaacat tgagacataa agaggatcta   1140
cataatgcta atgactgtga tgtccaaaat ttgaatcagg aatctagttt cctaagctcc   1200
caaaatggag acagcagcac atctcaagaa acagactctt gtacacctat aacatctgag   1260
gtgtcagaca ccatggtgtg ccagtcttcc tcaactgtag gtcagtcatt cagtgaacaa   1320
cacattagcc aacttcaaga aagcattcgg gcagagatac cctgtgaaga tgaacaagag   1380
caagaacata acggaccact ggacaacaaa ggaaaatcca cggctggaaa ttttcttgtt   1440
aatccccttg agccaaaaaa tgcagaaaag ctcaaggtga agattgctga ccttggaaat   1500
gcttgttggg tgcacaaaca tttcactgaa gatattcaaa caaggcaata tcgttccttg   1560
gaagttctaa tcggatctgg ctataatacc cctgctgaca tttggagcac ggcatgcatg   1620
gcctttgaac tggccacagg tgactatttg tttgaacctc attcagggga agagtacact   1680
cgagatgaag atcacattgc attgatcata gaacttctgg ggaaggtgcc tcgcaagctc   1740
attgtggcag gaaaatattc caaggaattt ttcaccaaaa aaggtgacct gaaacatatc   1800
acgaagctga aaccttgggg cctttttgag gttctagtgg agaagtatga gtggtcgcag   1860
gaagaggcag ctggcttcac agatttctta ctgcccatgt tggagctgat ccctgagaag   1920
agagccactg ccgccgagtg tctccggcac ccttggctta actcctaa                1968
```

<210> SEQ ID NO 25
<211> LENGTH: 2100
<212> TYPE: DNA
<213> ORGANISM: Homo sapiens

<400> SEQUENCE: 25

```
atgagctccc ggaaagtgct ggccattcag gcccgaaagc ggaggccgaa aagagagaaa     60
catccgaaaa agccggagcc tcaacagaaa gctcctttag ttcctcctcc tccaccgcca    120
```

-continued

```
ccaccaccac caccgccacc tttgccagac cccacacccc cggagccaga ggaggagatc    180

ctgggatcag atgatgagga gcaagaggac cctgcggact actgcaaagg tggatatcat    240

ccagtgaaaa ttggagacct cttcaatggc cggtatcatg ttattagaaa gcttggatgg    300

gggcacttct ctactgtctg gctgtgctgg gatatgcagg ggaaaagatt tgttgcaatg    360

aaagttgtaa aaagtgccca gcattatacg gagacagcct tggatgaaat aaaattgctc    420

aaatgtgttc gagaaagtga tcccagtgac ccaaacaaag acatggtggt ccagctcatt    480

gacgacttca agatttcagg catgaatggg atacatgtct gcatggtctt cgaagtactt    540

ggccaccatc tcctcaagtg gatcatcaaa tccaactatc aaggcctccc agtacgttgt    600

gtgaagagta tcattcgaca ggtccttcaa gggttagatt acttacacag taagtgcaag    660

atcattcata ctgacataaa gccggaaaat atcttgatgt gtgtggatga tgcatatgtg    720

agaagaatgg cagctgaggc cactgagtgg cagaaagcag gtgctcctcc tccttcaggg    780

tctgcagtga gtacggctcc acagcagaaa cctataggaa aaatatctaa aaacaaaaag    840

aaaaaactga aaaagaaaca gaagaggcag gctgagttat tggagaagcg cctgcaggag    900

atagaagaat tggagcgaga agctgaaagg aaaataatag aagaaaacat cacctcagct    960

gcaccttcca atgaccagga tggcgaatac tgcccagagg tgaaactaaa aacaacagga   1020

ttagaggagg cggctgaggc agagactgca aaggacaatg gtgaagctga ggaccaggaa   1080

gagaaagaag atgctgagaa agaaaacatt gaaaaagatg aagatgatgt agatcaggaa   1140

cttgcgaaca tagaccctac gtggatagaa tcacctaaaa ccaatggcca tattgagaat   1200

ggcccattct cactggagca gcaactggac gatgaagatg atgatgaaga agactgccca   1260

aatcctgagg aatataatct tgatgagcca aatgcagaaa gtgattacac atatagcagc   1320

tcctatgaac aattcaatgg tgaattgcca aatggacgac ataaaattcc cgagtcacag   1380

ttcccagagt tttccacctc gttgttctct ggatccttag aacctgtggc ctgcggctct   1440

gtgctttctg agggatcacc acttactgag caagaggaga gcagtccatc ccatgacaga   1500

agcagaacgg tttcagcctc cagtactggg gatttgccaa aagcaaaaac ccgggcagct   1560

gacttgttgg tgaatcccct ggatccgcgg aatgcagata aaattagagt aaaaattgct   1620

gacctgggaa atgcttgttg ggtgcataaa cacttcacgg aagacatcca gacgcgtcag   1680

taccgctcca tagaggtttt aataggagcg gggtacagca cccctgcgga catctggagc   1740

acggcgtgta tggcatttga gctggcaacg ggagattatt tgtttgaacc acattctggg   1800

gaagactatt ccagagacga agaccacata gcccacatca tagagctgct aggcagtatt   1860

ccaaggcact ttgctctatc tggaaaatat tctcgggaat tcttcaatcg cagaggagaa   1920

ctgcgacaca tcaccaagct gaagccctgg agcctctttg atgtacttgt ggaaaagtat   1980

ggctggcccc atgaagatgc tgcacagttt acagatttcc tgatcccgat gttagaaatg   2040

gttccagaaa aacgagcctc agctggcgaa tgccttcggc atccttggtt gaattcttag   2100
```

<210> SEQ ID NO 26
<211> LENGTH: 1638
<212> TYPE: DNA
<213> ORGANISM: Homo sapiens

<400> SEQUENCE: 26

```
atggcggagc cgagcggctc gcccgtgcac gtccagcttc cccagcaggc ggccccggtg     60

acagcggcgg cggcggcggc cccggcggcc gcgacagcag cgccggcccc ggcagctccc    120

gcggccccgg ccccggcccc ggccccggcg gcacaggctg tcggctggcc catctgcagg    180
```

```
gacgcgtacg agctgcagga ggttatcggc agtggagcta ctgctgtggt tcaggcagcc    240
ctatgcaaac ccaggcaaga acgtgtagca ataaaacgga tcaacttgga aaaatgccag    300
accagtatgg atgaactatt aaaagaaatt caagccatga gtcagtgcag ccatccccaac   360
gtagtgacct attacacctc ttttgtggtc aaagatgaac tttggctggt catgaaatta    420
ctaagtggag gttcaatgtt ggatatcata aaatacattg tcaaccgagg agaacacaag    480
aatggagttc tggaagaggc aataatagca acaattctta aagaggtttt ggaaggctta    540
gactatctac acagaaacgg tcagattcac agggatttga aagctggtaa tattcttctg    600
ggtgaggatg gttcagtaca aatagcagat tttggggtaa gtgcgttcct agcaacaggg    660
ggtgatgtta cccgaaataa agtaagaaaa acattcgttg gcaccccatg ttggatggct    720
cctgaagtca tggaacaggt gagaggctat gacttcaagg ctgacatgtg gagttttgga    780
ataactgcca ttgaattagc aacaggagca gcgccttatc acaaatatcc tcccatgaaa    840
gtgttaatgt tgactttgca aaatgatcca cccactttgg aaacaggggt agaggataaa    900
gaaatgatga aaaagtacgg caagtccttt agaaaattac tttcactgtg tcttcagaaa    960
gatccttcca aaaggcccac agcagcagaa cttttaaaat gcaaattctt ccagaaagcc   1020
aagaacagag agtacctgat tgagaagctg cttacaagaa caccagacat agcccaaaga   1080
gccaaaaagg taagaagagt tcctgggtca agtggtcacc ttcataaaac cgaagacggg   1140
gactgggagt ggagtgacga cgagatggat gagaagagcg aagaagggaa agcagctttt   1200
tctcaggaaa agtcacgaag agtaaaagaa gaaaatccag agattgcagt gagtgccagc   1260
accatccccg aacaaataca gtccctctct gtgcacgact ctcagggccc acccaatgct   1320
aatgaagact acagagaagc ttcttcttgt gccgtgaacc tcgttttgag attaagaaac   1380
tccagaaagg aacttaatga catacgattt gagtttactc caggaagaga tacagcagat   1440
ggtgtatctc aggagctctt ctctgctggc ttggtggatg gtcacgatgt agttatagtg   1500
gctgctaatt tacagaagat tgtagatgat cccaaagctt taaaaacatt gacatttaag   1560
ttggcttctg gctgtgatgg gtcggagatt cctgatgaag tgaagctgat tgggtttgct   1620
cagttgagtg tcagctga                                                  1638
```

<210> SEQ ID NO 27
<211> LENGTH: 705
<212> TYPE: DNA
<213> ORGANISM: Homo sapiens

<400> SEQUENCE: 27

```
atgagctgca ttaacctgcc cactgtgctg cctggctccc ccagcaagac ccgggggcag     60
atccaggtga ttctcgggcc gatgttctca ggaaaaagca cagagttgat gagacgcgtc    120
cgtcgcttcc agattgctca gtacaagtgc ctggtgatca agtatgccaa agacactcgc    180
tacagcagca gcttctgcac acatgaccgg aacaccatgg aggcactgcc cgcctgcctg    240
ctccgagacg tggcccagga ggccctgggc gtggctgtca taggcatcga cgaggggcag    300
tttttccctg acatcgtgga gttctgcgag gccatggcca acgccgggaa gaccgtaatt    360
gtggctgcac tggatgggac cttccagagg aagccatttg ggccatcct gaacctggtg     420
ccgctggccg agagcgtggt gaagctgacg gcggtgtgca tggagtgctt ccgggaagcc    480
gcctatacca agaggctcgg cacagagaag gaggtcgagg tgattggggg agcagacaag    540
taccactccg tgtgtcggct ctgctacttc aagaaggcct caggccagcc tgccgggccg    600
```

-continued gacaacaaag agaactgccc agtgccagga aagccagggg aagccgtggc tgccaggaag 660
ctctttgccc cacagcagat tctgcaatgc agccctgcca actga 705

<210> SEQ ID NO 28
<211> LENGTH: 2574
<212> TYPE: DNA
<213> ORGANISM: Homo sapiens

<400> SEQUENCE: 28
atggaatccg aggatttaag tggcagagaa ttgacaattg attccataat gaacaaagtg 60
agagacatta aaaataagtt taaaaatgaa gaccttactg atgaactaag cttgaataaa 120
atttctgctg atactacaga taactcggga actgttaacc aaattatgat gatggcaaac 180
aacccagagg actggttgag tttgttgctc aaactagaga aaaacagtgt tccgctaagt 240
gatgctcttt taaataaatt gattggtcgt tacagtcaag caattgaagc gcttcccccca 300 gataaatatg gccaaaatga gagttttgct agaattcaag tgagatttgc tgaattaaaa 360
gctattcaag agccagatga tgcacgtgac tactttcaaa tggccagagc aaactgcaag 420
aaatttgctt ttgttcatat atcttttgca caatttgaac tgtcacaagg taatgtcaaa 480
aaaagtaaac aacttcttca aaaagctgta gaacgtggag cagtaccact agaaatgctg 540
gaaattgccc tgcggaattt aaacctccaa aaaaagcagc tgctttcaga ggaggaaaag 600
aagaatttat cagcatctac ggtattaact gcccaagaat cattttccgg ttcacttggg 660
catttacaga ataggaacaa cagttgtgat tccagaggac agactactaa agccaggttt 720
ttatatggag agaacatgcc accacaagat gcagaaatag gttaccggaa ttcattgaga 780
caaactaaca aaactaaaca gtcatgccca tttggaagag tcccagttaa ccttctaaat 840
agcccagatt gtgatgtgaa gacagatgat tcagttgtac cttgttttat gaaaagacaa 900
acctctagat cagaatgccg agatttggtt gtgcctggat ctaaaccaag tggaaatgat 960
tcctgtgaat taagaaattt aaagtctgtt caaaatagtc atttcaagga acctctggtg 1020
tcagatgaaa agagttctga acttattatt actgattcaa taaccctgaa gaataaaacg 1080
gaatcaagtc ttctagctaa attagaagaa actaaagagt atcaagaacc agaggttcca 1140
gagagtaacc agaaacagtg gcaatctaag agaaagtcag agtgtattaa ccagaatcct 1200
gctgcatctt caaatcactg gcagattccg gagttagccc gaaaagttaa tacagagcag 1260
aaacatacca cttttgagca acctgtcttt tcagtttcaa aacagtcacc accaatatca 1320
acatctaaat ggtttgaccc aaaatctatt tgtaagacac caagcagcaa taccttggat 1380
gattacatga gctgttttag aactccagtt gtaaagaatg actttccacc tgcttgtcag 1440
ttgtcaacac cttatggcca acctgcctgt ttccagcagc aacagcatca aatacttgcc 1500
actccacttc aaaatttaca ggttttagca tcttcttcag caaatgaatg catttcggtt 1560
aaaggaagaa tttattccat attaaagcag ataggaagtg gaggttcaag caaggtattt 1620
caggtgttaa atgaaaagaa acagatatat gctataaaat atgtgaactt agaagaagca 1680
gataaccaaa ctcttgatag ttaccggaac gaaatagctt atttgaataa actacaacaa 1740
cacagtgata agatcatccg actttatgat tatgaaatca cggaccagta catctacatg 1800
gtaatggagt gtggaaatat tgatcttaat agttggctta aaaagaaaaa atccattgat 1860
ccatgggaac gcaagagtta ctggaaaaat atgttagagg cagttcacac aatccatcaa 1920
catggcattg ttcacagtga tcttaaacca gctaactttc tgatagttga tggaatgcta 1980
aagctaattg attttgggat tgcaaaccaa atgcaaccag atacaacaag tgttgttaaa 2040

-continued

```
gattctcagg ttggcacagt taattatatg ccaccagaag caatcaaaga tatgtcttcc   2100

tccagagaga atgggaaatc taagtcaaag ataagcccca aaagtgatgt ttggtcctta   2160

ggatgtattt tgtactatat gacttacggg aaaacaccat ttcagcagat aattaatcag   2220

atttctaaat tacatgccat aattgatcct aatcatgaaa ttgaatttcc cgatattcca   2280

gagaaagatc ttcaagatgt gttaaagtgt tgtttaaaaa gggacccaaa acagaggata   2340

tccattcctg agctcctggc tcatccatat gttcaaattc aaactcatcc agttaaccaa   2400

atggccaagg gaaccactga agaaatgaaa tatgttctgg gccaacttgt tggtctgaat   2460

tctcctaact ccattttgaa agctgctaaa actttatatg aacactatag tggtggtgaa   2520

agtcataatt cttcatcctc caagactttt gaaaaaaaaa ggggaaaaaa atga         2574
```

<210> SEQ ID NO 29
<211> LENGTH: 756
<212> TYPE: DNA
<213> ORGANISM: Homo sapiens

<400> SEQUENCE: 29

```
atgacccggc tgacagtcct ggccctgctg gctggtctgc tggcgtcctc gagggccggc     60

tccagccccc ttttggacat cgttggcggc cggaaggcga ggccccgcca gttcccgttc    120

ctggcctcca ttcagaatca aggcaggcac ttctgcgggg gtgccctgat ccatgcccgc    180

ttcgtgatga ccgcggccag ctgcttccaa agccagaacc ccggggttag caccgtggtg    240

ctgggtgcct atgacctgag gcggcgggag aggcagtccc gccagacgtt ttccatcagc    300

agcatgagcg agaatggcta cgacccccag cagaacctga acgacctgat gctgcttcag    360

ctggaccgtg aggccaacct caccagcagc gtgacgatac tgccactgcc tctgcagaac    420

gccacggtgg aagccggcac cagatgccag gtggccggct gggggagcca gcgcagtggg    480

gggcgtctct cccgttttcc caggtttgtc aacgtgactg tgacccccga ggaccagtgt    540

cgccccaaca acgtgtgcac cggtgtgctc acccgccgcg gtggcatctg caatggggac    600

gggggcaccc ccctcgtctg cgagggcctg gcccacggcg tggcctcctt ttccctgggg    660

ccctgtggcc gaggccctga cttcttcacc cgagtggcgc tcttccgaga ctggatcgat    720

ggtgttctca acaacccggg accggggcca gcctag                              756
```

<210> SEQ ID NO 30
<211> LENGTH: 495
<212> TYPE: DNA
<213> ORGANISM: Homo sapiens

<400> SEQUENCE: 30

```
atgtcagaac cggctgggga tgtccgtcag aacccatgcg gcagcaaggc ctgccgccgc     60

ctcttcggcc cagtggacag cgagcagctg agccgcgact gtgatgcgct aatggcgggc    120

tgcatccagg aggcccgtga gcgatggaac ttcgactttg tcaccgagac accactggag    180

ggtgacttcg cctgggagcg tgtgcggggc cttggcctgc ccaagctcta ccttcccacg    240

gggccccggc gaggccggga tgagttggga ggaggcaggc ggcctggcac ctcacctgct    300

ctgctgcagg ggacagcaga ggaagaccat gtggacctgt cactgtcttg taccctttgtg    360

cctcgctcag gggagcaggc tgaagggtcc ccaggtggac ctggagactc tcagggtcga    420

aaacggcggc agaccagcat gacagatttc taccactcca aacgccggct gatcttctcc    480

aagaggaagc cctaa                                                     495
```

-continued

<210> SEQ ID NO 31
<211> LENGTH: 2742
<212> TYPE: DNA
<213> ORGANISM: Homo sapiens

<400> SEQUENCE: 31
atgggaccag aggccctgtc atctttactg ctgctgctct tggtggcaag tggagatgct 60
gacatgaagg gacattttga tcctgccaag tgccgctatg ccctgggcat gcaggaccgg 120
accatcccag acagtgacat ctctgcttcc agctcctggt cagattccac tgccgcccgc 180
cacagcaggt tggagagcag tgacggggat ggggcctggt gccccgcagg gtcggtgttt 240
cccaaggagg aggagtactt gcaggtggat ctacaacgac tgcacctggt ggctctggtg 300
ggcacccagg gacggcatgc cgggggcctg ggcaaggagt tctcccggag ctaccggctg 360
cgttactccc gggatggtcg ccgctggatg ggctggaagg accgctgggg tcaggaggtg 420
atctcaggca atgaggaccc tgagggagtg gtgctgaagg accttgggcc ccccatggtt 480
gcccgactgg ttcgcttcta cccccgggct gaccgggtca tgagcgtctg tctgcgggta 540
gagctctatg gctgcctctg gagggatgga ctcctgtctt acaccgcccc tgtggggcag 600
acaatgtatt tatctgaggc cgtgtacctc aacgactcca cctatgacgg acataccgtg 660
ggcggactgc agtatggggg tctgggccag ctggcagatg gtgtggtggg gctggatgac 720
tttaggaaga gtcaggagct gcgggtctgg ccaggctatg actatgtggg atggagcaac 780
cacagcttct ccagtggcta tgtggagatg gagtttgagt ttgaccggct gagggccttc 840
caggctatgc aggtccactg taacaacatg cacacgctgg gagcccgtct gcctggcggg 900
gtggaatgtc gcttccggcg tggccctgcc atggcctggg agggggagcc catgcgccac 960
aacctagggg gcaacctggg ggaccccaga gcccgggctg tctcagtgcc ccttggcggc 1020
cgtgtggctc gctttctgca gtgccgcttc ctctttgcgg ggccctggtt actcttcagc 1080
gaaatctcct tcatctctga tgtggtgaac aattcctctc cggcactggg aggcaccttc 1140
ccgccagccc cctggtggcc gcctggccca cctcccacca acttcagcag cttggagctg 1200
gagcccagag gccagcagcc cgtggccaag gccgagggga gcccgaccgc catcctcatc 1260
ggctgcctgg tggccatcat cctgctcctg ctgctcatca ttgccctcat gctctggcgg 1320
ctgcactggc gcaggctcct cagcaaggct gaacggaggg tgttggaaga ggagctgacg 1380
gttcacctct ctgtccctgg ggacactatc ctcatcaaca accgcccagg tcctagagag 1440
ccacccccgt accaggagcc ccggcctcgt gggaatccgc cccactccgc tccctgtgtc 1500
cccaatggct ctgcgttgct gctctccaat ccagcctacc gcctccttct ggccacttac 1560
gcccgtcccc ctcgaggccc gggccccccc acacccgcct gggccaaacc caccaacacc 1620
caggcctaca gtggggacta tatggagcct gagaagccag gcgccccgct tctgccccca 1680
cctccccaga acagcgtccc ccattatgcc gaggctgaca ttgttaccct gcagggcgtc 1740
accgggggca acacctatgc tgtgcctgca ctgcccccag gggcagtcgg ggatggggccc 1800 cccagagtgg atttccctcg atctcgactc cgcttcaagg agaagcttgg cgagggccag 1860
tttggggagg tgcacctgtg tgaggtcgac agccctcaag atctggttag tcttgatttc 1920
ccccttaatg tgcgtaaggg acaccctttg ctggtagctg tcaagatctt acggccagat 1980
gccaccaaga atgccaggaa tgatttcctg aaagaggtga agatcatgtc gaggctcaag 2040
gacccaaaca tcattcggct gctgggcgtg tgtgtgcagg acgaccccct ctgcatgatt 2100
actgactaca tggagaacgg cgacctcaac cagttcctca gtgcccacca gctggaggac 2160
aaggcagccg agggggcccc tggggacggg caggctgcgc aggggcccac catcagctac 2220
ccaatgctgc tgcatgtggc agcccagatc gcctccggca tgcgctatct ggccacactc 2280
aactttgtac atcgggacct ggccacgcgg aactgcctag ttggggaaaa tttcaccatc 2340
aaaatcgcag actttggcat gagccggaac ctctatgctg ggactattta ccgtgtgcag 2400
ggccgggcag tgctgcccat ccgctggatg gcctgggagt gcatcctcat ggggaagttc 2460
acgactgcga gtgacgtgtg ggcctttggt gtgaccctgt gggaggtgct gatgctctgt 2520
agggcccagc cctttgggca gctcaccgac gagcaggtca tcgagaacgc gggggagttc 2580
ttccgggacc agggccggca ggtgtacctg tcccggccgc ctgcctgccc gcagggccta 2640
tatgagctga tgcttcggtg ctggagccgg gagtctgagc agcgaccacc cttttcccag 2700
ctgcatcggt tcctggcaga ggatgcactc aacacggtgt ga 2742

<210> SEQ ID NO 32
<211> LENGTH: 2772
<212> TYPE: DNA
<213> ORGANISM: Homo sapiens

<400> SEQUENCE: 32
atggactcca ttgggtcttc agggttgcgg caggggggaag aaaccctgag ttgctctgag 60
gagggcttgc ccgggccctc agacagctca gagctggtgc aggagtgcct gcagcagttc 120
aaggtgacaa gggcacagct acagcagatc caagccagcc tcttgggttc catggagcag 180
gcgctgaggg gacaggccag ccctgcccct gcggtccgga tgctgcctac atacgtgggg 240
tccaccccac atggcactga gcaaggagac ttcgtggtgc tggagctggg ggccacaggg 300
gcctcactgc gtgttttgtg ggtgactcta actggcattg aggggcatag ggtggagccc 360
agaagccagg agtttgtgat cccccaagag gtgatgctgg gtgctggcca gcagctcttt 420
gactttgctg cccactgcct gtctgagttc ctggatgcgc agcctgtgaa caaacagggt 480
ctgcagcttg gcttcagctt ctctttccct tgtcaccaga cgggcttgga caggagcacc 540
ctcatttcct ggaccaaagg ttttaggtgc agtggtgtgg aaggccagga tgtggtccag 600
ctgctgagag atgccattcg gaggcagggg gcctacaaca tcgacgtggt tgctgtggtg 660
aacgacacag tgggcaccat gatgggctgt gagccggggg tcaggccgtg tgaggttggg 720
ctagttgtag acacgggcac caacgcgtgt tacatggagg aggcacggca tgtggcagtg 780
ctggacgaag accggggccg cgtctgcgtc agcgtcgagt ggggctcctt cagcgatgat 840
ggggcgctgg gaccagtgct gaccaccttc gaccataccc tggaccatga gtccctgaat 900
cctggtgctc agaggtttga gaagatgatc ggaggcctgt acctgggtga gctggtgcgg 960
ctggtgctgg ctcacttggc ccggtgtggg gtcctctttg gtggctgcac ctcccctgcc 1020
ctgctgagcc aaggcagcat cctcctggaa cacgtggctg agatggagga cccctctact 1080
ggggcagccc gtgtccatgc tatcctgcag gacttgggcc tgagccctgg ggcttcggat 1140
gttgagcttg tgcagcacgt ctgtgcggcc gtgtgcacgc gggctgccca gctctgtgct 1200
gccgccctgg ccgctgttct ctcctgcctc cagcacagcc gggagcaaca aacactccag 1260
gttgctgtgg ccaccggagg ccgagtgtgt gagcggcacc ccaggttctg cagcgtcctg 1320
caggggacag tgatgctcct ggccccggaa tgcgatgtct ccttaatccc ctctgtggat 1380
ggtggtggcc ggggagtggc gatggtgact gccgtggctg cccgtctggc tgcccaccgg 1440
cgcctgctgg aggagaccct ggccccattc cggttgaacc atgatcaact ggctgcggtt 1500
caggcacaga tgcggaaggc catggccaag gggctccgag gggaggcctc ctcccttcgc 1560
atgctgccca ctttcgtccg ggccacccct gacggcagcg agcgagggga tttcctggcc 1620
ctggacctcg gggcacgaa cttccgtgtc ctcctggtac gtgtgaccac aggcgtgcag 1680
atcaccagcg agatctactc cattcccgag actgtggccc agggttctgg gcagcagctc 1740
tttgaccaca tcgtggactg catcgtggac ttccagcaga agcagggcct gagcgggcag 1800
agcctcccac tgggttttac cttctccttc ccatgtaggc agcttggcct agaccagggc 1860
atcctcctga actggaccaa gggtttcaag gcatcagact gcgagggcca agatgtcgtg 1920
agtctgttgc gggaagccat cactcgcaga caggcagtgg agctgaatgt ggttgccatt 1980
gtcaatgaca cggtggggac catgatgtcc tgtggctatg aggacccccg ttgcgagata 2040
ggcctcattg tcggaaccgg caccaatgcc tgctacatgg aggagctccg gaatgtggcg 2100
ggcgtgcctg ggactcagg ccgcatgtgc atcaacatgg agtggggcgc ctttggggac 2160
gatggctctc tggccatgct cagcacccgc tttgatgcaa gtgtggacca ggcgtccatc 2220
aaccccggca agcagaggtt tgaaaagatg atcagcggca tgtacctggg ggagatcgtc 2280
cgccacatcc ttttacattt aaccagcctt ggcgttctct tccggggcca gcagatccag 2340
cgccttcaga ccagggacat cttcaagacc aagttcctct ctgagatcga aagtgacagc 2400
ctggccctgc ggcaggtccg agccatccta gaggatctgg ggctacccct gacctcagat 2460
gacgccctga tggtgctaga ggtgtgccag gctgtgtccc agagggctgc ccagctctgt 2520
ggggcgggtg tagctgccgt ggtggagaag atccgggaga accggggcct ggaagagctg 2580
gcagtgtctg tgggggtgga tggaacgctc tacaagctgc acccgcgctt ctccagcctg 2640
gtggcggcca cagtgcggga gctggcccct cgctgtgtgg tcacgttcct gcagtcagag 2700
gatgggtccg gcaaaggtgc ggccctggtc accgctgttg cctgccgcct tgcgcagttg 2760
actcgtgtct ga 2772

<210> SEQ ID NO 33
<211> LENGTH: 2463
<212> TYPE: DNA
<213> ORGANISM: Homo sapiens

<400> SEQUENCE: 33
atggcgctgc tgcgggatgt gtcgctgcag gacccgcggg accgcttcga gctgctgcag 60
cgcgtggggg ccgggaccta tggcgacgtc tacaaggccc gcgacacggt cacgtccgaa 120
ctggccgccg tgaagatagt caagctagac ccaggggacg acatcagctc cctccagcag 180
gaaatcacca tcctgcgtga gtgccgccac cccaatgtgg tggcctacat tggcagctac 240
ctcaggaatg accgcttgtg gatctgcatg gagttctgcg gagggggctc cctgcaggag 300
atttaccatg ccactgggcc cctggaggag cggcagattg cctacgtctg ccgagaggca 360
ctgaaggggc tccaccacct gcattctcag gggaagatcc acagagacat caagggagcc 420
aaccttctcc tcactctcca gggagatgtc aaactggctg actttggggt gtcaggcgag 480
ctgacagcgt ctgtggccaa gaggaggtct ttcattggga ctccctactg gatggctccc 540
gaggtggctg ctgtggagcg caaaggtggc tacaatgagc tatgtgacgt ctgggccctg 600
ggcatcactg ccattgagct gggcgagctg cagcccccctc tgttccacct gcaccccatg 660
agggccctga tgctcatgtc gaagagcagc ttccagccgc ccaaactgag agataagact 720
cgctggaccc agaatttcca ccactttctc aaactggccc tgaccaagaa tcctaagaag 780
aggccgacag cagagaagct cctgcagcac ccgttcacga ctcagcagct ccctcgggcc 840
ctcctcacac agctgctgga caaagccagt gaccctcatc tggggacccc ctcccctgag 900
gactgtgagc tggagaccta tgacatgttt ccagacacca ttcactcccg ggggcagcac 960
ggcccagccg agaggacccc ctcggagatc cagtttcacc aggtgaaatt tggcgcccca 1020
cgcaggaagg aaactgaccc actgaatgag ccgtgggagg aagagtggac actactggga 1080
aaggaagagt tgagtgggag cctgctgcag tcggtccagg aggccctgga ggaaaggagt 1140
ctgactattc ggtcagcctc agaattccag gagctggact ccccagacga taccatggga 1200
accatcaagc gggccccgtt cctagggcca ctccccactg accctccagc agaggagcct 1260
ctgtccagtc ccccaggaac cctgccccca cctccttcag gccccaacag ctccccactg 1320
ctgcccacgg cctgggccac catgaagcag cgggaggatc ctgagaggtc atcctgccac 1380
gggctccccc caactcccaa ggtgcatatg ggcgcctgct tctccaaggt cttcaatggc 1440 tgcccccctgc ggatccacgc tgctgtcacc tggattcacc ctgttactcg ggaccagttc 1500
ctggtggtag gggccgagga aggcatctac acactcaacc tgcatgaact gcatgaggat 1560
acgctggaga agctgatttc acatcgctgc tcctggctct actgcgtgaa caacgtgctg 1620
ctgtcactct cagggaaatc cacgcacatc tgggcccatg acctcccagg cctgtttgag 1680
cagcggaggc tacagcaaca ggttcccctc tccatcccca ccaaccgcct cacccagcgc 1740
atcatcccca ggcgctttgc tctgtccacc aagattcctg acaccaaagg ctgcttgcag 1800
tgtcgtgtgg tgcggaaccc ctacacgggt gccaccttcc tgctggccgc cctgcccacc 1860
agcctgctcc tgctgcagtg gtatgagccg ctgcagaagt ttctgctgct gaagaacttc 1920
tccagccctc tgcccagccc agctgggatg ctggagccgc tggtgctgga tgggaaggag 1980
ctgccgcagg tgtgtgttgg ggccgagggg cctgaggggc ccggctgccg cgtcctgttc 2040
catgtcctgc ccctggaggc tggcctgacg cccgacatcc tcatcccacc tgaggggatc 2100
ccaggctcgg cccagcaggt gatccaggtg gacagggaca caatcctagt cagctttgaa 2160
cgctgtgtga ggattgtcaa catgcagggc gagcccacgg ccacactggc acctgagctg 2220
acctttgatt tccccatcga gactgtggtg tgcctgcagg acagtgtgct ggccttctgg 2280
agccatggga tgcaaggccg aagcctggat accaatgagg tgacccagga gatcacagat 2340
gaaacaagga tcttccgagt gcttggggcc cacagagaca tcatcctgga gagcattccc 2400
actgacaacc cagaggcgca cagcaacctc tacatcctca cgggccacca gagcacctac 2460
taa 2463

<210> SEQ ID NO 34
<211> LENGTH: 3000
<212> TYPE: DNA
<213> ORGANISM: Homo sapiens

<400> SEQUENCE: 34
atggggccgg ccccgctgcc gctgctgctg ggcctcttcc tccccgcgct ctggcgtaga 60
gctatcactg aggcaaggga agaagccaag ccttacccgc tattcccggg accttttcca 120
gggagcctgc aaactgacca cacaccgctg ttatcccttc ctcacgccag tgggtaccag 180
cctgccttga tgttttcacc aacccagcct ggaagaccac atacaggaaa cgtagccatt 240
ccccaggtga cctctgtcga atcaaagccc ctaccgcctc ttgccttcaa acacacagtt 300
ggacacataa tactttctga acataaaggt gtcaaattta attgctcaat cagtgtacct 360
aatatatacc aggacaccac aatttcttgg tggaaagatg ggaaggaatt gcttggggca 420

-continued

```
catcatgcaa ttacacagtt ttatccagat gatgaagtta cagcaataat cgcttccttc    480
agcataacca gtgtgcagcg ttcagacaat gggtcgtata tctgtaagat gaaaataaac    540
aatgaagaga tcgtgtctga tcccatctac atcgaagtac aaggacttcc tcactttact    600
aagcagcctg agagcatgaa tgtcaccaga aacacagcct tcaacctcac ctgtcaggct    660
gtgggcccgc ctgagcccgt caacattttc tgggttcaaa acagtagccg tgttaacgaa    720
cagcctgaaa aatccccctc cgtgctaact gttccaggcc tgacggagat ggcggtcttc    780
agttgtgagg cccacaatga caaagggctg accgtgtcca agggagtgca gatcaacatc    840
aaagcaattc cctccccacc aactgaagtc agcatccgta acagcactgc acacagcatt    900
ctgatctcct gggttcctgg ttttgatgga tactccccgt tcaggaattg cagcattcag    960
gtcaaggaag ctgatccgct gagtaatggc tcagtcatga tttttaacac ctctgcctta   1020
ccacatctgt accaaatcaa gcagctgcaa gccctggcta attacagcat tggtgtttcc   1080
tgcatgaatg aaataggctg gtctgcagtg agcccttgga ttctagccag cacgactgaa   1140
ggagccccat cagtagcacc tttaaatgtc actgtgtttc tgaatgaatc tagtgataat   1200
gtggacatca gatggatgaa gcctccgact aagcagcagg atggagaact ggtgggctac   1260
cggatatccc acgtgtggca gagtgcaggg atttccaaag agctcttgga ggaagttggc   1320
cagaatggca gccgagctcg gatctctgtt caagtccaca atgctacgtg cacagtgagg   1380
attgcagccg tcaccagagg gggagttggg cccttcagtg atccagtgaa aatatttatc   1440
cctgcacacg gttgggtaga ttatgccccc tcttcaactc cggcgcctgg caacgcagat   1500
cctgtgctca tcatctttgg ctgcttttgt ggatttattt tgattgggtt gattttatac   1560
atctccttgg ccatcagaaa aagagtccag gagacaaagt ttgggaatgc attcacagag   1620
gaggattctg aattagtggt gaattatata gcaaagaaat ccttctgtcg gcgagccatt   1680
gaacttacct tacatagctt gggagtcagt gaggaactac aaaataaact agaagatgtt   1740
gtgattgaca ggaatcttct aattcttgga aaaattctgg gtgaaggaga gtttgggtct   1800
gtaatggaag gaaatcttaa gcaggaagat gggacctctc tgaaagtggc agtgaagacc   1860
atgaagttgg acaactcttc acagcgggag atcgaggagt ttctcagtga ggcagcgtgc   1920
atgaaagact tcagccaccc aaatgtcatt cgacttctag gtgtgtgtat agaaatgagc   1980
tctcaaggca tcccaaagcc catggtaatt ttacccttca tgaaatacgg ggacctgcat   2040
acttacttac tttattcccg attggagaca ggaccaaagc atattcctct gcagacacta   2100
ttgaagttca tggtggatat tgccctggga atggagtatc tgagcaacag gaattttctt   2160
catcgagatt tagctgctcg aaactgcatg ttgcgagatg acatgactgt ctgtgttgcg   2220
gacttcggcc tctctaagaa gatttacagt ggcgattatt accgccaagg ccgcattgct   2280
aagatgcctg ttaaatggat cgccatagaa agtcttgcag accgagtcta cacaagtaaa   2340
agtgatgtgt gggcatttgg cgtgaccatg tgggaaatag ctacgcgggg aatgactccc   2400
tatcctgggg tccagaacca tgagatgtat gactatcttc tccatggcca caggttgaag   2460
cagcccgaag actgcctgga tgaactgtat gaaataatgt actcttgctg gagaaccgat   2520
cccttagacc gccccacctt ttcagtattg aggctgcagc tagaaaaact cttagaaagt   2580
ttgcctgacg ttcggaacca agcagacgtt atttacgtca atacacagtt gctggagagc   2640
tctgagggcc tggcccaggg ctccaccctt gctccactgg acttgaacat cgaccctgac   2700
tctataattg cctcctgcac tccccgcgct gccatcagtg tggtcacagc agaagttcat   2760
gacagcaaac ctcatgaagg acggtacatc ctgaatgggg gcagtgagga atgggaagat   2820
```

```
ctgacttctg cccctctgc tgcagtcaca gctgaaaaga acagtgtttt accgggggag   2880

agacttgtta ggaatggggt ctcctggtcc cattcgagca tgctgccctt gggaagctca   2940

ttgcccgatg aacttttgtt tgctgacgac tcctcagaag gctcagaagt cctgatgtga   3000
```

<210> SEQ ID NO 35
<211> LENGTH: 1587
<212> TYPE: DNA
<213> ORGANISM: Homo sapiens

<400> SEQUENCE: 35

```
atgctgttgc cgctgctgct gctgctaccc atgtgctggg ccgtggaggt caagaggccc     60

cggggcgtct ccctcaccaa tcatcacttc tacgatgagt ccaagccttt cacctgcctg    120

gacggttcgg ccaccatccc atttgatcag gtcaacgatg actattgcga ctgcaaagat    180

ggctctgacg agccaggcac ggctgcctgt cctaatggca gcttccactg caccaacact    240

ggctataagc ccctgtatat cccctccaac cgggtcaacg atggtgtttg tgactgctgc    300

gatggaacag acgagtacaa cagcggcgtc atctgtgaga acacctgcaa agagaagggc    360

cgtaaggaga gagagtccct gcagcagatg gccgaggtca cccgcgaagg gttccgtctg    420

aagaagatcc ttattgagga ctggaagaag gcacgggagg agaagcagaa aaagctcatt    480

gagctacagg ctgggaagaa gtctctggaa gaccaggtgg agatgctgcg gacagtgaag    540

gaggaagctg agaagccaga gagagaggcc aaagagcagc accagaagct gtgggaagag    600

cagctggctg ctgccaaggc ccaacaggag caggagctgg cggctgatgc cttcaaggag    660

ctggatgatg acatggacgg gacggtctcg gtgactgagc tgcagactca cccggagctg    720

gacacagatg ggatggggc gttgtcagaa gcggaagctc aggccctcct cagtggggac    780

acacagacag acgccacctc tttctacgac cgcgtctggg ccgccatcag ggacaagtac    840

cggtccgagg cactgcccac cgaccttcca gcaccttctg cccctgactt gacggagccc    900

aaggaggagc agccgccagt gccctcgtcg cccacagagg aggaggagga ggaggaggag    960

gaggaggaag aagaggctga agaagaggag gaggaggagg attccgagga ggccccaccg   1020

ccactgtcac ccccgcagcc ggccagccct gctgaggaag acaaaatgcc gccctacgac   1080

gagcagacgc aggccttcat cgatgctgcc caggaggccc gcaacaagtt cgaggaggcc   1140

gagcggtcgc tgaaggacat ggaggagtcc atcaggaacc tggagcaaga gatttctttt   1200

gactttggcc ccaacgggga gtttgcttac ctgtacagcc agtgctacga gctcaccacc   1260

aacgaatacg tctaccgcct ctgccccttc aagcttgtct cgcagaaacc caaactcggg   1320

ggctctccca ccagccttgg cacctggggc tcatggattg gccccgacca cgacaagttc   1380

agtgccatga agtatgagca aggcacgggc tgctggcagg gccccaaccg ctccaccacc   1440

gtgcgcctcc tgtgcgggaa agagaccatg gtgaccagca ccacagagcc cagtcgctgc   1500

gagtacctca tggagctgat gacgccagcc gcctgcccgg agccaccgcc tgaagcaccc   1560

accgaagacg accatgacga gctctag                                       1587
```

<210> SEQ ID NO 36
<211> LENGTH: 1716
<212> TYPE: DNA
<213> ORGANISM: Homo sapiens

<400> SEQUENCE: 36

```
atggatcgga gcaaacggaa ttcaattgca ggatttcctc cacgtgtgga gcgtcttgaa     60
```

-continued

```
gagtttgaag gaggtggtgg aggagaagga aatgtgagcc aggtgggaag agtttggcca    120
tcttcgtatc gagctcttat aagtgccttt tccagactga cgcgtttgga tgatttcacc    180
tgtgaaaaaa tagggtctgg cttcttttct gaagtgttca aggtacgaca ccgagcttct    240
ggtcaggtga tggctcttaa gatgaacaca ttgagcagta accgggcaaa catgctgaaa    300
gaagtacagc tcatgaatag actctcccat cccaacatcc ttaggttcat gggtgtatgt    360
gttcatcaag gacaattgca tgcacttaca gagtatatca actccgggaa cctggaacag    420
ttgctagaca gtaacctgca tttgccttgg actgtgaggg taaaactggc ctatgacata    480
gcagtgggcc tcagctacct tcacttcaaa ggcatttttc atcgggacct cacatctaag    540
aactgcctga taaagaggga tgagaatggt tactctgcag tggtagctga ctttggcctg    600
gctgagaaga tccccgatgt cagcatgggg agtgagaagc tggccgtggt gggttcccca    660
ttctggatgg cacctgaggt tctccgagat gagccctata atgaaaaggc agatgtgttc    720
tcttatggta tcatcctctg cgagatcatc gcccgcatcc aggccgatcc ggactatctt    780
ccccgcacag agaatttcgg gctggactat gatgctttcc agcacatggt gggagactgt    840
cccccagatt ttctgcaact tactttcaac tgctgtaaca tggatcccaa actgcgccca    900
tcttttgtgg agattgggaa gaccctggag gaaattctga gccgcctaca ggaagaagag    960
caggagaggg ataggaagct gcagcccaca gccaggggac tcttggagaa agcacctggg   1020
gtgaagcgac taagctcact ggatgacaag atcccccaca agtcaccatg cccaagacgt   1080
accatctggc tgtctcgaag ccagtcagat atcttttccc gtaagccccc acgtacagtg   1140
agtgtcttgg acccatacta ccggccacga gatggtgctg cccgcacccc caaagtcaac   1200
cctttttagtg ctcgccagga cctcatgggg ggcaagatca agtttttga cctgcccagc   1260
aagtctgtca tctctctggt atttgacctg gatgcaccag ggcccggaac tatgcccctg   1320
gctgactggc aggagcccct ggccccacct attcgccggt ggcgttcctt gcctggttcg   1380
cctgagttct tgcatcaaga ggcttgtcca tttgtgggcc gggaagaatc gctatctgat   1440
gggcccccac cacgcctaag tagtctcaag tacagagtta aagagatccc accattccgg   1500
gcatctgccc taccagctgc tcaagcccat gaggctatgg actgctccat tctccaggaa   1560
gaaaatggtt ttgggtccag gccccagggg accagtccat gccctgcggg tgcttctgag   1620
gagatggagg tagaagaaag gccagcaggc tcaactccag ccaccttctc cacctcaggc   1680
ataggcctgc aaacccaggg aaagcaggat gggtga                               1716
```

PROGNOSIS METHOD OF MULTIPLE MYELOMA

The invention relates to a diagnosis method of multiple myeloma.

Multiple Myeloma (MM) account for approximately 10% of hematological malignancies and is therefore the second most common hematological disorder. Despite relative homogenous symptoms among patients, this condition characterized by the clonal accumulation of malignant plasma cells in the bone marrow, has a highly heterogeneous genetic and molecular profile. Thus, in addition to multiple genetic abnormalities, by using high throughput gene expression profiling newly diagnosed patients can be classified in at least 7 molecular groups. Active research on MM allowed great improvement in new treatments discovery, including proteasomes inhibitors or immunomodulatory agents that enhanced significantly the patients median survival from 3-4 years in the 90's to 7-8 years nowadays.

However there is a vital need for additional therapies since until today MM is a condition that cannot be cured, and all patients finally relapse, Kinases are key actors in various cancers where they play at different level, expanding proliferation, survival, migration but also mediating resistances to treatment, which makes them particularly attractive for the development of new specific inhibitors. Thus, targeting kinases is especially relevant to improve patients life and as certainly a role to play also in MM. Indeed, whereas major signaling pathways have been studied in myeloma, they only represent a small proportion of the whole kinome. Considering the numbers of kinases inhibitors currently used, under development or already in clinical trial for other diseases, studying the impact of the kinome in MM is then highly pertinent.

A first study by Tiedemann et al. started to investigate kinome in this pathology by using a high-throughput systematic RNA interference approach in Human Myeloma Cell Lines (HMCLs). They thus identified new potential targets for MM therapy.

However, alternative methods are still required.

The invention intends to obviate this lack in the art.

One object of the invention is to provide a new efficient prognosis method of multiple myeloma, Another object of the invention is also to provide a new therapy for treating patients having a poor outcome.

The invention relates to a method for predicting, preferably in vitro, the outcome of an individual afflicted by a multiple myeloma, said method comprising the steps of:

a—measuring, in a biological sample from said individual, the expression level of at least 6 genes chosen among a group of 28 genes, said 28 genes belonging to a set of 36 genes, said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK, said set of 36 genes consisting of AZU1, CDKN1A, DDR1, HK3, MAP4K2, MERTK, PRKCSH, TESK2, AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK;

said expression level being normalized compared to said 36 genes in order to obtain a normalized expression level for each of said at least 6 genes, b—calculating an index KI, said KI representing the sum of the normalized expression level obtained for each of said at least 6 genes c—classifying the individual such that:

I. if the index KI is higher than a reference value, the individual is likely to have a bad outcome, and II. if the score value is lower than a reference value, the individual is likely to have a good outcome, said reference value being 0.44.

The inventors have identified a set of 36 genes and/or proteins, which are differentially expressed in individuals having a multiple myeloma as compared to healthy individuals. Among these genes, 8 of them are the hallmark of a good prognosis of multiple myeloma (good outcome) and 28 are associated with a bad prognosis of multiple myeloma (bad outcome).

As a consequence, the set of 36 genes identified by the inventors, which has never been associated together with multiple myeloma, can be divided into a group of 28 bad prognosis genes/proteins and a group of 8 good prognosis genes.

In the present invention, the term "individual" refers to a mammal individual, preferably a human individual.

In the invention "multiple myeloma" refers to a cancer of plasma cells, i.e. white blood cell that normally produce antibodies. The multiple myeloma disease is defined by class C90.0 in accordance with the International Classification of Diseases World Health Organisation Classification ($10^{th}$ revised edition; 2016). Such pathology is well known in the art.

The term "outcome" refers to the survival, the relapse or the death of the individual. The outcome may relate to disease-free survival (DFS), event free survival (EFS) or overall survival (OS), as defined within the state of the art. Illustratively, a "bad outcome" may refer to a disease relapse or death of the individual. Oppositely, a "good outcome" may refer to survival of the individual, with or without relapse episode.

Recent advances in treatment have led to a median overall survival of intensively-treated patients of 6-7 years and an event-free survival of 3-4 years. However, patients invariably relapse after multiple lines of treatment, with shortened intervals between relapses, and finally become resistant to all treatments, resulting in loss of clinical control over the disease.

In the invention, a "biological sample" refers to a biological sample obtained, reached, collected or isolated from an individual, in vivo or in situ. Such samples may be, but not limited to, organs, tissues, fractions and cells isolated from an individual. For example, suitable biological samples include but are not limited to a cell culture, a cell line, a tissue biopsy such as a bone marrow aspirate, a biological fluid such as a blood, pleural effusion or a serum sample, and the like. An advantageous biological sample includes but is not limited to a blood sample, a tissue biopsy, including a bone marrow aspirate. The biological sample as defined in the invention may be a crude sample, or may be purified to various degrees prior to storage, processing, or measurement.

In the invention, the expression level of at least 6 genes chosen among the group of 28 is sufficient to evaluate the outcome of an individual afflicted by multiple myeloma.

Step a).

First, the expression level of the genes is measured by well-known protocol known in the art. These methods are for instance, DNA-CHIPs containing probesets of said at least 6 genes, so that an expression level can be determined for each of said at least 6 genes. Other methods can be used, such that quantitative PCR strategy by using specific couples of primers for each of said at least 6 genes, with either a specific Taqman probe for each of said at least 6 genes, or SYBR® compounds.

Advantageously, the expression level can be evaluated by measuring the expression level of mRNA for each of the genes of interest. This measurement may be carried out by using the well-known techniques available in the art. In this case, mRNA may be extracted, for example using lytic enzymes or chemical solutions or extracted by commercially available nucleic-acid-binding resins following the manufacturer's instructions. Extracted mRNA may be subsequently detected by hybridization, such as Northern blot, and/or amplification, such as quantitative or semi-quantitative RT-PCR. Other methods of amplification include ligase chain reaction (LCR), transcription-mediated amplification (TMA), strand displacement amplification (SDA) and nucleic acid sequence based amplification (NASBA).

Advantageously, the level of mRNA expression for each of the genes of interest may be measured by the mean of quantification of the cDNA synthesized from said mRNA, as a template, by one reverse transcriptase. Methods for determining the quantity of mRNA by microarrays or by RNA sequencing may also be used.

In certain embodiments, complexes between the double-stranded nucleic acids resulting from amplification and fluorescent SYBR® molecules may be obtained and then the fluorescence signal generated by the SYBR® molecules complexed with the said amplified nucleic acids may be measured.

To determine the expression level of said at least 6 genes could be to carry out by a northern blot analysis, but due to the low efficiency of such a method, the skilled person will prefer the quantitative methods to obtain a more precise expression level of said at least 6 genes.

In the invention, the set of 36 genes is the following ones, and the Ensembl data base accession numbers, and the sequence of the CDS (or one of the CDS if the gene expression different variants) are represented in the following table:

TABLE 1

| Gene | Ensembl accession number | CDS SEQ ID |
|---|---|---|
| AURKA | Ensembl: ENSG00000087586 | SEQ ID NO: 1 |
| BUB1 | Ensembl: ENSG00000169679 | SEQ ID NO: 2 |
| BUB1B | Ensembl: ENSG00000156970 | SEQ ID NO: 3 |
| CDC7 | Ensembl: ENSG00000097046 | SEQ ID NO: 4 |
| CDKN2C | Ensembl: ENSG00000123080 | SEQ ID NO: 5 |
| CDKN3 | Ensembl: ENSG00000100526 | SEQ ID NO: 6 |
| CHEK1 | Ensembl: ENSG00000149554 | SEQ ID NO: 7 |
| CKS1B | Ensembl: ENSG00000173207 | SEQ ID NO: 8 |
| CKS2 | Ensembl: ENSG00000123975 | SEQ ID NO: 9 |
| DBF4 | Ensembl: ENSG00000006634 | SEQ ID NO: 10 |
| DUSP10 | Ensembl: ENSG00000143507 | SEQ ID NO: 11 |
| HK2 | Ensembl: ENSG00000159399 | SEQ ID NO: 12 |
| PI4K2B | Ensembl: ENSG00000038210 | SEQ ID NO: 13 |
| MAP2K6 | Ensembl: ENSG00000108984 | SEQ ID NO: 14 |
| MELK | Ensembl: ENSG00000165304 | SEQ ID NO: 15 |
| NEK2 | Ensembl: ENSG00000117650 | SEQ ID NO: 16 |
| NTRK3 | Ensembl: ENSG00000140538 | SEQ ID NO: 17 |
| PAK2 | Ensembl: ENSG00000180370 | SEQ ID NO: 18 |
| PBK | Ensembl: ENSG00000168078 | SEQ ID NO: 19 |

TABLE 1-continued

| Gene | Ensembl accession number | CDS SEQ ID |
|---|---|---|
| PFKP | Ensembl: ENSG00000067057 | SEQ ID NO: 20 |
| PLK4 | Ensembl: ENSG00000142731 | SEQ ID NO: 21 |
| PTPRG | Ensembl: ENSG00000144724 | SEQ ID NO: 22 |
| RPRD1A | Ensembl: ENSG00000141425 | SEQ ID NO: 23 |
| SRPK1 | Ensembl: ENSG00000096063 | SEQ ID NO: 24 |
| SRPK2 | Ensembl: ENSG00000135250 | SEQ ID NO: 25 |
| STK39 | Ensembl: ENSG00000198648 | SEQ ID NO: 26 |
| TK1 | Ensembl: ENSG00000167900 | SEQ ID NO: 27 |
| TTK | Ensembl: ENSG00000112742 | SEQ ID NO: 28 |
| AZU1 | Ensembl: ENSG00000172232 | SEQ ID NO: 29 |
| CDKN1A | Ensembl: ENSG00000124762 | SEQ ID NO: 30 |
| DDR1 | Ensembl: ENSG00000204580 | SEQ ID NO: 31 |
| HK3 | Ensembl: ENSG00000160883 | SEQ ID NO: 32 |
| MAP4K2 | Ensembl: ENSG00000168067 | SEQ ID NO: 33 |
| MERTK | Ensembl: ENSG00000153208 | SEQ ID NO: 34 |
| PRKCSH | Ensembl: ENSG00000130175 | SEQ ID NO: 35 |
| TESK2 | Ensembl: ENSG00000070759 | SEQ ID NO: 36 |

The genes 8 associated with a good prognosis value are the following ones AZU1, CDKN1A, DDR1, HK3, MAP4K2, MERTK, PRKCSH and TESK2, and the 28 genes associated with a good prognosis value are AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK. From the above table, the skilled person can assign the Ensembl accession number and the SEQ ID NO to each gene of said 2 groups of 8 and 28 genes respectively.

Thus, according to the invention, in the first step of the method detailed above, the expression level of at least 6 genes among the above defined 28 genes is determined by well know technics as mentioned above.

Since the method gives some raw data regarding the expression of said at least 6 genes, and in order to compare all the measured expression value, all these values are normalized. The normalization is carried out compared to a reference cohort of patients afflicted by multiple myeloma for which the expression level of all the 36 genes was established. Therefore, taking account of the data provided by the reference cohort, the expression level of each of said at least 6 genes can be normalized or standardized according to a standard score protocol.

In statistics, the KI is: Σ((BAD prognosis gene standardized expression)−Σ(GOOD prognosis gene standardized expression) were standardized expression is the reduced centred normal distribution for gene values.

By at least 6 genes, chosen among 28 genes, it is meant in the invention that 6, or 7, or 8, or, 9, or 10, or 11, or 12, or 13, or 14, or 15, or 16, or 17, or 18, or 19, or 20, or 21, or 22, or 23, or 24, or 25, or 26, or 27, or 28 genes can be studied.

More precisely the invention mentions that at least 6 genes chosen among a group of 28 genes that belong to a set of 36 genes. When less than 8 genes are chosen, only the group of 28 genes have to be considered. This is because in the set of 36 genes, 8 genes are associated to a good prognosis. However, when at least 9 genes are evaluated, and the expression of which is measured, the set of 36 gene have to be considered, i.e. the at least 9 genes can be chosen among the set of 36 genes. However, it is most advantageous that until 28 genes, the gens be selected from the group of said 28 genes In other words, in step a) of the method defined above, consists of measuring the expression level of at least 6 genes chosen among a group of 28 genes said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

Advantageously, in step a) of the method defined above, consists of measuring the expression level of at least 7 genes chosen among a group of 28 genes said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

Advantageously, in step a) of the method defined above, consists of measuring the expression level of at least 8 genes chosen among a group of 28 genes said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

Advantageously, in step a) of the method defined above, consists of measuring the expression level of at least 9 genes chosen among a group of 28 genes said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

Advantageously, in step a) of the method defined above, consists of measuring the expression level of at least 10 genes chosen among a group of 28 genes said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

When choosing the at least 6 genes, all the combination can be made.

More advantageously, it is relevant that the list of said at least 6 genes contains at least one of the 6 following genes: CHEK1, DBF4, MELK, PBK, PLK4 and TTK, preferably at least one of the 7 following genes CHEK1, DBF4, MELK, PBK, PLK4, SRPK1 and TTK, more preferably at least one of 10 following genes BUB1B, CHEK1, CKS2, DBF4, HK2, MELK, PBK, PLK4, SRPK1 and TTK.

Advantageously, step a) consists of selecting at least the 6 following genes CHEK1, DBF4, MELK, PBK, PLK4 and TTK among the group of 28 genes, said group consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

More advantageously, step a) consists of selecting at least the 7 following genes CHEK1, DBF4, MELK, PBK, PLK4, SRPK1 and TTK among the group of 28 genes, said group consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK.

In another advantageous embodiment, step a) consists of selecting at least 6 genes, at least one of said at least 6 gene being chosen from the group consisting of the genes defined by the sequences as set forth in SEQ ID NO: 7, SEQ ID NO: 10, SEQ ID NO: 15, SEQ ID NO: 19, SEQ ID NO: 21 and SEQ ID NO: 28.

In still another advantageous embodiment, step a) consists of selecting at least the genes defined by the sequences as set forth in SEQ ID NO: 7, SEQ ID NO: 10, SEQ ID NO: 15, SEQ ID NO: 19, SEQ ID NO: 21 and SEQ ID NO: 28.

In the invention, it is meant by "gene defined by sequence" a gene which is represented by at least the sequence mentioned. In other words, the SEQ ID NO is not limitative but allows the skilled person to identify the gene that he should consider to carry out the invention.

Step b).

In the above method, when the expression level of said at least 6 gene was measured and normalized, step b) is carried out. Step b) consist to sum the normalized value for each of said at least 6 genes to obtain an index which is called Kinase Index or KI. The KI index calculation and definition is mentioned hereafter in the Example.

When considering the group of at least 6 genes chosen among the group of 28 genes, the KI calculation will be the sum of the normalized value of each of the genes taken into consideration.

Step c).

When the KI is calculated as mentioned above, it is proposed to classify the biological sample from which the gene expression levels were measured either as a good outcome or bad outcome.

To carry out this classification, the KI is compared to a reference value. This reference value is calculated by a Maxstat (Hothorn and Lausen, 2003) analysis, such that, in a reference cohort Maxstat statistic results segregates the samples of into two groups with 31% of the samples with a KI>reference value and 69% of the sample with a KI s reference value.

When considering 6 genes as defined above, i.e. 6 genes chosen among the group of 28 genes, the reference value is 0.44, in particular when the 6 genes are the following ones: CHEK1, DBF4, MELK, PBK, PLK4 and TTK, the reference value is 0.44.

Thus, if the KI calculated in step b) is higher than 0.44, i.e. if the sum of the normalized expression of said at least 6 genes is higher than 0.44, then the biological sample, and by extension the individual from which it derives, is considered to have a bad outcome. On the contrary, if the KI calculated in step b) is lower than 0.44, i.e. if the sum of the normalized expression of said at least 6 genes is lower than 0.44, then the biological sample, and by extension the individual from which it derives, is considered to have a good outcome.

Advantageously, the invention relates to the method as defined above, wherein step a. is a step of measuring the expression level of at least 10 genes chosen among said group of 28 genes, said reference value being 0.79.

In this advantageous embodiment, the expression level of at least 10 genes is measured, and normalized in step a), the KI is calculated in step b), and the classification is carried out in step c). The classification is more efficient if the reference value is adapted to said at least 10 gene, and be equal to 0.79.

It is advantageous that said at least 10 genes include the 6 following genes CHEK1, DBF4, MELK, PBK, PLK4 and TTK.

It is more advantageous that said at least 10 genes be the following ones: BUB1B, CHEK1, CKS2, DBF4, HK2, MELK, PBK, PLK4, SRPK1 and TTK.

Advantageously, the invention relates to the method as defined above, wherein step a. is a step of measuring the expression level of at least 28 genes of said group of 28 and said reference value being 1.31.

In this advantageous embodiment, the expression level of at least 28 genes is measured, and normalized in step a), the KI is calculated in step b), and the classification is carried out in step c). The classification is more efficient if the reference value is adapted to said at least 28 genes, and be equal to 1.31.

The 28 genes are the ones mentioned above.

More advantageously, the invention relates to the method as defined above, wherein step a. is a step of measuring the expression level of all the genes of said set of 36 genes, and wherein said reference value is 2.1.

In this advantageous embodiment, all the expression level of all the genes of the set of 36 is measured. Since the set of 36 genes contains good outcome genes, the KI calculation is as defined in Example, i.e. the sum of the expression level of the 28 genes minus the sum of the expression level of the 8 genes, such as defined above.

The best reference value, when considering the entire set of 36 genes is 2.1, as shown in the Example.

The invention also relates to composition comprising at least a specific inhibitor of one at least of the following kinases: MELK, PBK, CHK1, SRPK1, DBF4 and PLK4, or a combination thereof, for its use for the treatment of an individual afflicted by a multiple myeloma having a bad outcome, as identified by the method according to the above definition and overexpressing said kinases.

The inventors identify that, in multiple myeloma samples in which a kinase of the group of MELK, PBK, CHK1, SRPK1, DBF4 and PLK4 is expressed abnormally over expressed, a treatment with an inhibitor of said kinases induces either apoptosis or cell cycle arrest.

By over expressed, it is meant in the invention that the corresponding gene is expressed at a level higher compared to the expression of the same gene in a non multiple myeloma sample, in particular in an healthy sample.

The inventors therefore propose to use specific inhibitors of the kinases MELK, PBK, CHK1, SRPK1, DBF4 and PLK4, to treat patients afflicted by multiple myeloma, in particular in patients afflicted by multiple myelomas, the cells of which overexpressing said kinases MELK, PBK, CHK1, SRPK1, DBF4 and PLK4.

The composition above mentioned may comprise the following 54 formulations:

TABLE 2

| formulation | CHK1 inhibitor | DBF4 inhibitor | MELK inhibitor | PBK inhibitor | PLK4 inhibitor | SRPK1 inhibitor |
|---|---|---|---|---|---|---|
| 1 | + | | | | | |
| 2 | | + | | | | |
| 3 | | | + | | | |
| 4 | | | | + | | |
| 5 | | | | | + | |
| 6 | | | | | | + |
| 7 | + | + | | | | |
| 8 | + | | + | | | |
| 9 | + | | | + | | |
| 10 | + | | | | + | |
| 11 | + | | | | | + |
| 12 | | + | + | | | |
| 13 | | + | | + | | |
| 14 | | + | | | + | |
| 15 | | + | | | | + |
| 16 | | | + | + | | |
| 17 | | | + | | + | |
| 18 | | | + | | | + |
| 19 | | | | + | + | |
| 20 | | | | + | | + |
| 21 | | | | | + | + |
| 22 | + | + | + | | | |
| 23 | + | + | | + | | |
| 24 | + | + | | | + | |
| 25 | + | + | | | | + |
| 26 | + | | + | + | | |
| 27 | + | | + | | + | |
| 28 | + | | + | | | + |
| 29 | + | | | + | + | |
| 30 | + | | | + | | + |
| 31 | + | | | | + | + |
| 32 | | + | + | + | | |
| 33 | | + | + | | + | |
| 34 | | + | + | | | + |
| 35 | | + | | + | + | |
| 36 | | + | | + | | + |
| 37 | | + | | | + | + |
| 38 | | | + | + | + | |
| 39 | | | + | + | | + |
| 40 | | | | + | + | + |
| 41 | + | + | + | + | | |
| 42 | + | + | + | | + | |
| 43 | + | + | | | | + |
| 44 | + | + | | + | + | |
| 45 | + | + | | + | | + |
| 46 | + | + | | | + | + |
| 47 | | + | + | + | + | |
| 48 | | + | + | + | | + |
| 49 | | + | | + | + | + |
| 50 | | | + | + | + | + |
| 51 | + | + | + | + | + | |
| 52 | + | + | + | + | | + |
| 53 | | + | + | + | + | + |
| 54 | + | + | + | + | + | + |

Advantageously, the invention relates to the composition as defined above, in association with an anti-multiple myeloma therapy, such as at least a drug commonly used for treating multiple myeloma, and possibly for which some resistance occurs.

In the invention, "a drug commonly used for treating multiple myeloma" refers to anticancer drugs or compounds.

Advantageously, anticancer compounds may include a chemo drug, in particular selected in a group comprising melphalan, vincristine, cyclophosphamide, etoposide, doxorubicin, liposomal doxorubicin, bendamustine. Moreoever, anticancer compounds may include a corticosteroid, in particular selected in a group comprising dexamethasone and prednisone.

Advantageously, anticancer compounds may include a proteasome inhibitor, in particular selected in a group comprising bortezomib, carfilzomib and ixazomib.

Advantageously, anticancer compounds may include a histone deacetylase (HDAC) inhibitor, in particular panobinostat.

Anticancer compounds may also include a monoclonal antibody, in particular selected in a group comprising daratumumab, a monoclonal anti CD38 antibody, and elotuzumab, monoclonal antibody directed against the SLAMF7 receptor.

Thus, the 54 above formulation may be associated with an anti-multiple myeloma therapy. Te multy therapy according to the invention is therefore constituted by the above kinase inhibitors and any of anti-multiple myeloma conventional and non-conventional therapy known in the art.

More advantageously, the invention relates to the composition as defined above, wherein said drug used for treating multiple myeloma is lenalidomide, melphalan, bortezomib and thalidomide.

More advantageously, the invention relates to the composition above mentioned, wherein the specific inhibitor is chosen among the following ones: OTSSP167, HITOPK032, AZD7762, SRPIN340, XL413 and Centrinone B/LCR 323.

OTSSP167 is a MELK specific inhibitor having the following formula $C_{25}H_{28}Cl_2N_4O_2$ (CAS number: 1431697-89-0).

HITOPK032 is a PBK specific inhibitor having the following formula $C_{20}H_{11}N_5OS$ (CAS number: 487020-03-1)

AZD7762 is a CHK1 inhibitor having the following formula $C_{17}H_{19}FN_4O_2S$. HCl (CAS number: 1246094-78-9).

XL413 is a specific inhibitor of DBF4 having the following formula $C_{14}H_{12}ClN_3O_2$.xHCI (CAS number 1169562-71-3)

SRPIN340 is an inhibitor of SRPK1 having the following formula $C_{18}H_{18}F_3N_3O$ (CAS number: 218156-96-8).

Centrinone B is a specific inhibitor of PLK4 having the following formula $C_{27}H_{27}F_2N_7O_5S_2$ (CAS number: 1798871-31-4).

More advantageously, the invention relates to the composition above mentioned, said composition being chosen among the following ones: melphalan and one at least of OTSSP167, AZD7762, HITOPK032, and XL413, or lenalidomide and one at least of OTSSP167, AZD7762, HITOPK032, and XL413.

More advantageously, the invention relates to the composition as defined above, wherein said a multiple myeloma having a bad outcome are lenalidomide- or melphalan-resistant multiple myeloma.

Lenalidomide- or melphalan-resistant multiple myeloma are multiple myeloma developed in individual that relapse despite a treatment with lenalidomide or melphalan drugs respectively.

Advantageously, the invention relates to the composition as defined above, wherein said drug used for treating multiple myeloma and said inhibitor are used simultaneously, separately, or sequentially.

By a simultaneous use, it is meant in the invention that all the compounds are injected or administered to an individual at the same time. Separately use means that the compounds are provided in a separate formulation but are injected or administered at the same time. Sequentially means that the compounds are delivered to the individual separately over the time.

The invention also relates to a method for treating an individual afflicted by a multiple myeloma having a bad outcome, as identified by the method according to the above definition and overexpressing the following kinases: MELK, PBK, CHK1, SRPK1, DBF4 and PLK4, said method comprising a step of administering in said patient an effective amount of at least a specific inhibitor of one at least of the following kinases: MELK, PBK, CHK1, SRPK1, DBF4 and PLK4.

The invention also relates to the above method, wherein the effective amount of at least a specific inhibitor of one at least of the following kinases: MELK, PBK, CHK1, SRPK1, DBF4 and PLK4 is associated with an anti multiple myeloma therapy.

The invention also relate to the use of a composition comprising at least a specific inhibitor of one at least of the following kinases: MELK, PBK, CHK1, SRPK1, DBF4 and PLK4, or a combination thereof, for inducing apoptosis and/or proliferation inhibition of primary multiple myeloma cells in vitro culture or multiple myeloma cell lines.

The inventors have identified that the above inhibitors are able to induce apoptosis or to inhibit cell cycle of primary multiple myeloma cells from patients or myeloma cell lines.

Advantageously, the invention relates to the above mentioned use, in association with at least a drug used for treating multiple myeloma, and possibly for which some resistance occur.

Resistance to a drug, regarding multiple myeloma, means that said drug is not able to affect survival and/or proliferation of the cells that constitute multiple myelomas. If a resistance occurs, it means that the multiple myeloma was initially sensitive to the drug, but further to the treatment, or during the treatment, mutations may occur, and the target of the drugs are not any more sensitive to the drug. Therefore, the cells become insensitive to the drug and a resistance appears.

Finally, the invention also relates to a composition comprising a drug used for treating multiple myeloma, and possibly for which some resistance occurs, and at least a specific inhibitor of one at least of the following kinases: MELK, PBK, CHK1, SRPK1, DBF4 and PLK4, or a combination thereof, possibly in association with a pharmaceutically acceptable vehicle.

The composition comprises, in a pharmaceutical acceptable vehicle, an at least an inhibitor of at least one of the above listed kinases and a at least a conventional drug commonly used for treating multiple myeloma, in particular drugs for which resistance may occur.

Advantageously, said drug is selected in a group comprising thalidomide, lenalidomide, pomalidomide and derivatives thereof.

Within the scope of the invention, the term "derivative of" is intended to refer to a compound having structural and functional analogy with a compound of interest.

It is within the skills of a physician to determine the specific therapeutically effective dosage regimen, as this dosage regimen will be dependent upon a variety of factors including, but not limited to: the stage of the multiple myeloma and the severity of the disease; the age; the body weight; general health; the sex; the diet; the time course of administration; the route of administration; the duration of the treatment; the drugs that are concomitantly administered in combination with the pharmaceutical composition within the scope of the present invention.

In some embodiments, the dosage regimen said at least one inhibitor and said drug may range from about 0.0001 mg to about 1,000 mg per adult, per day. Preferably, the individual is administered with an amount of about 0.0001, 0.0005, 0.001, 0.005, 0.01, 0.05, 0.1, 0.5, 1.0, 2.5, 5.0, 7.5, 10.0, 15.0, 20.0, 25.0, 50.0, 75.0, 100, 250, 500 and 750 mg of said drug and said inhibitor in order to adjust the dosage regimen that is the most suitable to a particular individual in need of the treatment.

A pharmaceutical composition within the scope of the present invention may contain from about 0.01 mg to about 500 mg of said drug and said at least one inhibitor, preferably from about 1 mg to about 100 mg of said drug and said at least one inhibitor.

In a preferred embodiment, an effective amount of said inhibitor and said at least one inhibitor is routinely administered to an individual in need thereof, at a dosage regimen from about 0.0002 mg/kg to about 20 mg/kg of body weight per day, in particular from about 0.001 mg/kg to 7 mg/kg of body weight per day.

The optimal amount of said inhibitor and said at least one inhibitor to be comprised in a pharmaceutical dosage unit according to the invention may be easily adapted by the one skilled in the art using routine known protocols or methods.

Said inhibitor and said at least one inhibitor and the pharmaceutical composition comprising thereof disclosed herein may be administered by any suitable route, i.e. including, but not limited to, an oral, sublingual, buccal, subcutaneous, transdermal, topical, intraperitoneal, intramuscular, intravenous, subdermal, intrathecal and intranasal and rectal administration.

The invention also relates to a method for determining the stage of a multiple myeloma disease in an individual having multiple myeloma, comprising the steps of:

a—measuring, in a biological sample from said individual, the expression level of at least 6 genes chosen among a group of 28 genes, said 28 genes belonging to a set of 36 genes, said group of 28 genes consisting of the genes AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK, said set of 36 genes consisting of AZU1, CDKN1A, DDR1, HK3, MAP4K2, MERTK, PRKCSH, TESK2, AURKA, BUB1, BUB1B, CDC7, CDKN2C, CDKN3, CHEK1, CKS1B, CKS2, DBF4, DUSP10, HK2, P14K2B, MAP2K6, MELK, NEK2, NTRK3, PAK2, PBK, PFKP, PLK4, PTPRG, RPRD1A, SRPK1, SRPK2, STK39, TK1 and TTK, said expression level being normalized compared to said 36 genes in order to obtain a normalized expression level for each of said at least 6 genes, b—calculating an index KI, said KI representing the sum of the normalized expression level obtained for each of said at least 6 genes c—classifying the said individual as being an early stage individual, an intermediate stage individual or a late stage individual, by comparing the score value obtained at step b) with a reference score value, said reference score value being 0.44.

Advantageously, the expression level of at least 6 genes as defined above is measured at step a).

Advantageously, the expression level of at least 10 genes as defined above is measured at step a), and reference score value is 0.79.

Advantageously, the expression level of at least 28 genes as defined above is measured at step a), and reference score value is 1.31.

Advantageously, the expression level of the 36 genes as defined above is measured at step a), and reference score value is 2.1.

Within the scope of the present invention, "early stage", "intermediate stage" and "late stage" may refer to one of the stage commonly used in the art to classify the individuals having a multiple myeloma with respect of the advancement of the disease.

Illustratively, the stage of the multiple myeloma disease may refer to the stage as determined by the Durie-Salmon system.

According to this system, there are three stages, stages I (1), II (2) or III (3). For example, stage I refers to multiple myeloma without symptoms, because there are fewer cancer cells in the body. Stage I may be characterized by (i) a number of red blood cells within or slightly below normal range; (ii) normal amount of calcium in the blood; low levels of M protein in the blood or urine; M protein below g/dL for IgG; below 3 g/dL for IgA; below 4 g/24 h for urinary light chain; and no bone damage on X-rays.

Stage II of multiple myeloma is featured by more cancer cells in the body of the individual. Criteria for stage II are defined as those that fit neither stage I nor stage III.

Stage III of multiple myeloma is featured by many cancer cells in the body of the individual. Stage III may be characterized by (i) anaemia, namely a haemoglobin less than 8.5 gm/dL; (ii) hypercalcemia, (iii) advanced bone damages; (iv) high levels of M protein in the blood or urine, in particular M protein above 7 g/dL for IgG, above 5 g/dL for IgA and above 12 g/24 h for urinary light chain.

Advantageously, early stage may refer to stage I according to the Durie-Salmon system.

Advantageously, intermediate stage may refer to stage II according to the Durie-Salmon system.

Advantageously, late stage may refer to stage III according to the Durie-Salmon system.

Advantageously, "early stage", "intermediate stage" and "late stage" may refer to the International Staging System (ISS), which relies upon data collected from patients with multiple myeloma worldwide. Similarly to the Durie-Salmon system, the ISS has three stages, mainly based on the measurement of the levels of the serum albumin and the serum β2 microglobulin (β2-M).

Accordingly to the ISS, stage I relates to a level of β2-M of less than 3.5 mg/L and a level of albumin greater than or equal to 3.5 gm/dL. Stage II may be defined by either a level of β2-M greater than 3.5 mg/L but not greater than 5.5 mg/dL and/or a level of albumin less than 3.5 g/dL. Stage III is characterized by a level of β2-M greater than 5.5 mg/L.

Advantageously, early stage may refer to stage I according to the ISS.

Advantageously, intermediate stage may refer to stage II according to the ISS.

Advantageously, late stage may refer to stage III according to the ISS.

Advantageously, the methods disclosed herein may be used in order to stage (re-stage) the disease in individuals having a recurrent or relapsed multiple myeloma, i.e. a multiple myeloma that returns after a period of being in control, e.g. after a therapeutic treatment.

EXAMPLE

1—Introduction

Figure 1:
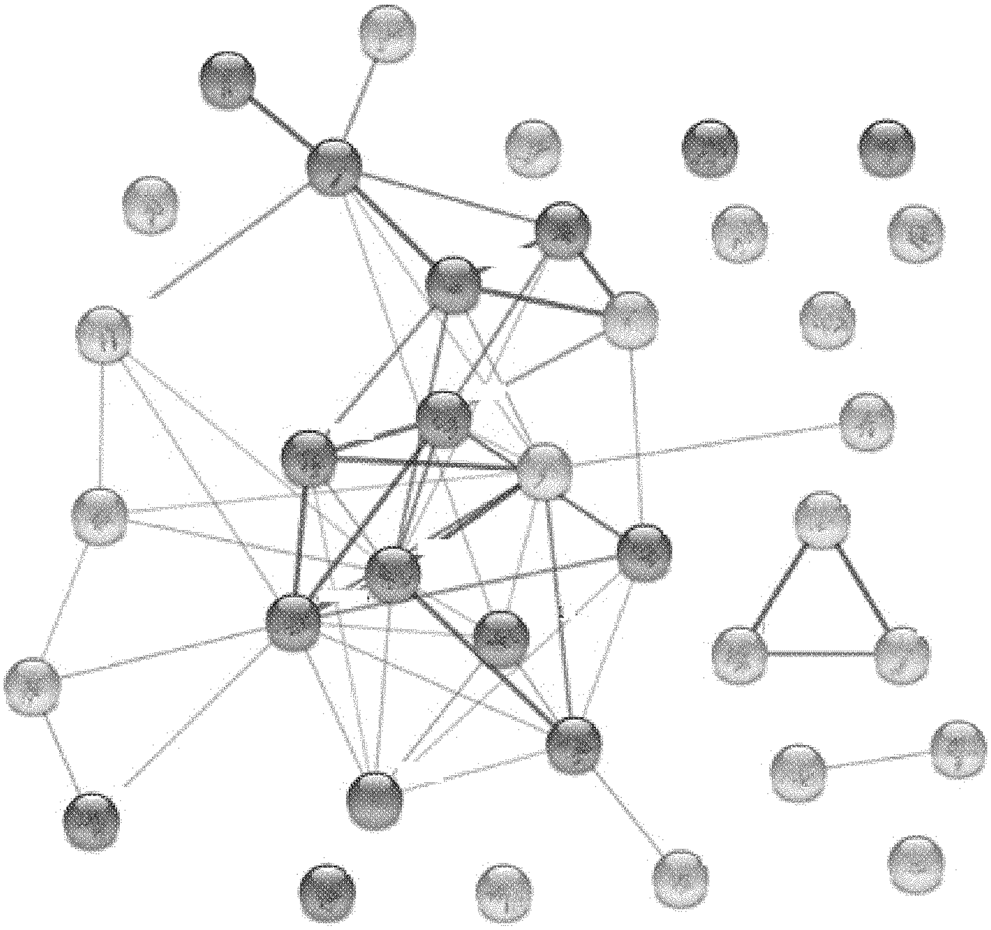
FIG. 1 represents string network of the 36psets (in dark grey cell cycle related kinases).

Multiple Myeloma (MM) account for approximately 10% of hematological malignancies and is therefore the second most common hematological disorder (Siegel et al., 2012). Despite relative homogenous symptoms among patients, MM IS characterized by the clonal accumulation of malignant plasma cells in the bone marrow (Kyle and Rajkumar, 2004) and has a highly heterogeneous genetic and molecular profile. Thus in addition to multiple genetic abnormalities, by using high throughput gene expression profiling newly diagnosed patients can be classified in at least 7 molecular groups (Zhan et al., 2006). Active research on MM allowed great improvement in new treatments discovery, including proteasomes inhibitors or immunomodulatory agents, that enhanced significantly the patient's median survival from 3-4 years in the 90's to 7-8 years nowadays (Anderson, 2012; Rollig et al., 2015). However, there is a vital need for additional therapies since until today MM is a condition that cannot be cured, and all patients finally relapse (Anderson and Carrasco, 2011).

Kinases are key actors in various cancers where they play at different level, expanding proliferation, survival, migration but also mediating resistances to treatment (Fleuren et al., 2016). Thus, targeting kinases is especially relevant to improve life of patients with cancer and numbers of kinases inhibitors are currently used, under development or already in clinical trial in cancers, and they certainly have a role to play also in MM. Indeed, whereas major signaling pathways have been studied in myeloma, they only represent a small proportion of the whole kinome (Abramson, 2016).

A first study by Tiedemann et al. started to investigate kinome in this pathology by using a high-throughput systematic RNA interference approach in Human Myeloma Cell Lines (HMCLs). They thus identified new potential targets for MM therapy (Tiedemann et al., 2010). Here we aimed to use the opposite strategy, starting with in silico analysis to identified key targets. We used a probe sets (psets) list of kinases or kinases related genes (Sabatier et al., 2011), and investigate the impact of the kinome expression in MM patients prognosis. We identified 36 kinases significantly involved in patient's outcome in three independent cohorts of patients, and analyzed further the potential impact of selected available kinases inhibitors in HMCLs and primary human myeloma cells. We thus identified new kinases with clinical interest in MM and demonstrated the potential interest of developing new kinases inhibitors for MM treatment.

2—Methods

We used the gene expression profiling (GEP) from three independent cohorts constituted of MM cells (MMCs) purified from untreated patients: the Heidelberg-Montpellier of 206 patients (ArrayExpress public database under accession number E-MTAB-362) (Hose et al., 2011; Moreaux et al., 2012), the UAMS-TT2 cohort of 345 patients from the University of Arkansas for Medical Sciences (UAMS, Little Rock, Ark., USA; accession number) (Barlogie et al., 2006), and the UAMS-TT3 cohort of 158 patients (E-TABM-1138, accession number GSE4583) (Nair et al., 2010). Gene expression data were normalized with the MASS algorithm and processing of the data was performed using the webtool genomicscape (http://www.genomicscape.com) (Kassambara et al., 2015). STRING webtool (https://strino-db.org) was used to evaluate interconnections between genes and involved pathways. Cluster (v2.11) and Tree View were used to vizualize gene expression data Kinome Index A list of 661 Affymetrix psets of kinases or kinases related genes have been extracted from literature (Sabatier et al., 2011), and challenged in the HM cohort for OS prognostic values The prognostic value of each of the genes was computed using maximally selected rank test from R package MaxStat. After Benjamini Hochberg multiple testing correction a list of 104 significant prognostic genes has been extracted. This second list has then been challenged for similar prognosis value in the UAMS-TT2 validation cohort. 72psets were thus extracted that have been then challenged for similar prognostic value in the UAMS-TT3 second validation cohort. A final list of 36 psets was then obtained representing psets associated with similar prognostic values in the three cohorts. Each pset value was standardized and the Kinome Index (called KI) was built using the following equation:

KI=Σ(BAD prognosis gene standardized expression)−Σ(GOOD prognosis gene standardized expression).

Maxstat analysis of the KI in HM cohort determined a cutoff of 2.1, with KI>2.1 is associated with BAD prognosis and KI<2.1 is associated with good prognosis.

Human Myeloma Cell Lines (HMCLs) Treatments and Viability Test.

AMO-1 and OPM2 HMCLs were purchased from DSMZ (Braunschweig, Germany), XG1 and XG21 were obtained as described (Moreaux et al., 2011). HMCLs were cultured in RPMI 1640 medium, 10% FCS (control medium). For XG-IL-6 dependent HMCLs 2 ng/ml IL-6 was added. Cells were cultured in 96-well flat-bottom microtiter plates in the presence of a concentration range of selected compounds: AZD7762 and OTSSP167 (Selleck, euromedex), HITOPK032, XL413, SRPIN340 (Sigma), AZ3146, Centrinone B (Tocris). Cell Titer Glo Luminescent Assay (Promega, Madison, Wis., USA) was used to assess cell viability, and the 50% inhibition (IC50) was determined using GraphPad Prism software (http://www.graphpad.com/scientific-software/prism/).

Cell Cycle, DNA Damage and Apoptosis Analysis

Cells were culture in 12 wells plate for 4 days. Apoptotic cells were detected using phycoerythrin-conjugated Annexin V (PE-annexin V, BD Pharmingen). For the cell cycle and DNA damage, we used the Apoptosis, DNA damage and cell proliferation kit (BD), following the manufacturer's protocol.

Primary Multiple Myeloma Cells

Bone marrow of patients presenting with previously untreated MM (N=5) at the university hospital of Montpellier was obtained after patients' written informed consent in accordance with the Declaration of Helsinki and agreement of the Montpellier University Hospital Centre for Biological Resources (DC-2008-417). Primary myeloma cells of patients were cultured with or without graded concentrations of selected inhibitors and MMC cytotoxicity evaluated using anti-CD138-Phycoerythrin monoclonal antibody and CD38-Allophycocyanin (Beckman-Coulter) as described (Moreaux et al., 2012).

Proteome ARRAY

Phospho kinases and apoptosis proteins were quantified using the dedicated proteome Profiler™ array (RD systems, Bio-techne) following the manufacturer instructions. 500 μg and 300 μg protein were used for the two arrays respectively.

Statistics and Combination Index.

Statistical comparisons were done with unpaired or paired Student's t-tests. The effect of drug combination was evaluated using the methods developed by Chou and Talalay (Chou and Talalay, 1984) by calculating the combination Index (CI), with CI<1, CI=1, and CI>1 respectively indicating synergism, additive effects, and antagonism. Here we used CI=0.90-1.10 to indicated additivity.

3—Results

Identification of 36 kinome related probe sets linked to prognosis in three independent multiple myeloma (MM) cohorts.

Considering the crucial role played by kinases in pathologies, including Multiple Myeloma (MM), the inventors first aimed to identify kinome related genes associated with prognosis in MM. A list of 661 Affymetrix probe sets (psets) extracted from literature, representing 661 genes part of the kinome, or kinome related in human (Sabatier et al., 2011) was thus tested, for their prognosis value in the Heidelberg-Montpellier cohort (Hose et al., 2011; Moreaux et al., 2012). Among the 661 psets, after multiple testing correction 104 demonstrated a significant prognosis value linked to their expression. In order to validate and narrow down to the most representative kinases in MM pathology the inventors further tested these 104 psets in two other independent cohorts, the UAMS-TT2 (Barlogie et al., 2006) and UAMS-TT3 (Nair et al., 2010) and a final list of 36psets with significant and identical prognostic value in the three cohorts was ultimately obtained (table 3).

TABLE 3

Table 1

| ID | Name | Prognostic |
|---|---|---|
| 214575_s_at | AZU1 | Good |
| 202284_s_at | CDKN1A | Good |
| 1007_s_at | DDR1 | Good |
| 205936_s_at | HK3 | Good |
| 204936_at | MAP4K2 | Good |
| 211913_s_at | MERTK | Good |
| 200707_at | PRKCSH | Good |
| 205486_at | TESK2 | Good |
| 208079_s_at | AURKA | Bad |
| 209642_at | BUB1 | Bad |
| 203755_at | BUB1B | Bad |

TABLE 3-continued

Table 1

| ID | Name | Prognostic |
|---|---|---|
| 204510_at | CDC7 | Bad |
| 204159 at | CDKN2C | Bad |
| 1555758_a_at | CDKN3 | Bad |
| 205394_at | CHEK1 | Bad |
| 201897_s_at | CKS1B | Bad |
| 204170_s_at | CKS2 | Bad |
| 204244_s_at | DBF4 | Bad |
| 221563_at | DUSP10 | Bad |
| 202934_at | HK2 | Bad |
| 222631_at | PI4K2B | Bad |
| 205698_s_at | MAP2K6 | Bad |
| 204825_at | MELK | Bad |
| 204641_at | NEK2 | Bad |
| 215025_at | NTRK3 | Bad |
| 1559052_s_at | PAK2 | Bad |
| 219148_at | PBK | Bad |
| 201037_at | PFKP | Bad |
| 204887_s_at | PLK4 | Bad |
| 1569323_at | PTPRG | Bad |
| 218209_s_at | RPRD1A | Bad |
| 202200_s_at | SRPK1 | Bad |
| 1558254_s_at | SRPK2 | Bad |
| 202786_at | STK39 | Bad |
| 1554408_a_at | TK1 | Bad |
| 204822_at | TTK | Bad |

On the 36 psets, 8 were associated with a good prognosis value (AZU1; CDKN1A; DDR1; HK3; MAP4K2; MERTK; PRKCSH; TESK2), while 28 kinases related genes demonstrated a bad prognosis value (AURKA; BUB1; BUB1B; CDC7; CDKN2C; CDKN3; CHEK1; CKS1B; CKS2; DBF4; DUSP10; HK2; P14K2B; MAP2K6; MELK; NEK2; NTRK3; PAK2; PBK; PFKP; PLK4; PTPRG; RPRD1A; SRPK1; SRPK2; STK39; TK1; TTK).

Analysis of their involvement in cellular physiology highlighted the cell cycle as the top KEGG pathway (Table 4), and string network of the 36psets showed highly interconnected proteins particularly for those with a role in cell cycle (FIG. 1)

TABLE 4

KEGGSPathways

| GO_id | Term | NumberOfGenes | p-value | p-value_fdr | p-value_bonferroni |
|---|---|---|---|---|---|
| 4110 | Cell cycle | 8 | 3.12E−11 | 8.96E−09 | 8.96E−09 |
| 52 | Glacatose metabolism | 3 | 1.97E−05 | 2.15E−03 | 5.64E−03 |
| 51 | Fructose and mannose metabolism | 3 | 2.40E−05 | 2.15E−03 | 6.88E−03 |
| 524 | Butirosin and neomycin biosynthesis | 2 | 3.00E−05 | 2.15E−03 | 8.61E−03 |
| 10 | Glycolysis/Gluoneogenesis | 3 | 1.60E−04 | 9.18E−03 | 4.59E−02 |
| 1200 | Carbon metabolism | 3 | 7.62E−04 | 3.05E−02 | 2.19E−01 |
| 4066 | HIF-1 signaling pathway | 3 | 7.84E−04 | 3.05E−02 | 2.25E−01 |
| 5166 | HTLV-1 infection | 4 | 9.43E−04 | 3.05E−02 | 2.71E−01 |
| 4010 | MAPKsignaling pathway | 4 | 9.57E−04 | 3.05E−02 | 2.75E−01 |

Figure 2:
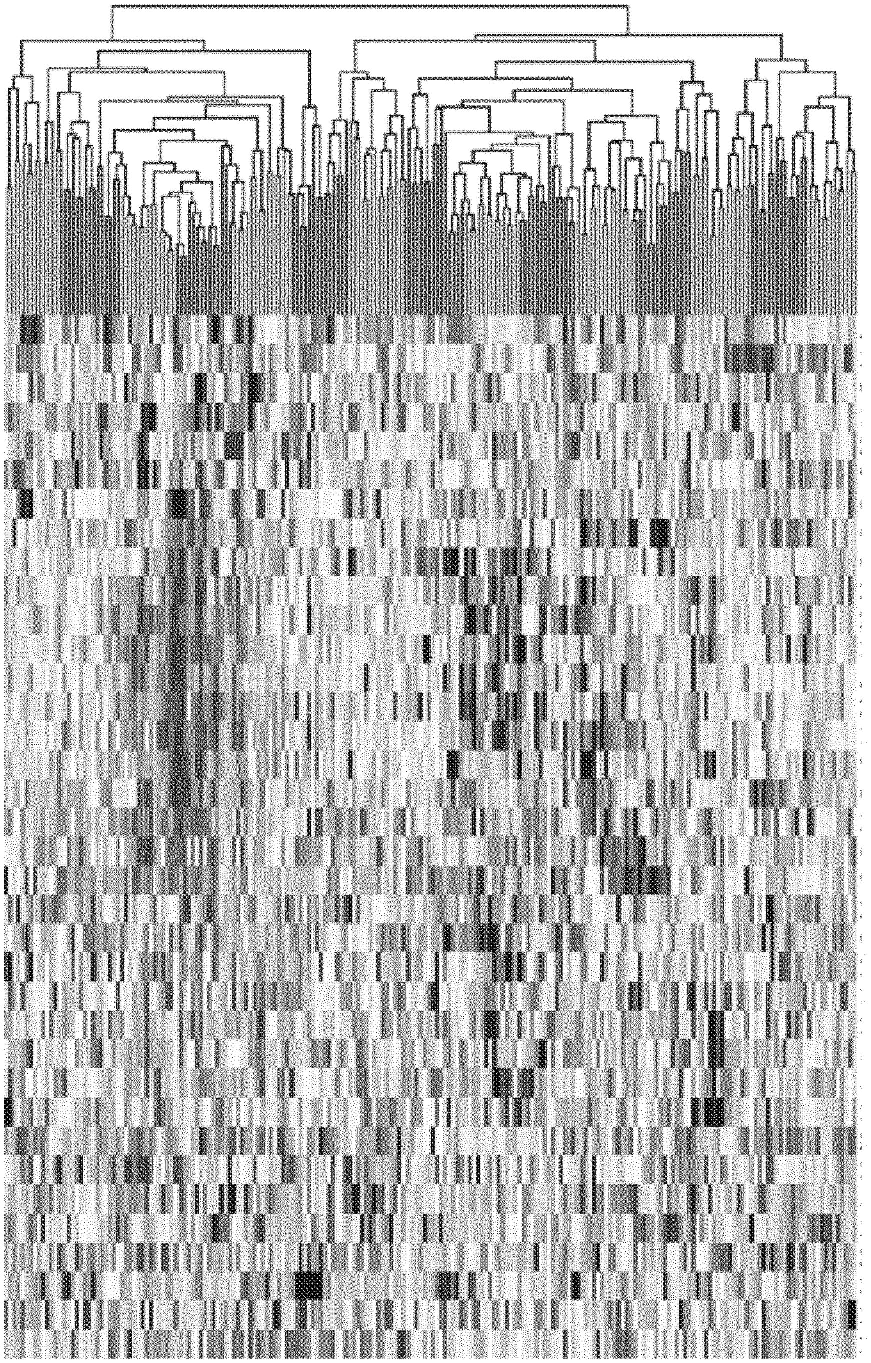
FIG. 2 represents a hierarchical clustering in HM cohort demonstrating an heterogeneous profile of expression for the 36 psets. Columns represent the patients of the cohort, and line represent each of the 36 genes.

The fact that the 36psets were selected according to their prognostic values and that they demonstrated high interconnection led us to expect a relative coherence of their expression among the patient of the HM cohort. The inventors were therefore surprised to observe a spread expression of the genes among the patients except for a cluster composed of 14 psets linked to mitosis (CDKN2C; CDC7; CDKN3; BUB1B; MELK; BUB1; AURKA; NEK2; PBK; TTK; CHEK1; PLK4; CKS1B and TK1) that exhibits a specific ON/OFF pattern of expression (FIG. 2).

Building a Kinome Index (KI) Predicting Outcome of MM Patients.

Figure 3:
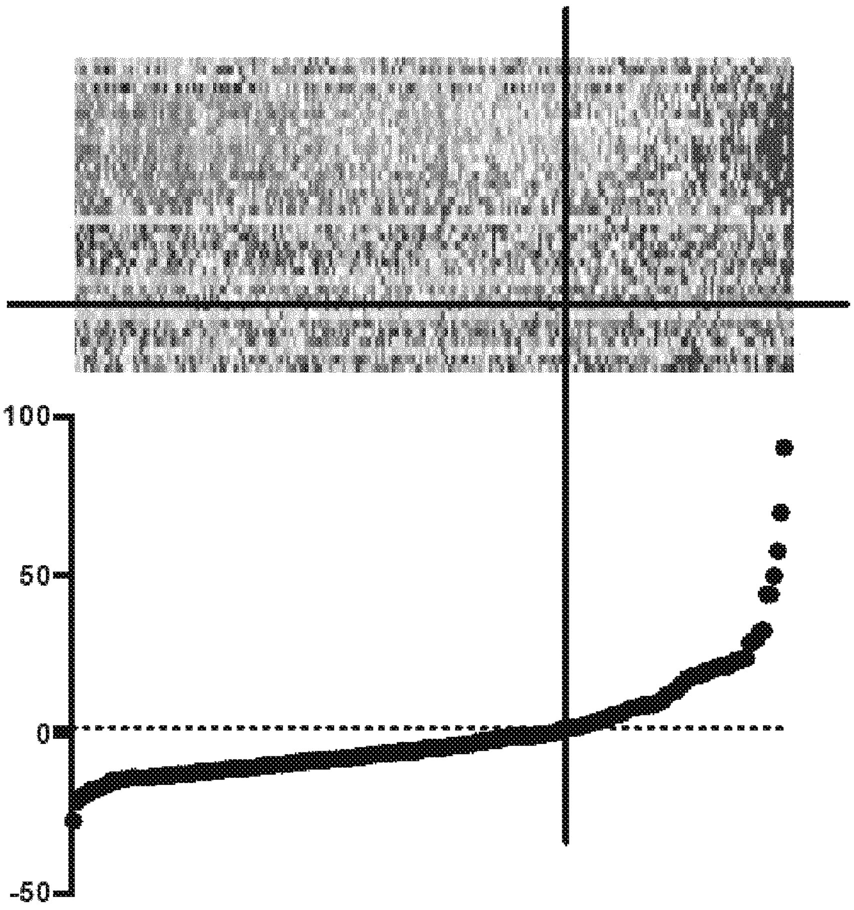
FIG. 3 is clustergram in the 206 HM cohort's patients of the 36 genes signal used to build the Kinome Index. Signals are displayed from low to high expression.
Figure 4:
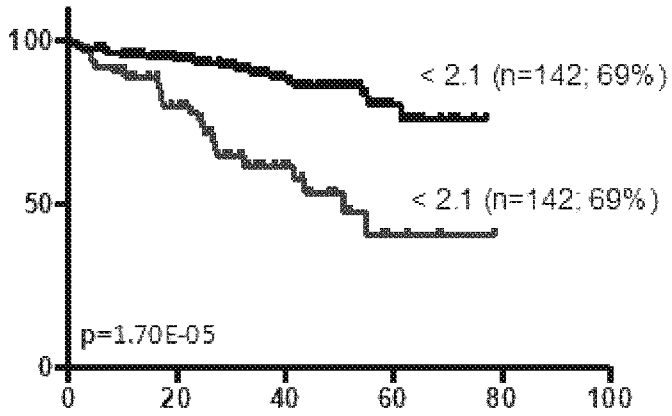
FIG. 4 is a Kaplan Meier curve showing the percentage of survival vs time (days) illustrating that KI is linked to OS in the HM cohort
Figure 5:
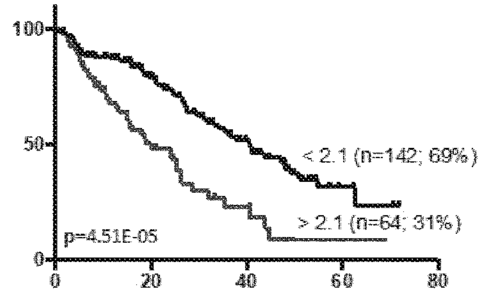
FIG. 5 is a Kaplan Meier curve showing the percentage of survival vs time (days) illustrating that KI is linked to EFS in the HM cohort.
Figure 6:
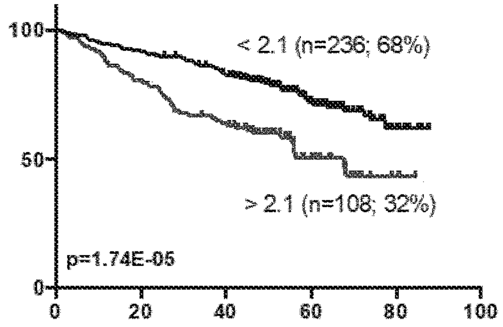
FIG. 6 is a Kaplan Meier curve showing the percentage of survival vs time (days) illustrating that KI is linked to OS in the TT2 cohort.
Figure 7:
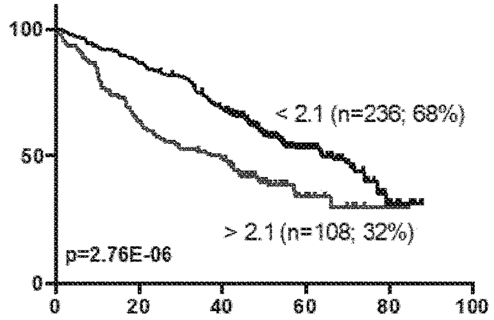
FIG. 7 is a Kaplan Meier curve showing the percentage of survival vs time (days) illustrating that KI is linked to EFS in the TT2 cohort.
Figure 8:
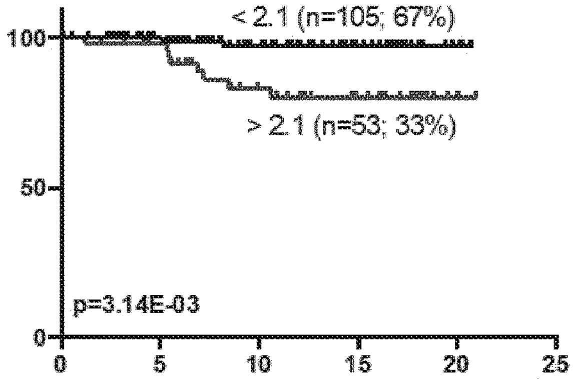
FIG. 8 is a Kaplan Meier curve showing the percentage of survival vs time (days) illustrating that KI is linked to OS in the TT3 cohort.

As the 36 psets are independently highly connected to prognostic value of patients in HM cohort, it is then relatively heavy to analyze each selected kinase behavior independently in MM physiopathology. To bypass this difficulty the inventors created a Kinome Index (KI) using the expression data of the 36 psets, as described in the material and methods section. Maxstat statistic segregates HM cohort into two groups with 31% of the patients with a KI>2.1 and 69% of the patients with a KI≤2.1 (FIG. 3). As expected from the psets selection method, the inventors observed that the KI was significantly linked to OS (50.6 months vs not reached (p=1,70798E−05)) and the EFS (20.1 months vs 40.6 months (p=1.7E−05)) in the HM cohort respectively for the High KI group vs the Low KI group (FIGS. 4 and 5). Likewise, the KI segregated the UAMS-TT2 and TT3 cohorts in two different prognosis groups for the OS or the EFS (FIGS. 6 to 8). Therefore KI seems to be a valuable tool to investigate the 36psets together in various MM models.

Figure 9:
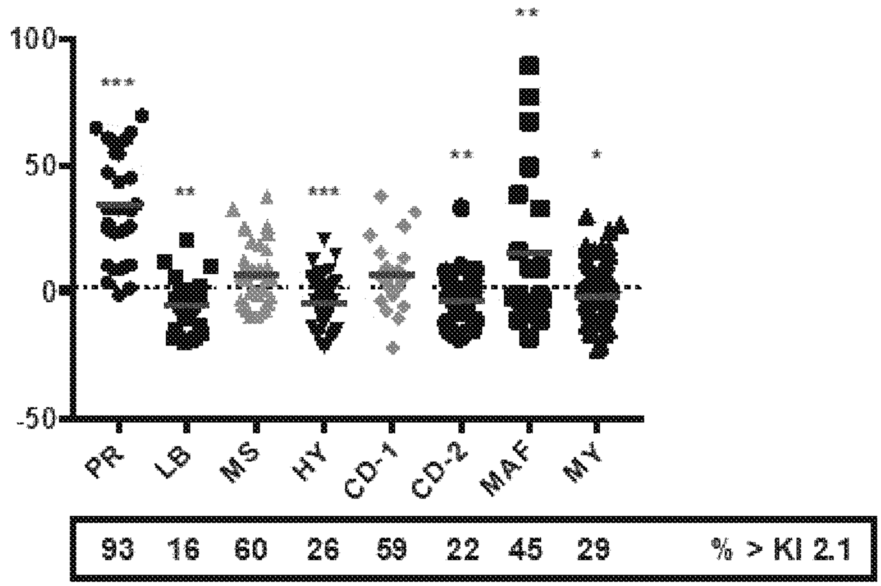
FIG. 9 is a graph showing the KI data normalized to HM normalization and identifying that KI is linked to bad prognosis subgroups in MM. p-value: *<0.05; <0.01; *<0.001. PR: proliferation, LB: low bone disease, MS: MMSET, HY: hyperdiploid, CD1: cyclin D1-cyclin D3, CD2: cyclin D1-cyclin D3, MF: MAF.

Then the inventors first tested the KI in the different Multiple Myeloma molecular subgroups as defined by UAMS (Zhan et al., 2006). The inventors observed a particularly strong association between the KI and the proliferation subgroup (PR) since 93% of the PR subgroups has a KI>2.1 (p<8E−18). In addition, MMSET, CD-1 and MAF were also related to a high KI, although both their KI and the % of patient within the subgroup with a KI>2.1 was considerably lower than for the PR group (with respectively 60% 59% and 45% in the three subgroups) (FIG. 9). However, that last observation is of particular interest since these three subgroups are as well associated with poor prognosis. The inventors therefore can speculate that they could be treated with a therapy targeting identified kinases.

Figure 10:
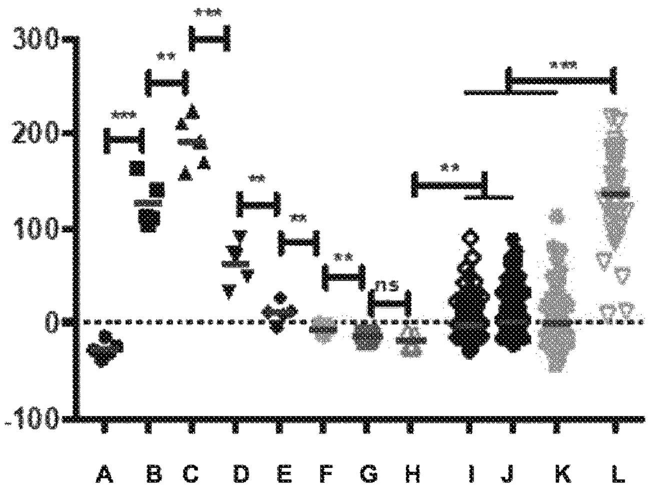
FIG. 10 is a graph showing the KI data normalized to HM normalization and identifying that KI is associated with high proliferation in an in vitro model of normal plasma cell differentiation. A: Memory B Cells, B: B activated, C; preplasmablasts, D: Plasmablasts, E: long-lived plasma cells, F: Normal bone marrow plasma cells, G: MGUS, H: HM, I: TT2, K: TT3 and L: HMCLs. p-value: *<0.05; <0.01; *<0.001.
Figure 11:
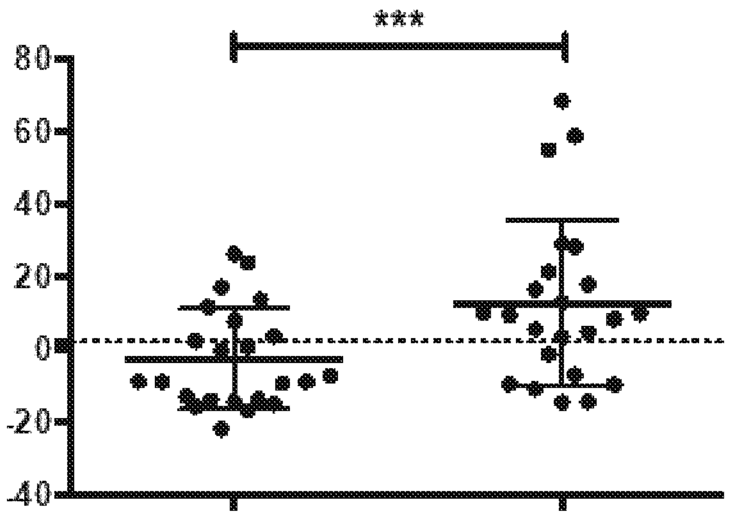
FIG. 11 is a graph showing the KI data normalized to HM normalization and identifying that KI increase after relapse in a cohort of 23 patients. p-value: *<0.05; <0.01; *<0.001.

The origin of tumoral plasma cells is still a highly discussed subject. The inventors developed a differentiation model that recapitulates the different differentiation steps from Naïve B cells to plasma cells (Jourdan et al., 2009, 2014). Then the inventors analyzed the KI in this model in order to picture the influence of these kinases along differentiation and tumorogenesis. Interestingly, higher KI was associated with proliferating cells as the B activated, the prePlasmablasts and the plasmablasts, while lower KI (<2.1) was associated with all the other cells subtypes, known to do not have, or to have reduced, cell cycle activity (FIG. 10). This observation corroborates the association of the 36 kinases to cell cycle (Table 3) and the PR subgroup (FIG. 9), as well as the well-known association of kinases activation with proliferation. In addition, the KI slowly increases with disease progression from Bone Marrow Plasma Cells (BMPC) to malignant plasma cells (Multiple Myeloma MM cells). Moreover, in addition to the fact that the KI demonstrated a homogeneous index between the different cohorts tested (HM TT2 and TT3) (FIG. 10) the inventors tested the KI in a cohort of patients at diagnosis and at relapse and observed a significant increase of the KI at relapse (FIG. 11). Altogether these observations further highlight that the selected kinases could represent new potential therapeutic targets in MM.

Selected Kinases Inhibition Lead to MM Cell Death In Vitro.

Figure 12:
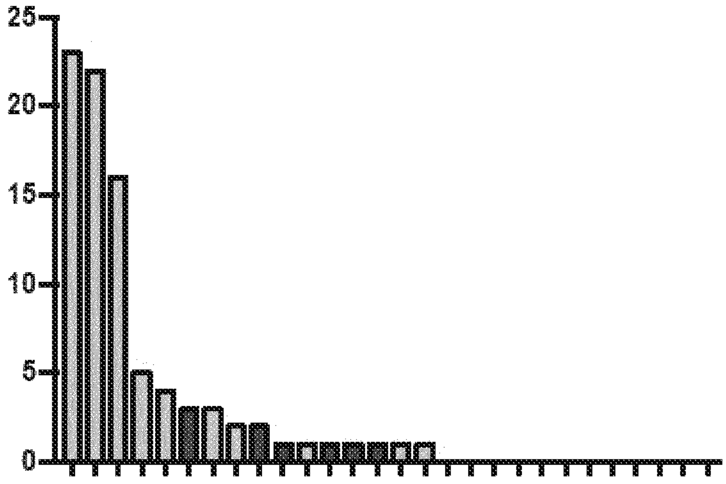
FIG. 12 is a graph representing a selection of 7 probesets (dark grey) for further investigations, based on citation report in pubmed and available inhibitors.
Figure 13:
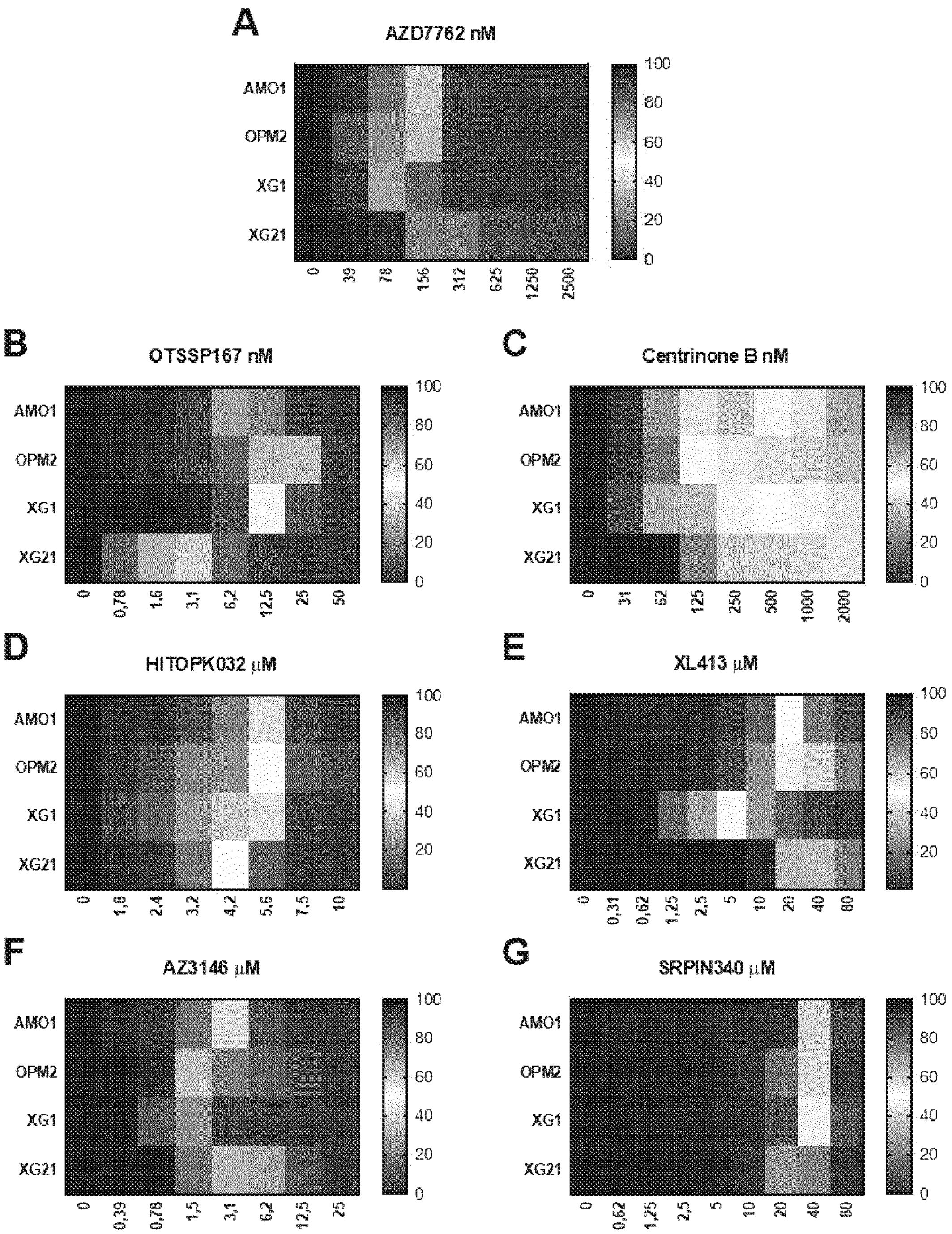
FIG. 13 from A-G represent HMCLs viability measured by CTG assay after treatments with all inhibitors in 4 HMCLs (AMO1, OPM2, XG1, XG21). Cell viability is expressed in % of untreated condition.

According to the inventors in silico analysis, the 36 psets demonstrated outstanding connection with MM physiopathology and prognosis. Thus, the inventors next decided to test some of the kinases for their individual potential on MM models using specific inhibitors, and the inventors hence selected kinases of interest. In that purpose the inventors first excluded the 8 psets associated with good prognosis, and tested the 28 remaining psets for their link with MM in literature. Three psets (CKS1B; AURKA; CDKN2C) whose connections were already widely studied (CKS1B (Shaughnessy, 2005; Shi et al., 2010) AURKA (Evans et al., 2008) CDKN2C) were then also excluded. The inventors finally selected the only 7 psets (PBK; CHK1; MPS1/TTK; DBF4; MELK; PLK4; SRPK1) that had commercially available specific inhibitors at the time of the study (FIG. 12). To note, all except SRPK1 are involved in the mitotic cell cycle processes.

In the following experiment the inventors challenged the kinase inhibitors for their potential anti-myeloma effect on four human myeloma cell lines representing two commercials (AMO-1; OPM2) and two IL-6 dependent cell lines developed in the inventors' laboratory (XG-1; XG-21). Remarkably all tested drugs led to a significant decrease in HMCLs viability, with an 1050 that could be determined in all the cases (Table 5, FIGS. 13A to 13G).

TABLE 5

| | | | AMO1 | OPM2 | XG)1 | XG)21 |
|---|---|---|---|---|---|---|
| CHEK1 | AZD7762 | IC50 nM | 136 | 116 | 95 | 210 |
| | | IC20 nM | 82 | | | |
| MELK | OTSSP167 | IC50 nM | 8.2 | 16 | 12 | 2 |
| | | IC20 nM | 5.4 | | | |
| PLK4 | Centrinone-B | IC50 nM | 421 | 440 | 226 | 1392 |
| | | IC20 nM | 24 | | | |
| SRPK1 | SRPIN340 | IC50 μM | 43.3 | 33.2 | 30.1 | 25.8 |
| | | IC20 μM | 30.0 | | | |
| DBF4 | XL413 | IC50 μM | 19.9 | 24.5 | 4.2 | 30.3 |
| | | IC20 μM | 9.4 | | | |
| MPS1/TTK | AZ3146 | IC50 μM | 2.6 | 1.9 | 1.2 | 3.0 |
| | | IC20 μM | 1.4 | | | |
| PBK | HI)TOPK | IC50 μM | 5.1 | 5.0 | 4.4 | 4.1 |
| | | IC20 μM | 3.9 | | | |

Figure 14:
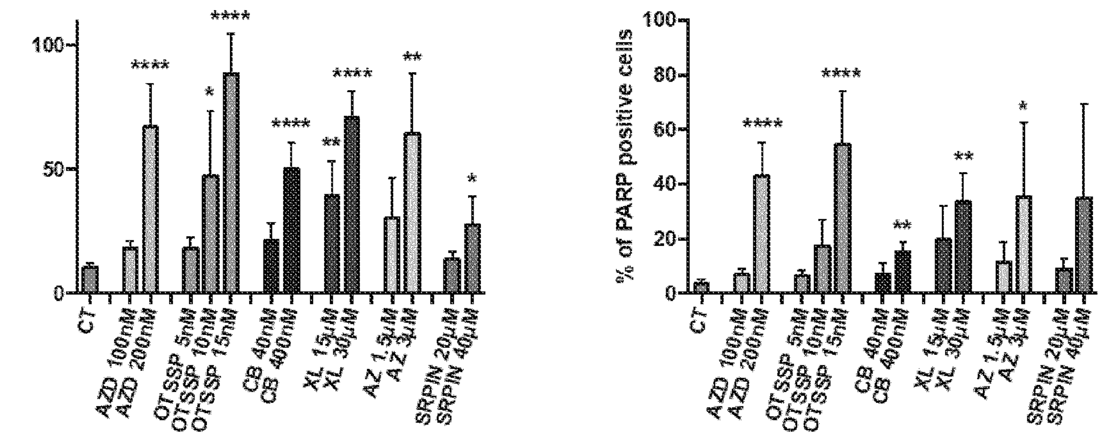
FIG. 14 represents graphs showing that inhibitors increase apoptosis (annexin and PARP) in AMO1 cell line; Annexin and PARP were monitored by flow cytometry after 4 days treatments. p-value: *<0.05; <0.01; *<0.001.
Figure 15:
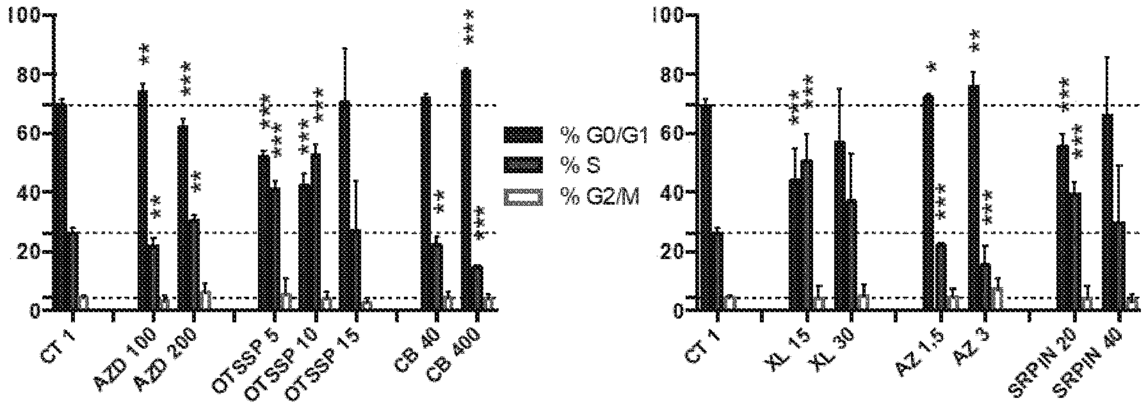
FIG. 15 represents graphs showing the effects of the treatments with inhibitors on cell cycle in AMO1 cells. p-value: *<0.05; <0.01; *<0.001.
Figure 16:
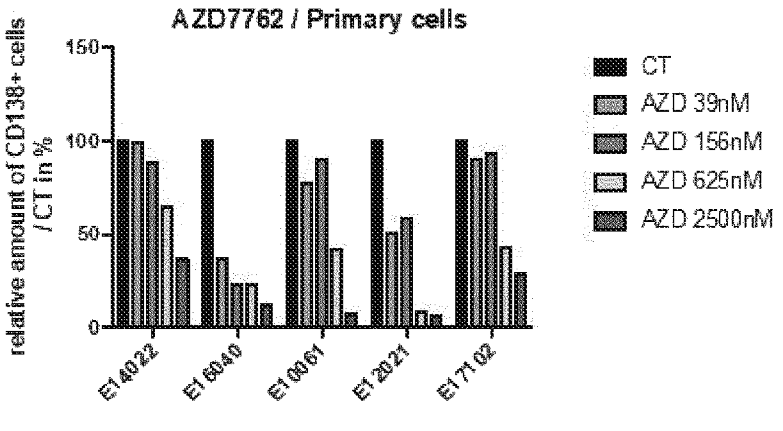
FIG. 16 represents graphs showing the % of CD138+ cells after treatment by AZD7762, OTSSP167 and Centrinone B in 5 different primary MM cells.
Figure 16:
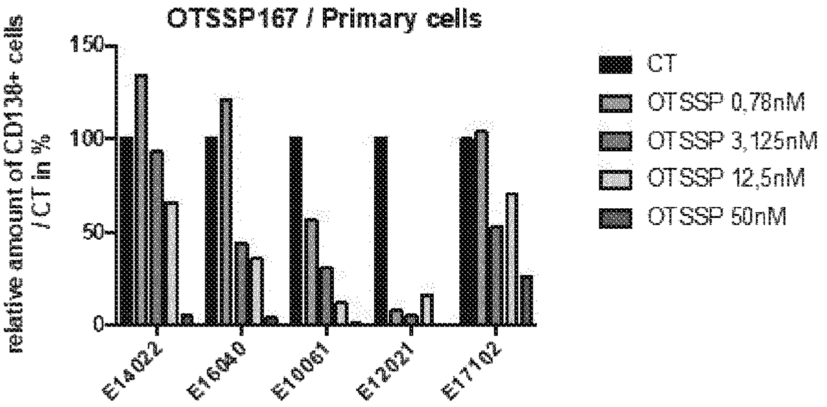
Figure 16:
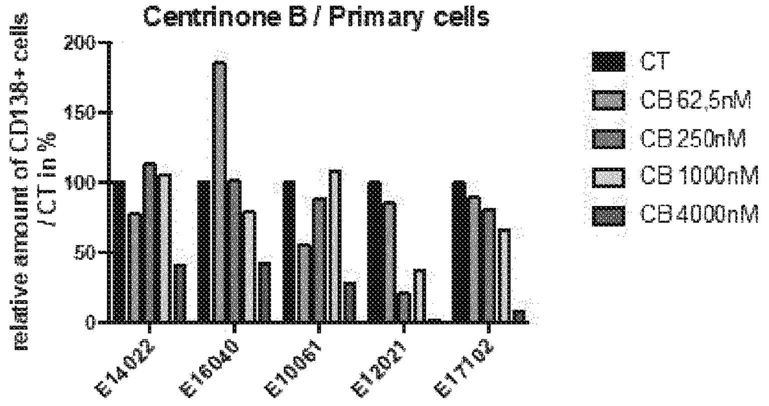
Figure 17:
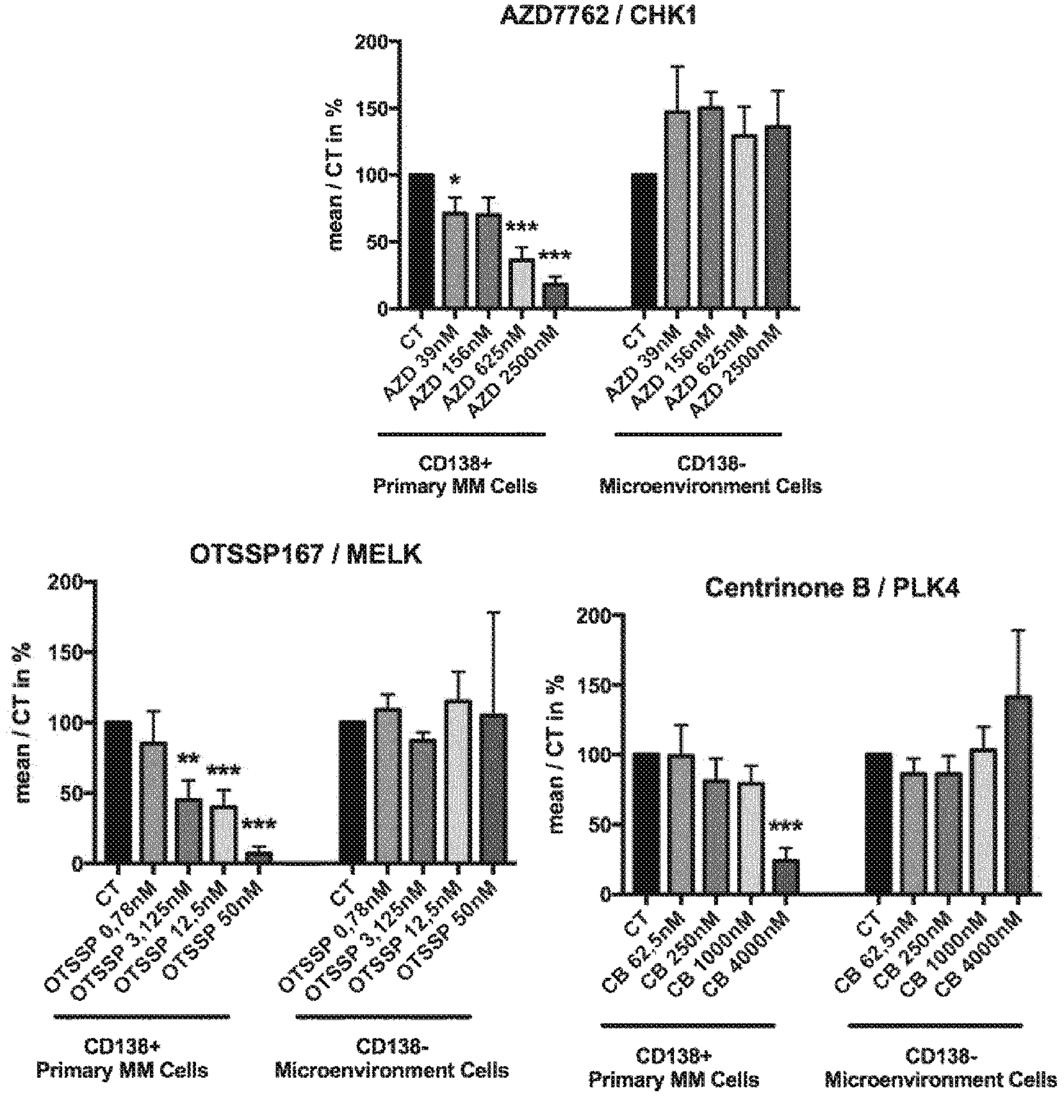
FIG. 17 represents graphs showing that the three tested inhibitors reduce % of tumor MM cells without toxicity on normal BM microenvironment cells from patients (N=5). CD138 amount was monitored by flow cytometry after 4 days of treatment.

The inventors next investigated how the tested drugs impacted cell death in the AMO1 HMCL. In that set of experiment 2 concentrations of drugs surrounding the calculated IC50s were used. As shown on FIG. 14, all drugs but SRPIN340/SRPK1 induced apoptosis as measured by annexin V staining and PARP clivage analyses. Interestingly that effect was not observed at the lower concentration used, thus confirming the inventors' previous observation of a dose dependence efficacy of the drugs. It is known that cell death is often supported by cell cycle deregulation. The inventors then tested the ability of the kinase inhibitors to perturb cell cycle. The inventors' results showed that the inhibitors are able to perturb cell cycle since AZD7762/CHK1; OTSSP167/MELK and XL413/DBF4 arrested the cells in S phase, while Centrinone B/PLK4 and AZ3146/MPS1 arrested the cell cycle in G0/G1 in AMO1 HMCL (FIG. 15). Thus, the different inhibitors tested act both by killing MM cells and inhibiting their proliferation. In addition, the inventors tested the three inhibitors that reduce cells viability at nanomolar concentration (AZD7762; OTSSP167; Centrinone B) on primary MM cells from patients. Remarkably, all three tested drugs reduced the number of tumoral cells while non-tumoral cells were barely affected by the treatment (FIG. 17). Although inter-individual variability of the patients tested led to an heterogeneous response to treatments (FIG. 16). Moreover no correlation between the expression of the inhibitor target gene and the calculated 1050 could be observed (not shown).

Figure 18:
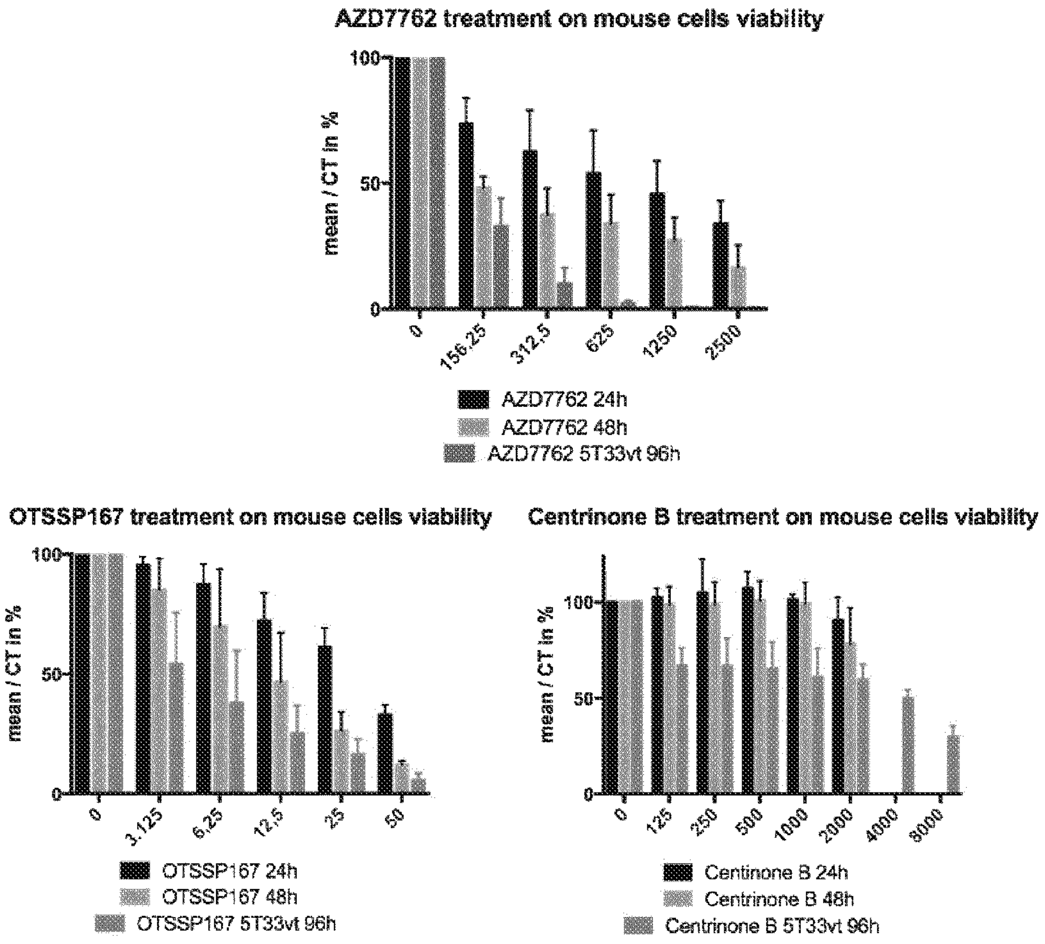
FIG. 18 represents graphs cell viability of primary Mouse myeloma (5T33vv) and mouse myeloma cell line (5T33vt), monitored by CTG after 24, 48 or 96 hours treatment with indicated inhibitors.

In addition, in order to demonstrate the capability of preclinical studies for the 3 selected inhibitors, the inventors tested them in a mouse cellular model of multiple myeloma. As shown in FIG. 18, AZD7762 and OTSSP167 demonstrated similar efficiency while Centrinone B was less effective on cell viability in this model.

Figure 19:
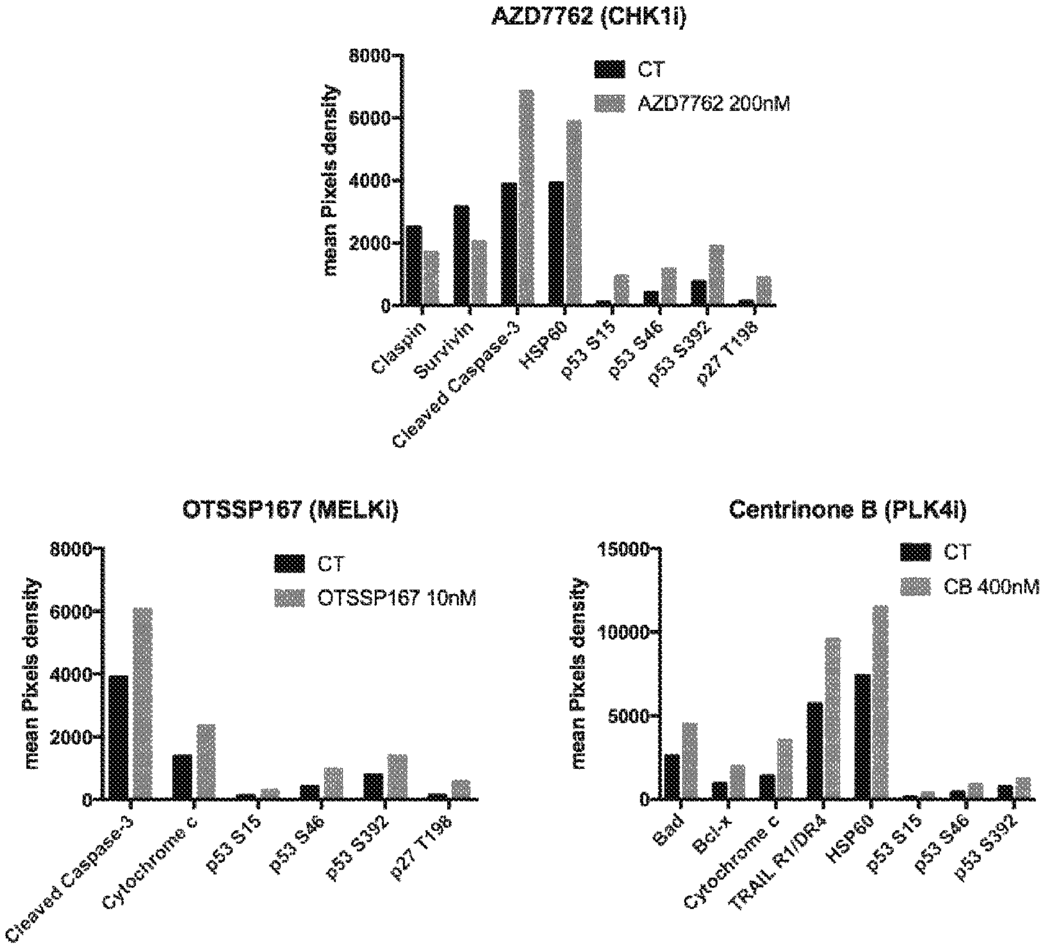
FIG. 19 represents graphs illustration the effects of the inhibitors on apoptosis and signaling pathways. Proteins accumulations were monitored after 48 h treatment on AMO1 HMCL using proteome profiler array. Relative amount was calculated as the mean of pixel density.

Finally, the inventors examined the pathways involved in apoptosis and cell cycle following treatments in AMO1 cells using proteome array. For all three tested drugs, the inventors observed an increase in p53 phosphorylations (S15; S46; S392) where S15 is linked to DNA damages, S46 modulates the apoptosis and S392 the growth suppression capacities of p53 (FIG. 19). Similarly, the inventors could observe increase in other proteins involved in apoptosis processes, as cleaved caspase 3, p27, cytochrome C, HSP60 or TRAIL, Bad and Bcl-x. In addition, the inventors also observed in the case of AZD7762 treatment a decrease in claspin and survivin, two proteins involved in cell cycle and proliferation. Altogether the inventors thus demonstrate the pro-apoptotic effect of these three molecules on AMO1 MM cells and the inventors' results highlight the potential of these kinases as new therapeutic targets in MM, and therefore validate the general strategy used here to discover potential new MM treatments.

Conventional MM Therapies are Potentialized by Selected Kinase Inhibitors.

Figure 20:
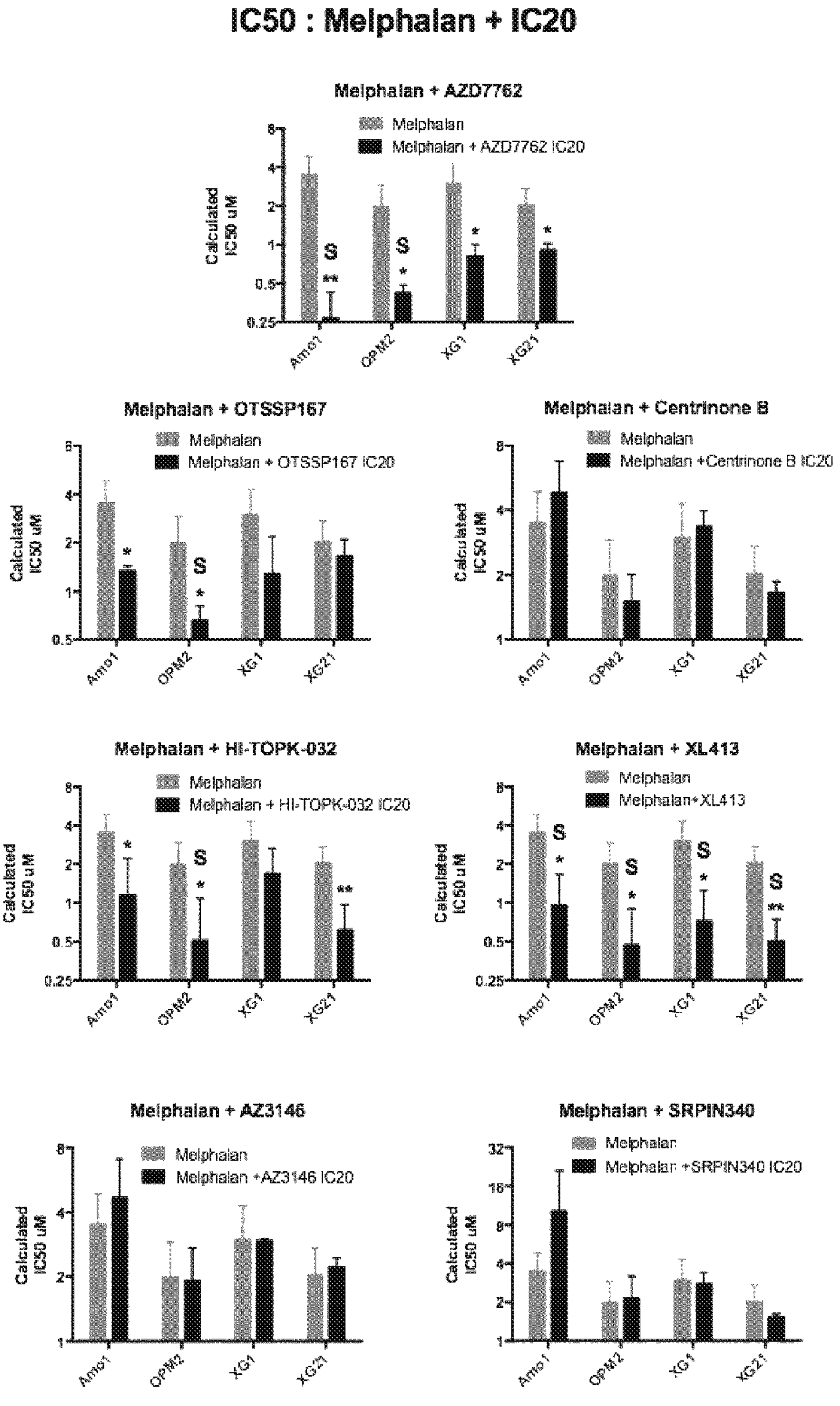
FIG. 20 represents graphs illustrating the effects of kinases inhibitors in order to potentiate conventional MM drugs activity in HMCLs. Calculated IC50 after co-treatment with selected kinase inhibitors at IC20 and Melphalan for four HMCLs. p-value: *<0.05; <0.01; *<0.001. S=Significant synergy calculated by the method of Chou and Talalay.
Figure 21:
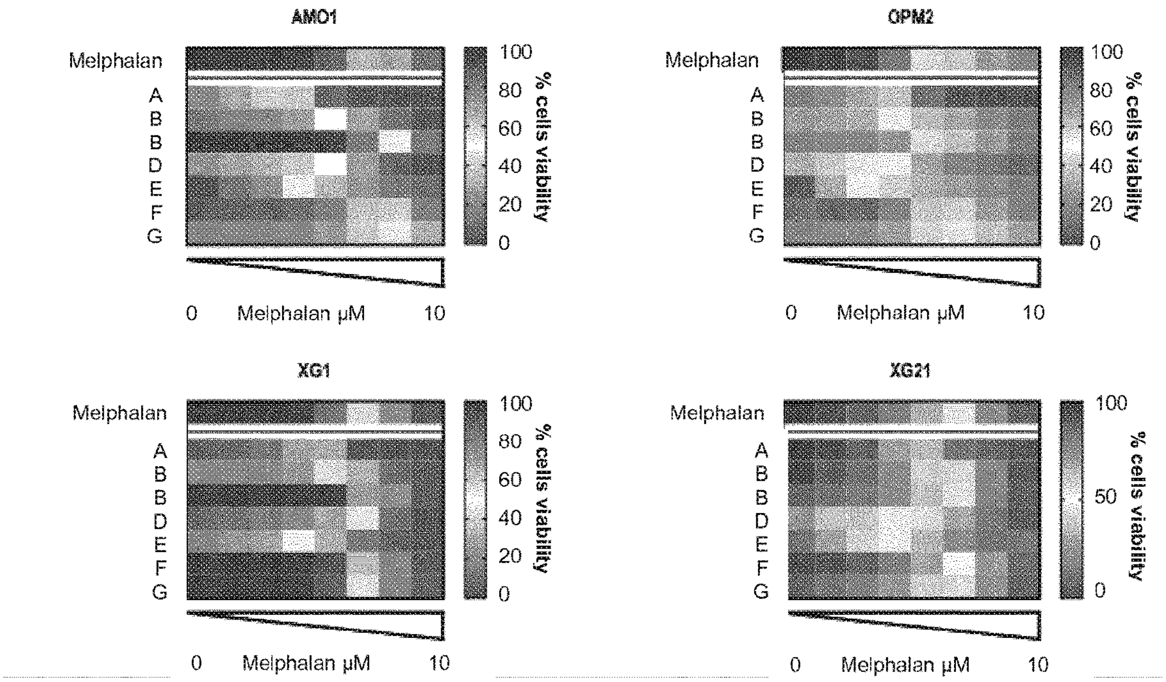
FIG. 21 represents HMCLs viability measured by CTG assay in 4 HMCLs after co-treatment with selected kinase inhibitors at IC20 and Melphalan. Cell viability is expressed in % of untreated condition.
Figure 22:
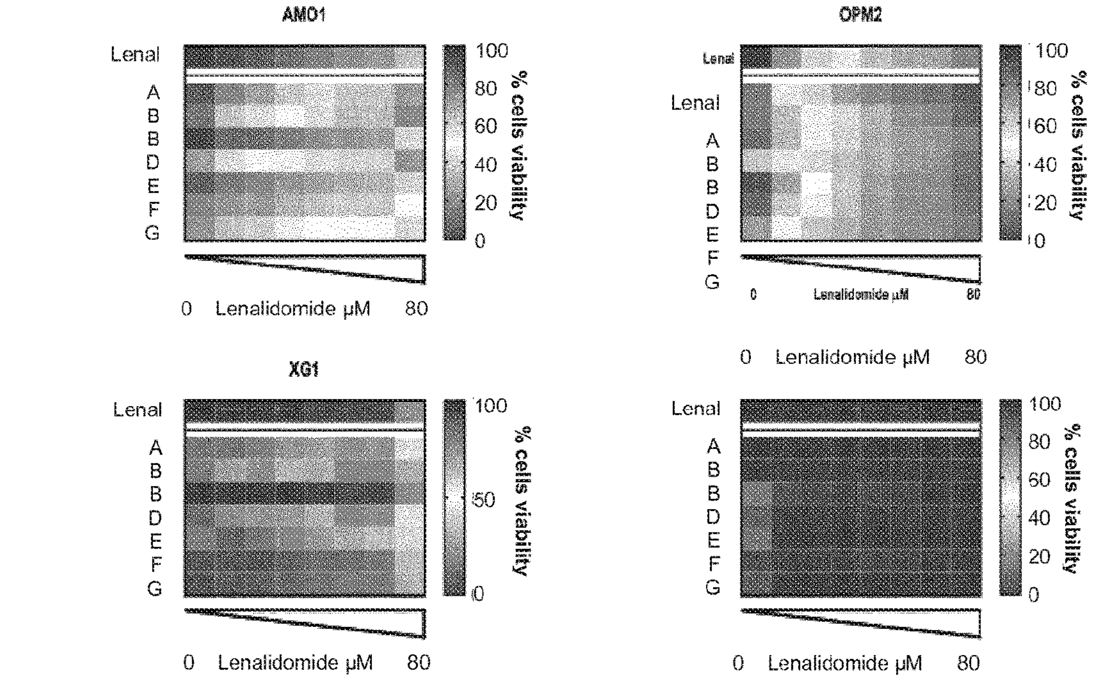
FIG. 22 represents HMCLs viability measured by CTG assay in 4 HMCLs after co-treatment with selected kinase inhibitors at IC20 and Lenalidomide. Cell viability is expressed in % of untreated condition.
Figure 23:
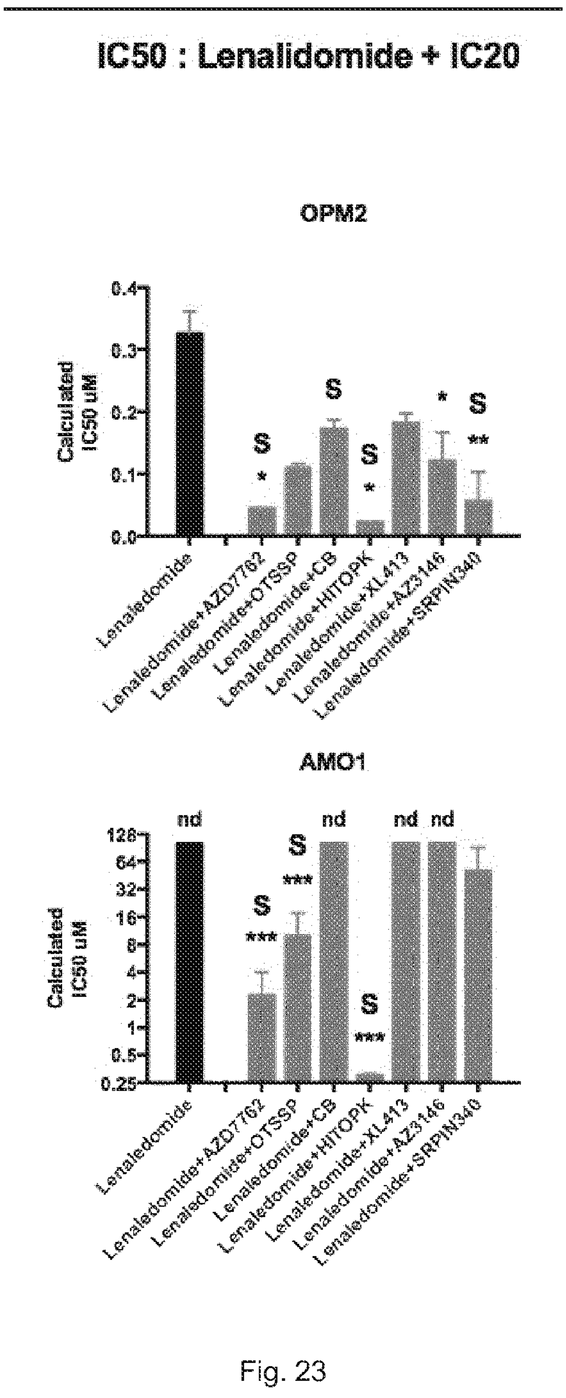
FIG. 23 represents graphs illustrating the effects of kinases inhibitors in order to potentiate conventional MM drugs activity in HMCLs. Calculated IC50 after co-treatment with selected kinase inhibitors at IC20 and Lenalidomide for 2 HMCLs. p-value: *<0.05; <0.01; *<0.001. S=Significant synergy calculated by the method of Chou and Talalay.
Figure 24:
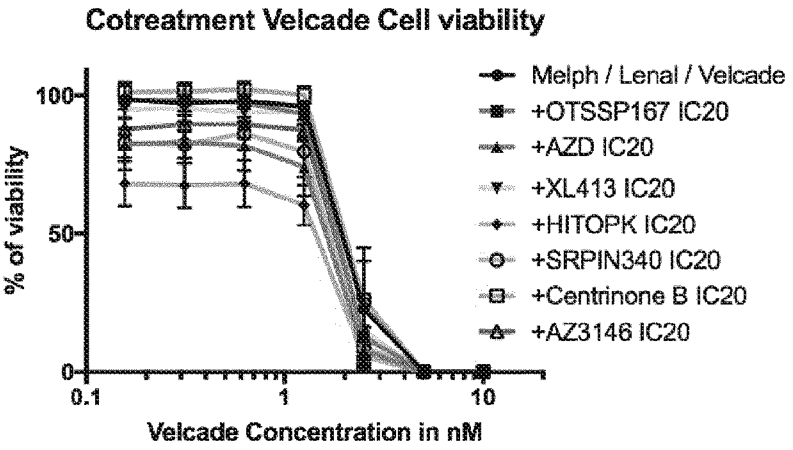
FIG. 24 represents a graph illustrating the effect on cell viability of co-treatment with selected kinase inhibitors at IC20 and Velcade (CTG assay).

Keeping in mind the main objective of identifying alternative and efficient complementary treatment for MM patients, the inventors next performed co-treatment on HMCLs with commonly used therapeutic drugs in MM (e.g. Melphalan, Lenalidomide, Velcade) and the different kinases inhibitors. In order to fit to the goal of a combination treatment the inventors used an arbitrary 1020 for all the kinases inhibitors, which the inventors associated with various concentration of the standard therapeutic. Thus, Melphalan (alkilating agent) treatment was potentialized by CHK1, MELK, PBK and DBF4 inhibitors in at least three on the four tested HMCLs, with an observed significant decrease in the 1050, while no effect on the calculated 1050 was noticed for the co-treatment of melphalan with PLK4, MPS1 and SRPK1 inhibitors at their 1020 (FIG. 20 and FIG. 21). When the inventors tested the combination of the immunomodulatory agent lenalidomide with the kinases inhibitors, the inventors observed no effect of the treatment alone or in combination in two lenalidomide resistant HMCLs (XG1 and XG21) while similar treatments were potentialized in two other HMCLs (AMO1 and OPM2) with the CHK1, MELK and PBK inhibitors. Remarkably, the inventors even could observe a reversion of lenalidomide resistance for the AMO1 cell line with the combination treatments. While 1050 for the treatment alone was undetermined, co-treatment with the kinase inhibitor at its 1020 led to a new IC50<1 uM (FIG. 23 and FIG. 22). Conversely the inventors couldn't observe any synergy or even additivity for the co-treatment with Velcade, whatever the cell line tested or the kinase's inhibitor used (FIG. 24). Altogether these results demonstrate a capability of approximately half of the selected kinase's inhibitor to potentialize or even synergize with conventional treatment to reduce HMCL viability (Table 6).

TABLE 6

| Ci Total | M + AZD | M + OT | M + C/B | M + SRP | M + XL | M + ZD | M + HIT |
|---|---|---|---|---|---|---|---|
| Amo1 | 0.7 | 1.1 | 1.5 | 2.5 | 0.7 | 1.9 | 1.0 |
| OPM2 | 0.8 | 0.8 | 0.8 | 1.6 | 0.5 | 1.6 | 0.8 |
| XG1 | 1.0 | 1.1 | 1.2 | 1.6 | 0.5 | 1.8 | 1.2 |
| XG21 | 1.1 | 1.3 | 0.9 | 1.4 | 0.7 | 1.6 | 1.1 |
| Ci Total | M + AZD | M + OT | M + C/B | M + SRP | M + XL | M + ZD | M + HIT |
| Amo1 | 0.6 | 0.7 | 1.1 | 0.9 | 1.5 | 1.6 | 0.8 |
| OPM2 | 0.8 | 0.9 | 0.6 | 0.7 | 0.9 | 1.0 | 0.7 |
| XG1 | 1.7 | 1.6 | 1.0 | 1.6 | 0.5 | 1.7 | 1.6 |
| XG21 | 1.7 | 1.4 | 1.1 | 1.6 | 1.5 | 1.5 | 1.8 |

M = Melphalan, L = Lenalidomide OT = OTSSP167, HIT = HITOPK032, AZD = AZD7762, SR = SRPIN340, XL = XL413 and C/B = Centrinone B/LCR 323, AZ = AZ3146.

Figure 25:
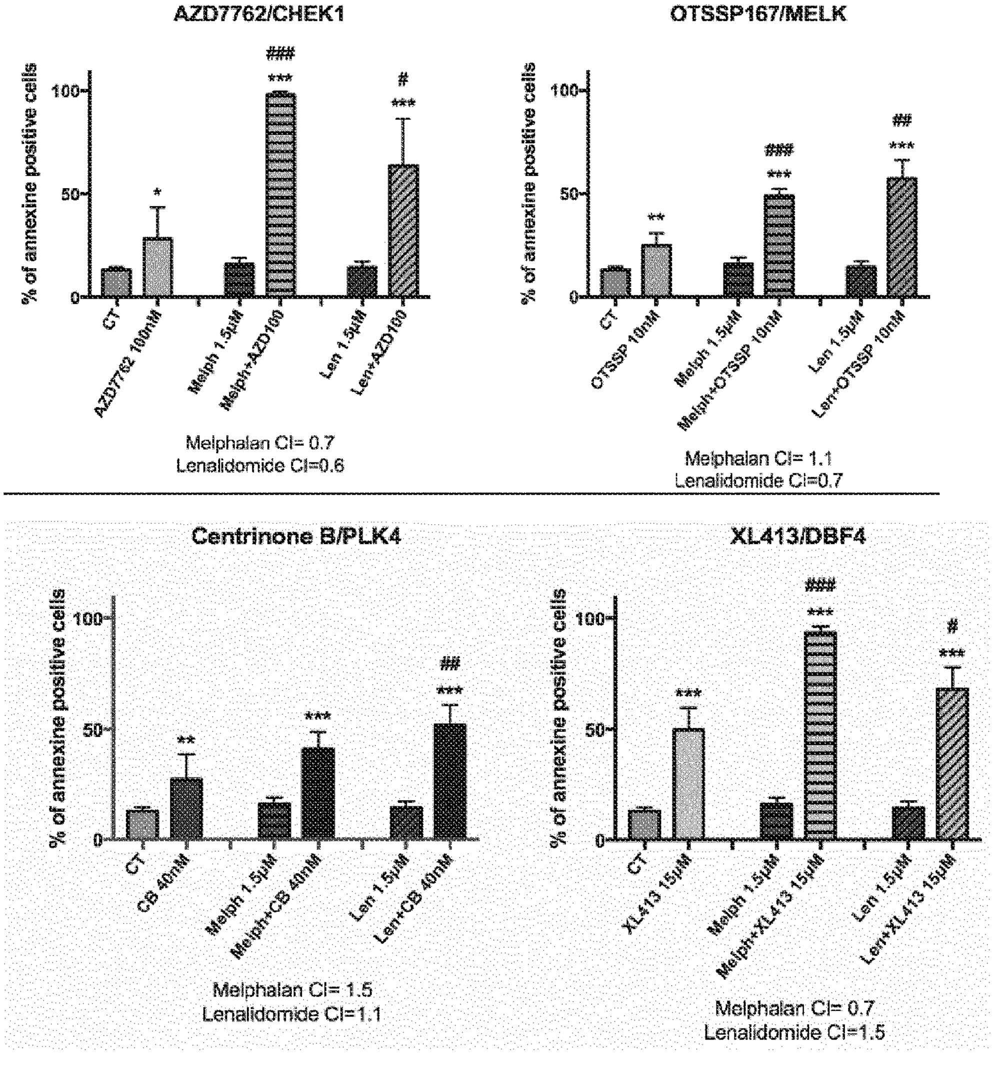
FIG. 25 represents graphs illustrating that the co-treatments induce cell death and differentially affect DNA damages in AMO1 HMCL. Co-treatment with selected kinase inhibitors at IC20 and Melphalan or Lenalidomide. Annexin was monitored by flow cytometry after 4 days treatments. p-value: *<0.05; <0.01; *<0.001. #=significantly different of each individual treatment.
Figure 26:
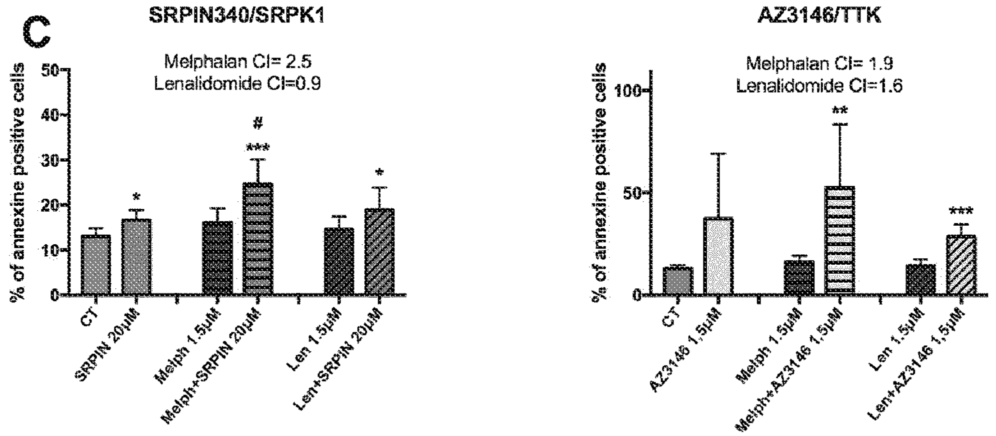
FIG. 26 represents graphs illustrating Annexin positivity following SRPIN340 and AZ3146 co-treatment in AMO1 cell line. Annexin was monitored by flow cytometry after 4 days of treatment. p-value: *<0.05; <0.01; *<0.001.
Figure 27:
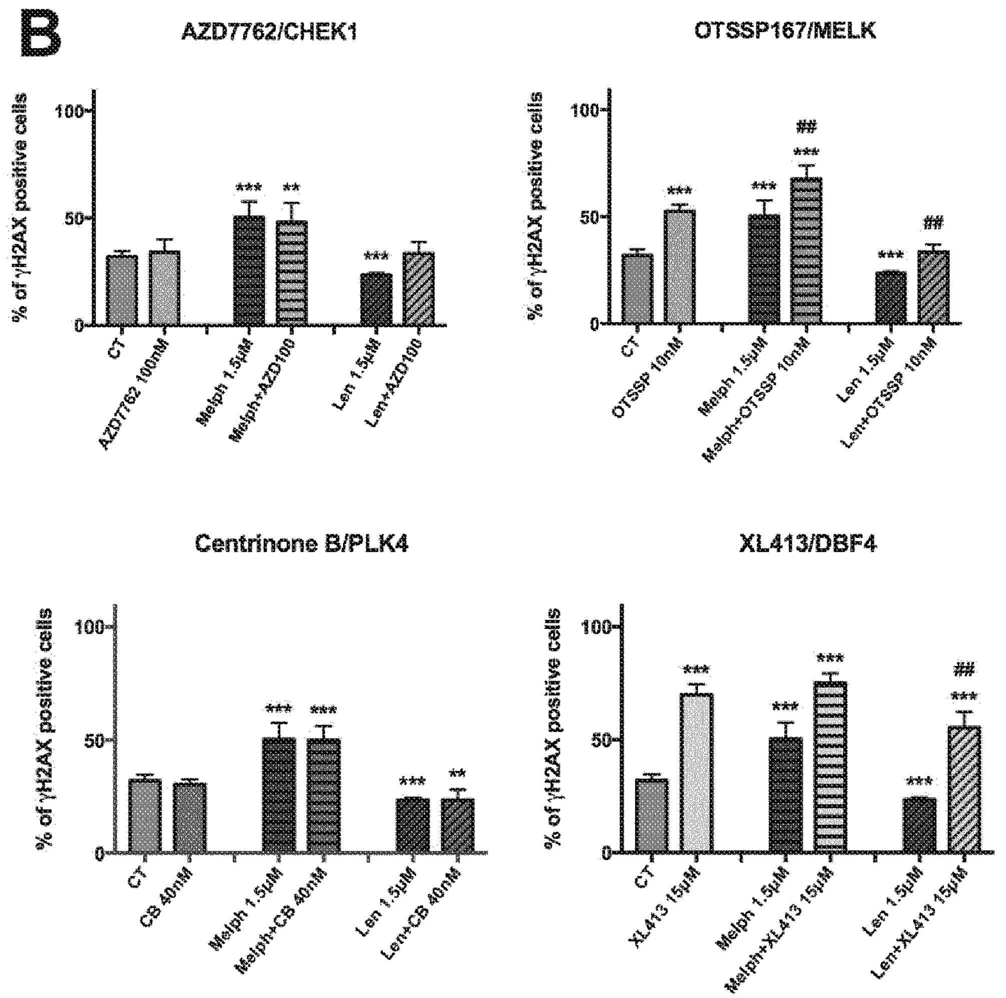
FIG. 27 represents graphs illustrating that the co-treatments induce cell death and differentially affect DNA damages in AMO1 HMCL. Co-treatment with selected kinase inhibitors at IC20 and Melphalan or Lenalidomide. γH2AX is evaluated. γH2AX was monitored by flow cytometry after 4 days treatments. p-value: *<0.05; <0.01; *<0.001. #=significantly different of each individual treatment.
Figure 28:
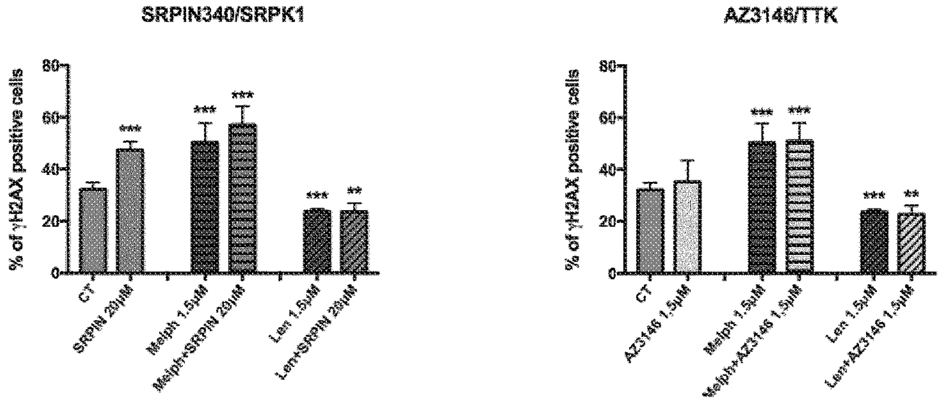
FIG. 28 represents graphs representing DNA damages following SRPIN340 and AZ3146 co-treatment in AMO1 cell line. γH2AX were monitored by flow cytometry after 4 days treatments. p-value: *<0.05; <0.01; *<0.001.
Figure 29:
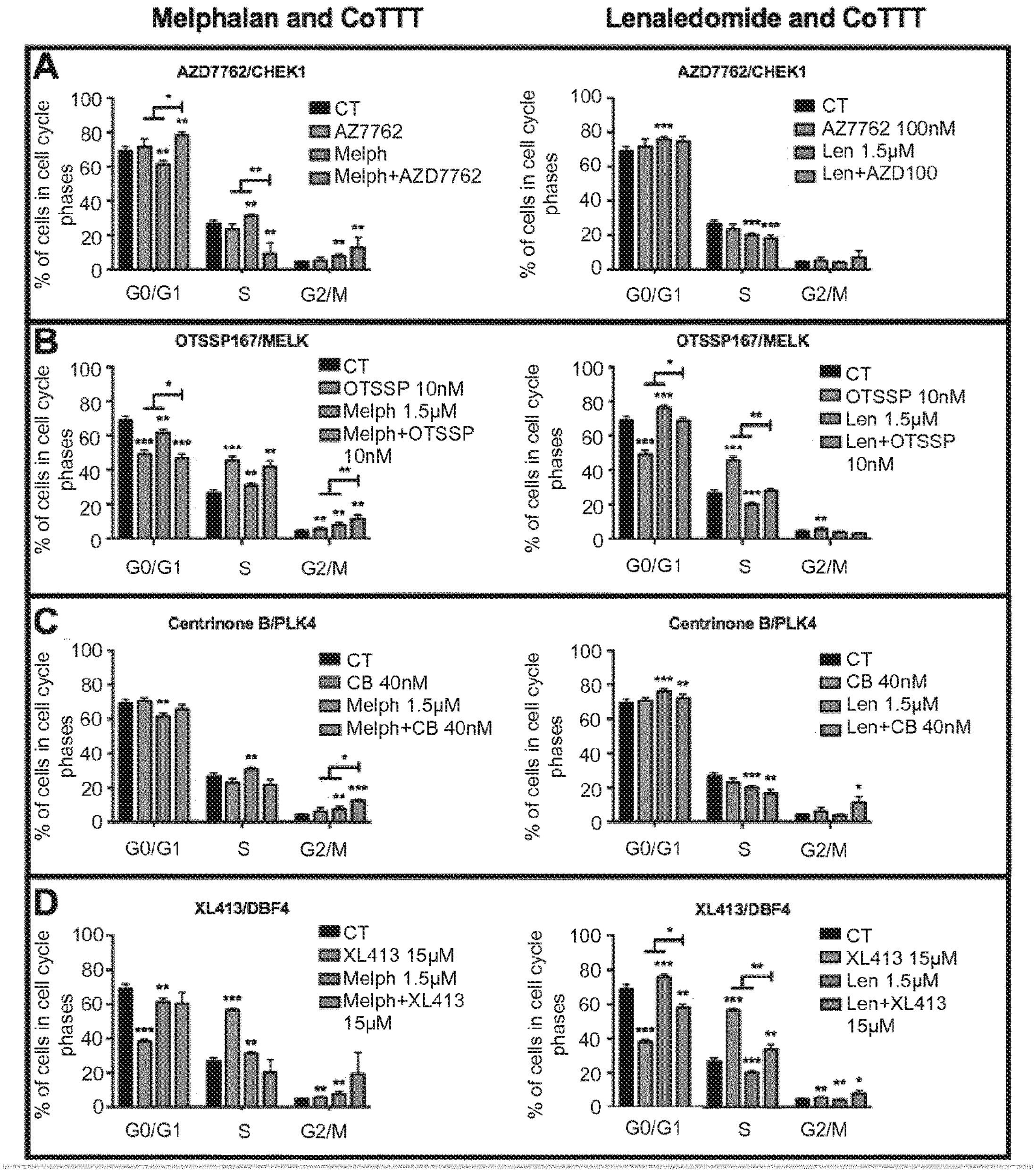
FIG. 29 represents graphs illustrating that Co-treatments differentially affect cell cycle in AMO1 cell line. Cotreatment with Melphalan or Lenalidomide and A) AZD7762; B) OTSSP167; C) Centrinone B; D) XL413. Cell cycle was monitored by flow cytometry after 4 days co-treatments. p-value: *<0.05; <0.01; *<0.001.

In the next set of experiment, the inventors evaluated cell death and apoptosis after co-treatments with kinases inhibitors and melphalan or lenalidomide, in order to investigate further the observed effect on AMO1. To clearly visualize the cumulative effect, the inventors used a sub-lethal dose of Melphalan or Lenalidomide with the calculated IC20 of the kinase's inhibitors. AZD7762/CHK1i, OTSSP167/MELKi and XL413/DBF4i increase cell death via apoptosis when cells were co-treated with melphalan or lenalidomide. In addition, Centrinone B/PLK4i co-treatment potentialized cell death only with lenalidomide (FIG. 25), while SRPIN340/SRPK1i and AZ3146/MPS1i didn't have any significant additional effect on cell death (FIG. 26), which is in accordance with results obtained on cell viability (FIGS. 20 and 23). Next, the inventors monitored DNA damages by measuring □H2AX for the different co-treatments. As expected, melphalan treatment alone, even at the sub-lethal dose, increased the measured □H2AX, while lenalidomide didn't demonstrate any particular effect (FIG. 27). However, on all the co-treatment tested only OTSSP167/MELK significantly potentialized the melphalan co-treatment by increasing □H2AX and therefore DNA damages. Interestingly OTSSP167/MELKi, XL413/DBF4i and SRPIN340/SRPK1i showed an activity on □H2AX recruitment when used alone (FIG. 27 and FIG. 28). Thus, the observed decrease in cell viability appears to be due to an increase in cell death, and not particularly to an increase of DNA damage. Finally, discrepancies were observed between single treatment and co-treatment when the inventors examined the cell cycle of AMO1 following co-treatments. Hence, AZD7762/CHK1i and Centrinone B/PLK4i co-treatments with melphalan or lenalidomide arrested the cell respectively in G0/G1 and G2/M instead of S and G0/G1 phases for the single treatments, which indicates profound modifications of the cell cycle. In contrast no differences between single and co-treatment could be observed with the OTSSP167/MELKi and XL413/PLK4i inhibitors (FIG. 29).

Figure 30:
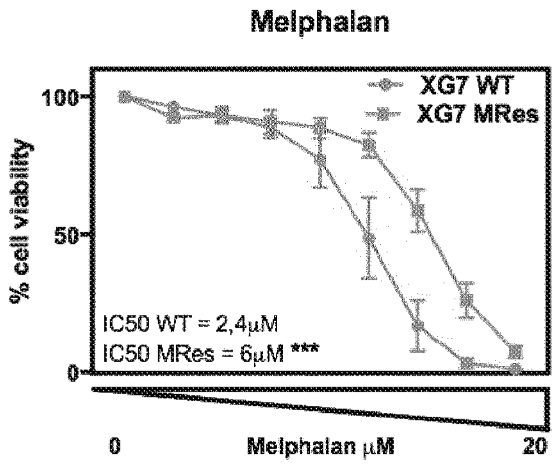
FIG. 30 is graph showing that Kinase inhibitors reduce viability of a melphalan resistant cell line. Melphalan sensitivity is measures in the two cell lines XG7 WT and XG7 Mres.
Figure 31:
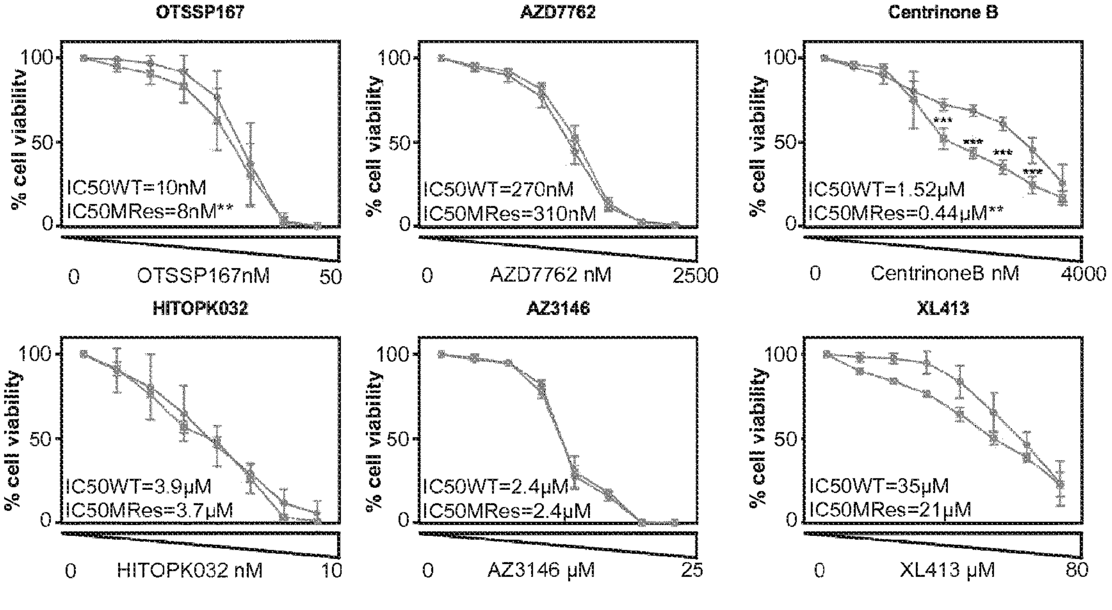
FIG. 31 represents graphs illustrating that Kinase inhibitors reduce viability of a melphalan resistant cell line. Assays for 6 kinases inhibitors are shown.

The facts that: 1) all drugs tested are actively decreasing HMCLs viability and induce apoptosis; 2) co-treatment with melphalan leads to synergy or potentialized the decrease of cell viability; 3) some of the selected kinases inhibitors can reverse the resistance to lenalidomide in AMO1 HMCL, led us to question the capability of these drugs to reverse or reduce also melphalan resistance. In that purpose, the inventors used a cell line developed in the inventors' laboratory, and that has been culture to resist to melphalan (Mres) compare to its negative control (WT) (FIG. 30). The inventors first tested the capacity of the different inhibitors to reduce cell viability in this model. All tested kinase's inhibitors lower cell viability of the control or the melphalan resistant cell line. Interestingly, while no clear differences could be observed for the 1050 of OTSSP167/MELKi, AZD7762/CHK1i, HITOPK032/PBKi and AZ3146/MPS1i in the melphalan resistant (Mres) and sensitive (WT) cell lines, Centrinone B/PLK4i and XL413/DBF4i significantly decreased cell viability in the Mres cell line (FIG. 31).

Figure 32:
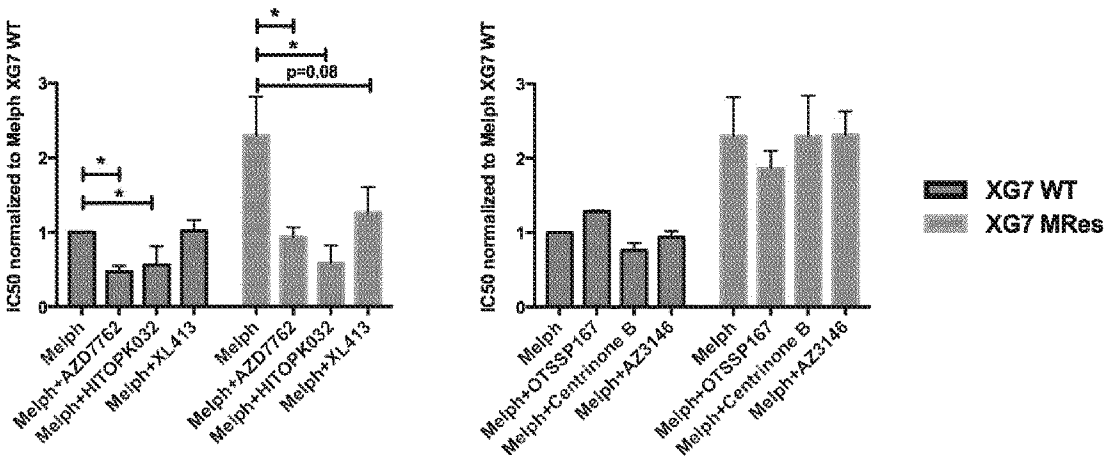
FIG. 32 represents a graph of the calculated IC50 for the co-treatment with melphalan and selected kinase inhibitors at IC20. Melphalan sensitive (XG7 WT) and Resistant (XG7 MRes) cell lines were treated for 4 days with the selected kinases inhibitors. Cell viability was monitored by the CTG. p-value: *<0.05; <0.01; *<0.001.

Next, the inventors analyzed cell behaviors to co-treatment with melphalan and kinase's inhibitors using the 1020. AZD7762/CHK1i, HITOPK032/PBKi but also XL413/DBF4i reversed the melphalan resistance of the cell line (FIG. 32), while the other inhibitors tested didn't modified melphalan resistance. It should however be underlined that the inhibitors alone are active on both resistant and sensitive cell lines as shown on FIG. 31.

Thus, the inventors' results highlight the therapeutic potential of the selected kinase's inhibitors used alone or in combination with conventional therapies, even in case of acquired resistance.

4—Discussion

Here the inventors identified 36 kinases as potential new targets in MM in combinatory treatments with conventional therapies or as alternative treatment. The inventors' strategy to use highly available data to investigate new therapeutics has revealed to be efficient, and the inventors validated new targets with already available inhibitors. In addition, the inventors also highlighted a list of potential new kinases for which inhibitors could be worth to be developed at least to treat MM.

In order to eliminate a maximum of false positive kinases linked to prognosis, the inventors progressively and selectively discriminated psets from the HM to the TT3 cohort. This has certain limitations, and the original cohort used could have its importance in the final number and identity of psets identified. Yet the inventors controlled that possibility, and when the inventors started the selection with the TT2 cohort a final list of 47psets was obtained. Among them only 7psets (AZU1, PRKCSH, CKS2, P14K2B, MELK, PTPRG, SRPK1) were missing from the 36 investigated in this study. Importantly the absence of the 7 genes was due to a loss of significativity in the TT2 cohort after multiple testing correction since the pvalue for these kinase were just at the upper limit of the inventors' threshold (not shown).

One previous study investigated the kinome in myeloma (Tiedemann et al., 2010). However, while Tiedemann et al. tested a RNAi library targeting the kinome on six human myeloma cell lines, here the inventors questioned the kinome for prognostic values on three independent cohorts and then validated some of the selected kinases on human and mouse myeloma cell lines and in primary human myeloma cells. Surprisingly only one gene (AURKA) was commonly selected in both studies. This discrepancy could origin from the fact that it certainly exists differences between HMCLs and patient's transcriptome, potentially leading to a bias in their result, which could be even emphasized by the over-activation of proliferation cascades in cell lines compared to tumoral cells (S phase MM=max 1%; S phase HMCLs>20%), or by the high number of kinase (226/661) significantly differentially expressed between MM cells and HMCLs (not shown).

One unexpected results of the inventors' analysis is that apart from MAP2K6 no kinases involved in highly studied pathway in cancer and already known to play a role in MM as IGF-1R (Mitsiades et al., 2004), VEGFR (Kovacs et al., 2006) PI-3K/AKT (Hsu et al., 2001; Hyun et al., 2000; Pene et al., 2002), IkB kinase (Bharti et al., 2003) PKC (Podar et al., 2007), FGFR3 (Chesi et al., 1997) or Janus Kinase (Pedranzini et al., 2006) were in the inventors' final 36psets list. Since major signaling kinases are usually connected to cancer following their mutation and/or their constitutive activation at the protein level (Sawyers, 2002), the fact that the inventors selected kinases on their gene expression pattern could be an explanation for this result. However it is surprising that the FGFR3 genes that is known to be overexpress in approximately 15% of MM (Chesi et al., 1997; Santra et al., 2003) or the IGF1R that was shown to be crucial in myeloma (Sprynski et al., 2009) were not in the selected final list of kinases. In fact, restrospective analysis of the kinome pset list obtained from literature show that it does not contain FGFR3. However, the inventors analyzed and validated the FGFR3 prognosis value in the inventors' cohort (not shown). On its part although IGF1R have significant prognosis value in the three cohorts (HM (p=0.014); TT2 (p=0.00038); TT3 (p=4.9e-05)), multiple correction in the HM cohort excluded it from further analysis. Nevertheless, although the starting kinase list has obviously its importance, considering the inventors' strategy of identifying only novel potential targets, as these genes are already well described to be linked to MM, they would have been excluded in the first steps of the inventors' strategy.

It is particularly remarkable that all tested inhibitors demonstrated anti myeloma activity by reducing viability of the HMCLs. When the inventors analyzed the potential mechanisms, cell cycle arrest and apoptosis were both contributing to the observed phenotype. It is however interesting that apoptosis related proteins activations were specifically deregulated depending on the treatments suggesting mechanisms differences in the inhibitors activities. In addition, while P53 appears to be involved in apoptosis mediated by AZD7762, OTSSP167 or Centrinone B in AMO1, the inventors believe that other mechanisms are also involved, since the different inhibitors affected cells viability in mutated (XG1, OPM2) or WT P53 (XG21, AMO1) cell lines. In the case of the CHK1 inhibitor AZD7762, the inventors' results are in favor of a P53 independent mechanism, since single treatment and co-treatments with AZD7762 and melphalan or lenalidomide were equivalent whatever the P53 status of the different HMCLs. In contrast, in other cell type AZD7762 activity has been shown to depend on P53 (Ma et al., 2012; Meng et al., 2015), therefore suggesting a potential cell/tissue specific activity of this molecule.

Virtually, all MM patients eventually relapse and develop drug resistance. Here, the fact that CHK1, MELK and PBK inhibitors reversed resistance to lenalidomide in the AMO1 HMCL, while CHK1, PBK and DBF4 inhibitors were able to reverse melphalan resistance in the XG7 model is spectacular and very promising. Considering their involvement in different steps of the cell cycle, no mechanism could be identified there, although the inventors' results demonstrated that the inhibitors are mainly acting via an improvement of apoptosis pathway, which was relatively specific to MM compared to normal microenvironment cells as shown in primary patient cells. Further efforts are now necessary to lead preclinical studies, and confirm the inventors' observation in vivo. However, the inventors' preliminary results obtained on the mouse model are very promising, and the inventors are therefore confident on the potential of the identified targets as complementary therapies which would certainly improved patients outcome.

One of the first highlight after analyzing the kinases connected with survival in MM patients, was the particular role of the cell cycle kinases in this process. Although to the inventors' knowledge this is the first time that a strong cell cycle signature is efficiently correlated to prognosis in MM, this result is not particularly surprising as proliferation is an identified risk factor in MM (Garcia-Sanz et al., 2004; Hose et al., 2011). However, when the inventors compared the 36 genes of the KI to the 50 genes of the GPI (Hose et al., 2011) that represent proliferation, the inventors observed only 9 (<12%) elements in common (AURKA; BUB1; BUB1B; CDKN3; CHEK1; CKS1B; CKS2; NEK2; PLK4) between the two, which indicates that the two signatures are independent. On the therapeutic point of view, considering the fact that the inventors target essential kinases involved in cell cycle, the potential general toxicity of the drugs used in vivo could be questionable. However, it is now accepted that targeting the cell cycle is a win-win strategy (Maes et al., 2017; Otto and Sicinski, 2017), and in the inventors' case some of the inhibitors used have already passed the preclinical development for other conditions. Moreover, considering the potential benefit of such treatment on drug resistance at very low doses, the selected kinase inhibitors are still of great interest in the inventors' opinion, although additional in vivo experimentation are needed to confirm their potential.

Among the 7 targets validated here, the CHK1 inhibitor AZD7762 was of particular interest due in part to its activity in drug resistance reversion. While a good activity of the molecule alone or in combination characterized the inventors' observation two previous studies in myeloma obtained divergent results. Thus, both noted limited lethality of the drug alone at doses equivalent of the inventors' calculated 1050. In addition, AZD7762 cotreatment with melphalan was also performed but at extremely high concentration of melphalan compare to the inventors' study (Landau et al., 2012; Pei et al., 2011). As the treatment kinetic seems to be comparable these discrepancies could be due to HMCLs used, or the confluency status of the cells at seeding or even the treatment protocol since HMCLs are highly sensitive to these parameters. Nevertheless, the inventors' study greatly implements these results on the activity of the molecule alone or in combination, but also on drug resistance.

OTSSP167, the MELK inhibitor also demonstrated great potential and was consistent in every experiment performed here. MELK is linked to multiple solid cancer types (Gray et al., 2005; Kuner et al., 2013; Lin et al., 2007), and at the time the inventors performed the last experiments of the inventors' study, in a letter to the editor Stefka et al. showed the potential of this inhibitor in MM (Stefka et al., 2016). In addition to their work the inventors here demonstrated the positive effect of OTSSP167 on conventional therapy and in resistant cells. However, it should be noticed that another study published during the finalization of the manuscript questioned the relevance of OTSSP167 as a specific MELK inhibitor (Lin et al., 2017). Discrepancies between the original study describing OTSSP167 activity as specific of MELK kinase (Chung et al., 2012) and the study by Lin et al, could potentially be explained by off-target activities of OTSSP167 on Aurora B, BUB1, TTK/MPS1 or Haspin kinase (Ji et al., 2016), which make OTSSP167 a drug targeting mitotic checkpoint. Be this as it may, Lin et al. performed molecular knock in or knock out of MELK, while the inventors didn't modify MELK expression or activity except with the inhibitor. Then the inventors cannot conclude about the specificity or the off-target probability of OTSSP167 in the inventors' model, but in the case the inventors consider the identified off-targets, BUB1 and TTK/MPS1 are also part of the inventors' 36 selected kinases, which further highlight the potential of this inhibitor in the inventors' model to treat MM, and may could explain its outstanding activity.

To the inventors' knowledge the inventors are the first to have evaluated the potential therapeutical potential of PLK4, DBF4, MPS1, PBK and SRPK1 in myeloma, although their potential role in other cancers have been demonstrated (Bonte et al., 2008; Bullock and Oltean, 2017; Liu, 2015; Ohashi et al., 2017; Xie et al., 2017). Although all inhibitors did not have comparable effect, it is clearly exceptional that they all demonstrated potential activity at least when used alone. For the different co-treatment tested however the inventors did not always observed synergy when used at low doses, but no negative effect could neither be observed, thus they remain good therapeutic option in the treatment of MM, and preclinical studies are worth to be performed.

Conclusion

It is important to keep in mind that to date no kinase's inhibitors have received the approval of the FDA for the treatment of MM (Abramson, 2016). The inventors' study here demonstrates, that kinase inhibitors could be of remarkable benefits in this pathology. Indeed, some inhibitors could even reverse at very low concentration conventional therapy resistance, therefore giving the possibility to use at concentration that could limit any potential adverse effect. This study contributes to increase the treatments options, and could be a good drive for innovation in developing new specific inhibitors as in MM therapy.

5—Summary

Multiple Myeloma (MM) account for approximately 10% of hematological malignancies and is the second most common hematological disorder. Active research on MM allowed great improvement in new treatments discovery, including proteasomes inhibitors or immunomodulatory agents, that enhanced significantly the patients median survival from 3-4 years in the 90's to 7-8 years nowadays. However there is a vital need for additional therapies since until today, MM is a condition that cannot be cured, and all patients finally relapse. Although numbers of kinases inhibitors are currently used, under development or already in clinical trial in cancers, kinases have only be poorly studied in MM. Thus only one study (Tiedeman R E Blood 2010) examined the kinome in MM by using a screening of siRNA in Human Myeloma Cell lines (HMCL).

Here, in contrast to Tiedeman et al., the inventors evaluated the potential of kinase involvement directly on patient outcome. The inventors first performed kinome in silico analysis in three independent cohorts of patients, and identified 36 kinases significantly and identically involved in patient's survival. The inventors built a Kinome Index (KI) from the 36 kinases expression, and showed that KI: 1) is related to OS and EFS prognosis in 3 cohorts, 2) is linked to proliferation and bad prognosis subgroups of MM patient's classification, 3) is associated with relapse. Among the 36 targets, only 7 had available commercial inhibitors and were not already consistently studied in MM (PBK, SRPK1, CDC7-DBF4, MELK, CHK1, PLK4, MPS1/TTK). The inventors then tested for their activity the inhibitors against these 7 kinases in 4 HMCLs representing two IL-6 independent (AMO1, OPM2) and two IL-6 dependent (XG1, XG21) cell lines. All tested inhibitors significantly reduced viability of the cells, and had IC50 from the nanomolar (for MELKi, CHK1i and PLK4i) to the micromolar range (for PBKi, SRPK1i, CDC7-DBF4i and MPS1/TTKi). Annexin, PARP and cell cycle analysis following treatment with selected concentration of the inhibitors in AMO1, showed an increase in apoptosis, associated for most of them with a perturbation of the cell cycle. Treatment of Primary Human Myeloma Cells with MELKi, CHK1i and PLK4i decreased tumoral cells while they didn't impact the normal bone marrow microenvironment. Similarly, preclinical experiments on mouse Myeloma cells confirmed the potential of these three inhibitors.

Next, 1020 of the different inhibitors were tested in co-treatment with melphalan, lenalidomide or velcade in XG1, XG21, AMO1 and OPM2 to challenge the capabilities of the selected kinases inhibitors to potentialize major routinely used therapeutics. The inventors first didn't observe any synergy for the co-treatments with velcade, although all the kinases inhibitors used had at least a neutral or a positive impact on the three conventional therapies. Conversely, some of the kinases inhibitors (CHK1i, MELKi, PBKi, DBF4i with melphalan, CHK1i, MELKi, PLK4i, PBKi, SRPK1i with lenalidomide) synergized with the conventional treatment, thus highlighting their potential benefic effect in MM therapy. Analysis of apoptosis and cell cycle following co-treatments with melphalan and lenalidomide in AMO1 cells showed an increased in PARP and annexin detection and deregulation of the cell cycle for the co-treatments. One of the outstanding co-treatment effects was the reversion of the natural AMO1's resistance to lenalidomide with CHK1, MELK and PBK inhibitors used at their 1020. The inventors then tested if a reversion of melphalan resistance could also be monitored, using a WT (XG7-WT) and resistant (XG7-Mres) cell lines. PLK4 and DBF4 inhibitors demonstrated higher activity on XG7-Mres cells compared to their WT control. In addition CHK1, PBK and DBF4 inhibitors were able to re-sensitize XG7-Mres to melphalan at a similar level than XG7-WT. Altogether the inventors identified 36 new potential kinases targets in MM, with seven targets that the inventors validated in this study. The inventors demonstrated the interest of using kinases inhibitors that are available and sometimes already clinically tested in combination with conventional therapy in MM. Then the inventors suggest the development of new kinases inhibitors targeting the identified kinases to improve treatment response for MM patients. And the development of pre- and clinical trial with the above tested kinases inhibitors in MM.

6—Bibliography

Abramson, H. N. (2016). Kinase inhibitors as potential agents in the treatment of multiple myeloma. Oncotarget 7, 81926-81968.

Anderson, K. C. (2012). The 39th David A. Karnofsky Lecture: bench-to-bedside translation of targeted therapies in multiple myeloma. J. Clin. Oncol. Off. J. Am. Soc. Clin. Oncol. 30, 445-452.

Anderson, K. C., and Carrasco, R. D. (2011). Pathogenesis of myeloma. Annu. Rev. Pathol. 6, 249-274.

Barlogie, B., Tricot, G., Rasmussen, E., Anaissie, E., van Rhee, F., Zangari, M., Fassas, A., Hollmig, K., Pineda-Roman, M., Shaughnessy, J., et al. (2006). Total therapy 2 without thalidomide in comparison with total therapy 1: role of intensified induction and posttransplantation consolidation therapies. Blood 107, 2633-2638.

Bharti, A. C., Donato, N., Singh, S., and Aggarwal, B. B. (2003). Curcumin (diferuloylmethane) down-regulates the constitutive activation of nuclear factor-kappa B and IkappaBalpha kinase in human multiple myeloma cells, leading to suppression of proliferation and induction of apoptosis. Blood 101, 1053-1062.

Bonte, D., Lindvall, C., Liu, H., Dykema, K., Furge, K., and Weinreich, M. (2008). Cdc7-Dbf4 kinase overexpression in multiple cancers and tumor cell lines is correlated with p53 inactivation. Neoplasia N. Y. N 10, 920-931.

Bullock, N., and Oltean, S. (2017). The many faces of SRPK1. J. Pathol. 241, 437-440.

Chesi, M., Nardini, E., Brents, L. A., Schröck, E., Ried, T., Kuehl, W. M., and Bergsagel, P. L. (1997). Frequent translocation t (4; 14)(p16.3;q32.3) in multiple myeloma is associated with increased expression and activating mutations of fibroblast growth factor receptor 3. Nat. Genet. 16, 260-264.

Chou, T. C., and Talalay, P. (1984). Quantitative analysis of dose-effect relationships: the combined effects of multiple drugs or enzyme inhibitors. Adv. Enzyme Regul. 22, 27-55.

Chung, S., Suzuki, H., Miyamoto, T., Takamatsu, N., Tatsuguchi, A., Ueda, K., Kijima, K., Nakamura, Y., and Matsuo, Y. (2012). Development of an orally-administrative MELK-targeting inhibitor that suppresses the growth of various types of human cancer. Oncotarget 3, 1629-1640.

Evans, R., Naber, C., Steffler, T., Checkland, T., Keats, J., Maxwell, C., Perry, T., Chau, H., Belch, A., Pilarski, L., et al. (2008). Aurora A kinase RNAi and small molecule inhibition of Aurora kinases with VE-465 induce apoptotic death in multiple myeloma cells. Leuk. Lymphoma 49, 559-569.

Fleuren, E. D. G., Zhang, L., Wu, J., and Daly, R. J. (2016). The kinome "at large" in cancer. Nat. Rev. Cancer 16, 83-98.

García-Sanz, R., González-Fraile, M. I., Mateo, G., Hernandez, J. M., López-Berges, M. C., de las Heras, N., Fernández-Calvo, J., Ortega, F., Portero, J. A., Bárez, A., et al. (2004). Proliferative activity of plasma cells is the most relevant prognostic factor in elderly multiple myeloma patients. Int. J. Cancer 112, 884-889.

Gray, D., Jubb, A. M., Hogue, D., Dowd, P., Kljavin, N., Yi, S., Bai, W., Frantz, G., Zhang, Z., Koeppen, H., et al. (2005). Maternal embryonic leucine zipper kinase/murine protein serine-threonine kinase 38 is a promising therapeutic target for multiple cancers. Cancer Res. 65, 9751-9761.

Hose, D., Rème, T., Hielscher, T., Moreaux, J., Messner, T., Seckinger, A., Benner, A., Shaughnessy, J. D., Barlogie, B., Zhou, Y., et al. (2011). Proliferation is a central independent prognostic factor and target for personalized and risk-adapted treatment in multiple myeloma. Haematologica 96, 87-95.

Hothorn, T., and Lausen, B. (2003). On the exact distribution of maximally selected rank statistics. Comput Stat Data Anal 121-137.

Hsu, J., Shi, Y., Krajewski, S., Renner, S., Fisher, M., Reed, J. C., Franke, T. F., and Lichtenstein, A. (2001). The AKT kinase is activated in multiple myeloma tumor cells. Blood 98, 2853-2855.

Hyun, T., Yam, A., Pece, S., Xie, X., Zhang, J., Miki, T., Gutkind, J. S., and Li, W. (2000). Loss of PTEN expression leading to high Akt activation in human multiple myelomas. Blood 96, 3560-3568.

Ji, W., Arnst, C., Tipton, A. R., Bekier, M. E., Taylor, W. R., Yen, T. J., and Liu, S.-T. (2016). OTSSP167 Abrogates Mitotic Checkpoint through Inhibiting Multiple Mitotic Kinases. PloS One 11, e0153518.

Jourdan, M., Caraux, A., De Vos, J., Fiol, G., Larroque, M., Cognot, C., Bret, C., Duperray, C., Hose, D., and Klein, B. (2009). An in vitro model of differentiation of memory B cells into plasmablasts and plasma cells including detailed phenotypic and molecular characterization. Blood 114, 5173-5181.

Jourdan, M., Cren, M., Robert, N., Bolloré, K., Fest, T., Duperray, C., Guilloton, F., Hose, D., Tarte, K., and Klein, B. (2014). IL-6 supports the generation of human long-lived plasma cells in combination with either APRIL or stromal cell-soluble factors. Leukemia 28, 1647-1656.

Kassambara, A., Rème, T., Jourdan, M., Fest, T., Hose, D., Tarte, K., and Klein, B. (2015). GenomicScape: an easy-to-use web tool for gene expression data analysis. Application to investigate the molecular events in the differentiation of B cells into plasma cells. PLoS Comput. Biol. 11, e1004077.

Kovacs, M. J., Reece, D. E., Marcellus, D., Meyer, R. M., Mathews, S., Dong, R.-P., and Eisenhauer, E. (2006). A phase II study of ZD6474 (Zactima, a selective inhibitor of VEGFR and EGFR tyrosine kinase in patients with relapsed multiple myeloma—NCIC CTG IND.145. Invest. New Drugs 24, 529-535.

Kuner, R., Fälth, M., Pressinotti, N. C., Brase, J. C., Puig, S. B., Metzger, J., Gade, S., Schäfer, G., Bartsch, G., Steiner, E., et al. (2013). The maternal embryonic leucine zipper kinase (MELK) is upregulated in high-grade prostate cancer. J. Mol. Med. Berl. Ger. 91, 237-248.

Kyle, R. A., and Rajkumar, S. V. (2004). Multiple myeloma. N. Engl. J. Med. 351, 1860-1873.

Landau, H. J., McNeely, S. C., Nair, J. S., Comenzo, R. L., Asai, T., Friedman, H., Jhanwar, S. C., Nimer, S. D., and Schwartz, G. K. (2012). The checkpoint kinase inhibitor AZD7762 potentiates chemotherapy-induced apoptosis of p53-mutated multiple myeloma cells. Mol. Cancer Ther. 11, 1781-1788.

Lin, A., Giuliano, C. J., Sayles, N. M., and Sheltzer, J. M. (2017). CRISPR/Cas9 mutagenesis invalidates a putative cancer dependency targeted in on-going clinical trials. eLife 6.

Lin, M.-L., Park, J.-H., Nishidate, T., Nakamura, Y., and Katagiri, T. (2007). Involvement of maternal embryonic leucine zipper kinase (MELK) in mammary carcinogenesis through interaction with Bcl-G, a pro-apoptotic member of the Bcl-2 family. Breast Cancer Res. BCR 9, R17.

Liu, X. (2015). Targeting Polo-Like Kinases: A Promising Therapeutic Approach for Cancer Treatment. Transl. Oncol. 8, 185-195.

Ma, Z., Yao, G., Zhou, B., Fan, Y., Gao, S., and Feng, X. (2012). The Chk1 inhibitor AZD7762 sensitises p53 mutant breast cancer cells to radiation in vitro and in vivo. Mol. Med. Rep. 6, 897-903.

Maes, A., Menu, E., Veirman, K. D., Maes, K., Vanderkerken, K., and Bruyne, E. D. (2017). The therapeutic potential of cell cycle targeting in multiple myeloma. Oncotarget.

Meng, F., Bhupathi, D., Sun, J. D., Liu, Q., Ahluwalia, D., Wang, Y., Matteucci, M. D., and Hart, C. P. (2015). Enhancement of hypoxia-activated prodrug TH-302 anti-tumor activity by Chk1 inhibition. BMC Cancer 15, 422.

Mitsiades, C. S., Mitsiades, N. S., McMullan, C. J., Poulaki, V., Shringarpure, R., Akiyama, M., Hideshima, T., Chauhan, D., Joseph, M., Libermann, T. A., et al. (2004). Inhibition of the insulin-like growth factor receptor-1 tyrosine kinase activity as a therapeutic strategy for multiple myeloma, other hematologic malignancies, and solid tumors. Cancer Cell 5, 221-230.

Moreaux, J., Klein, B., Bataille, R., Descamps, G., Maïga, S., Hose, D., Goldschmidt, H., Jauch, A., Rème, T., Jourdan, M., et al. (2011). A high-risk signature for patients with multiple myeloma established from the molecular classification of human myeloma cell lines. Haematologica 96, 574-582.

Moreaux, J., Rème, T., Leonard, W., Veyrune, J.-L., Requirand, G., Goldschmidt, H., Hose, D., and Klein, B. (2012). Development of gene expression-based score to predict sensitivity of multiple myeloma cells to DNA methylation inhibitors. Mol. Cancer Ther. 11, 2685-2692.

Nair, B., van Rhee, F., Shaughnessy, J. D., Anaissie, E., Szymonifka, J., Hoering, A., Alsayed, Y., Waheed, S., Crowley, J., and Barlogie, B. (2010). Superior results of Total Therapy 3 (2003-33) in gene expression profiling-defined low-risk multiple myeloma confirmed in subsequent trial 2006-66 with VRD maintenance. Blood 115, 4168-4173.

Ohashi, T., Komatsu, S., Ichikawa, D., Miyamae, M., Okajima, W., Imamura, T., Kiuchi, J., Kosuga, T., Konishi, H., Shiozaki, A., et al. (2017). Overexpression of PBK/TOPK relates to tumour malignant potential and poor outcome of gastric carcinoma. Br. J. Cancer 116, 218-226.

Otto, T., and Sicinski, P. (2017). Cell cycle proteins as promising targets in cancer therapy. Nat. Rev. Cancer 17, 93-115.

Pedranzini, L., Dechow, T., Berishaj, M., Comenzo, R., Zhou, P., Azare, J., Bornmann, W., and Bromberg, J. (2006). Pyridone 6, a pan-Janus-activated kinase inhibitor, induces growth inhibition of multiple myeloma cells. Cancer Res. 66, 9714-9721

Pei, X.-Y., Dai, Y., Youssefian, L. E., Chen, S., Bodie, W. W., Takabatake, Y., Felthousen, J., Almenara, J. A., Kramer, L. B., Dent, P., et al. (2011). Cytokinetically quiescent (G0/G1) human multiple myeloma cells are susceptible to simultaneous inhibition of Chk1 and MEK1/2. Blood 118, 5189-5200.

Pene, F., Claessens, Y.-E., Muller, O., Viguié, F., Mayeux, P., Dreyfus, F., Lacombe, C., and Bouscary, D. (2002). Role of the phosphatidylinositol 3-kinase/Akt and mTOR/P70S6-kinase pathways in the proliferation and apoptosis in multiple myeloma. Oncogene 21, 6587-6597.

Podar, K., Raab, M. S., Zhang, J., McMillin, D., Breitkreutz, I., Tai, Y.-T., Lin, B. K., Munshi, N., Hideshima, T., Chauhan, D., et al. (2007). Targeting PKC in multiple myeloma: in vitro and in vivo effects of the novel, orally available small-molecule inhibitor enzastaurin (LY317615.HCl). Blood 109, 1669-1677.

Röllig, C., Knop, S., and Bornhauser, M. (2015). Multiple myeloma. Lancet Lond. Engl. 385, 2197-2208.

Sabatier, R., Finetti, P., Mamessier, E., Raynaud, S., Cervera, N., Lambaudie, E., Jacquemier, J., Viens, P., Birnbaum, D., and Bertucci, F. (2011). Kinome expression profiling and prognosis of basal breast cancers. Mol. Cancer 10, 86.

Santra, M., Zhan, F., Tian, E., Barlogie, B., and Shaughnessy, J. (2003). A subset of multiple myeloma harboring the t(4; 14)(p16;q32) translocation lacks FGFR3 expression but maintains an IGH/MMSET fusion transcript. Blood 101, 2374-2376.

Sawyers, C. L. (2002). Rational therapeutic intervention in cancer: kinases as drug targets. Curr. Opin. Genet. Dev. 12, 111-115.

Shaughnessy, J. (2005). Amplification and overexpression of CKS1B at chromosome band 1q21 is associated with reduced levels of p27Kip1 and an aggressive clinical course in multiple myeloma. Hematol. Amst. Neth. 10 Suppl 1, 117-126.

Shi, L., Wang, S., Zangari, M., Xu, H., Cao, T. M., Xu, C., Wu, Y., Xiao, F., Liu, Y., Yang, Y., et al. (2010). Overexpression of CKS1B activates both MEK/ERK and JAK/STAT3 signaling pathways and promotes myeloma cell drug-resistance. Oncotarget 1, 22-33.

Siegel, R., Naishadham, D., and Jemal, A. (2012). Cancer statistics, 2012. CA. Cancer J. Clin. 62, 10-29.

Sprynski, A. C., Hose, D., Caillot, L., Rème, T., Shaughnessy, J. D., Barlogie, B., Seckinger, A., Moreaux, J., Hundemer, M., Jourdan, M., et al. (2009). The role of IGF-1 as a major growth factor for myeloma cell lines and the prognostic relevance of the expression of its receptor. Blood 113, 4614-4626.

Stefka, A. T., Park, J.-H., Matsuo, Y., Chung, S., Nakamura, Y., Jakubowiak, A. J., and Rosebeck, S. (2016). Anti-myeloma activity of MELK inhibitor OTS167: effects on drug-resistant myeloma cells and putative myeloma stem cell replenishment of malignant plasma cells. Blood Cancer J. 6, e460.

Tiedemann, R. E., Zhu, Y. X., Schmidt, J., Yin, H., Shi, C.-X., Que, Q., Basu, G., Azorsa, D., Perkins, L. M., Braggio, E., et al. (2010). Kinome-wide RNAi studies in human multiple myeloma identify vulnerable kinase targets, including a lymphoid-restricted kinase, GRK6. Blood 115, 1594-1604.

Xie, Y., Wang, A., Lin, J., Wu, L., Zhang, H., Yang, X., Wan, X., Miao, R., Sang, X., and Zhao, H. (2017). Mps1/TTK: a novel target and biomarker for cancer. J. Drug Target. 25, 112-118.

Zhan, F., Huang, Y., Colla, S., Stewart, J. P., Hanamura, I., Gupta, S., Epstein, J., Yaccoby, S., Sawyer, J., Burington, B., et al. (2006). The molecular classification of multiple myeloma. Blood 108, 2020-2028.

The invention is not limited to the above-mentioned embodiments, and other ones could be identified by the skilled person.

The invention claimed is:

1. A method for the treatment of an individual afflicted by a multiple myeloma comprising the steps of:

A) identifying a patient having a bad outcome by performing the following steps:

a. measuring, in a biological sample, the expression level of at least 28 genes, said 28 genes belonging to a set of 36 genes, said 28 genes consisting of the genes AURKA, BUB1, BUB1B, CDC7, CDKN2C, CDKN3, CHEK1, CKS1B, CKS2, DBF4, DUSP10, HK2, PI4K2B, MAP2K6, MELK, NEK2, NTRK3, PAK2, PBK, PFKP, PLK4, PTPRG, RPRD1A, SRPK1, SRPK2, STK39, TK1 and TTK, said expression level being normalized compared to said 36 genes in order to obtain a normalized expression level for each of said at least 28 genes, b. calculating an index KI, said KI representing the sum of the normalized expression level obtained for each of said at least 28 genes, c. classifying the individual such that:

if the index KI is higher than a reference value, the individual is likely to have a bad outcome, and if the score value is lower than a reference value, the individual is likely to have a good outcome, said reference value being 1.31;

B) administering to the patient having a bad outcome an effective amount of at least a specific inhibitor of one of the following kinases MELK, PBK, CHK1, SRPK1, DBF4 and PLK4, or a combination thereof wherein said inhibitor is one of OTSSP167, HITOPK032, AZD7762, SRPIN340, XL413 and Centrinone B/LCR 323.

2. The method according to claim 1, wherein step a. is a step of measuring the expression level of at least 10 genes chosen among said group of 28 genes, said reference value being 0.79.

3. The method for the treatment of an individual according to claim 1, wherein step a. is a step of measuring the expression level of all the genes of said set of 36 genes, and wherein said reference value is 2.1, said set of 36 genes consisting of AZU1, CDKN1A, DDR1, HK3, MAP4K2, MERTK, PRKCSH, TESK2, AURKA, BUB1, BUB1B, CDC7, CDKN2C, CDKN3, CHEK1, CKS1B, CKS2, DBF4, DUSP10, HK2, PI4K2B, MAP2K6, MELK, NEK2, NTRK3, PAK2, PBK, PFKP, PLK4, PTPRG, RPRD1A, SRPK1, SRPK2, STK39, TK1 and TTK.

4. A method for the treatment of an individual afflicted by a multiple myeloma having a bad outcome, comprising the administration of an effective amount of at least a specific inhibitor of one of the following kinases: MELK, PBK, CHK1, SRPK1, DBF4 and PLK4, or a combination thereof, wherein said multiple myeloma having a bad outcome is determined by the method of claim 1.

5. The method according to claim 4, wherein the effective amount of at least a specific inhibitor of one at least of the following kinases: MELK, PBK, CHK1, SRPK1, DBF4 and PLK4, is administered with at least a drug used for treating multiple myeloma.

6. The method according to claim 5, wherein said drug used for treating multiple myeloma is lenalidomide, melphalan, bortezomib and thalidomide.

7. The method according to claim 5, wherein it is administered:

melphalan and one of at least OTSSP167, AZD7762, HITOPK032, and XL413, or lenalidomide and one of at least OTSSP167, AZD7762, HITOPK032, and XL413.

8. The method according to claim 4, wherein said a multiple myeloma having a bad outcome are lenalidomide- or melphalan-resistant multiple myeloma.

9. The method according to claim 5, wherein said drug used for treating multiple myeloma and said inhibitor are used simultaneously, separately, or sequentially.

10. A composition comprising:

a. a drug used for treating multiple myeloma, for which some resistance may occur, and b. at least a specific inhibitor of one at least of the following kinases: MELK, PBK, CHK1, SRPK1, DBF4 and PLK4, or a combination thereof wherein said inhibitor is one of OTSSP167, HITOPK032, AZD7762, SRPIN340, XL413 and Centrinone B/LCR 323.

11. The composition according to claim 10, further comprising a pharmaceutically acceptable vehicle.

12. The composition according to claim 10, wherein said drug is one of lenalidomide, melphalan, bortezomib and thalidomide.

13. A method for the treatment of an individual afflicted by a multiple myeloma having a bad outcome, comprising the administration of an effective amount of at least a specific inhibitor of one of the following kinases: MELK, PBK, CHK1, SRPK1, DBF4 and PLK4, or a combination thereof, wherein said multiple myeloma having a bad outcome is determined by the method of claim 1, and wherein the specific inhibitor is chosen among the following ones: OTSSP167, HITOPK032, AZD7762, SRPIN340, XL413 and Centrinone B/LCR 323.

* * * * *